US012629364B2

(12) United States Patent
Zhang et al.

(10) Patent No.: US 12,629,364 B2
(45) **Date of Patent: *May 19, 2026**

(54) METHODS OF TREATING CANCERS OVEREXPRESSING CARM1 WITH EZH2 INHIBITORS AND PLATINUM-BASED ANTINEOPLASTIC DRUGS

(71) Applicant: The Wistar Institute of Anatomy and Biology, Philadelphia, PA (US)

(72) Inventors: Rugang Zhang, Elkins Park, PA (US); Sergey Karakashev, Philadelphia, PA (US)

(73) Assignee: The Wistar Institute of Anatomy and Biology, Philadelphia, PA (US)

(*) Notice: Subject to any disclaimer, the term of this patent is extended or adjusted under 35 U.S.C. 154(b) by 569 days.

This patent is subject to a terminal disclaimer.

(21) Appl. No.: 17/240,594

(22) Filed: Apr. 26, 2021

(65) Prior Publication Data

US 2021/0251987 A1 Aug. 19, 2021

Related U.S. Application Data

(63) Continuation of application No. 16/098,753, filed as application No. PCT/US2017/029170 on Apr. 24, 2017, now Pat. No. 10,987,353.

(60) Provisional application No. 62/366,935, filed on Jul. 26, 2016, provisional application No. 62/331,936, filed on May 4, 2016, provisional application No. 62/331,792, filed on May 4, 2016.

(51) Int. Cl.

| | |
|---|---|
| ***A61K 31/496*** | (2006.01) |
| ***A61K 31/437*** | (2006.01) |
| ***A61K 31/4439*** | (2006.01) |
| ***A61K 31/444*** | (2006.01) |
| ***A61K 31/519*** | (2006.01) |
| ***A61K 31/5377*** | (2006.01) |
| ***A61K 33/24*** | (2019.01) |
| ***A61K 33/243*** | (2019.01) |
| ***A61K 45/06*** | (2006.01) |
| ***A61P 35/00*** | (2006.01) |
| ***C07D 401/12*** | (2006.01) |
| ***C07D 401/14*** | (2006.01) |
| ***C07D 405/12*** | (2006.01) |
| ***C07D 471/04*** | (2006.01) |
| ***C07D 473/34*** | (2006.01) |

(52) U.S. Cl.

CPC .......... *A61K 31/496* (2013.01); *A61K 31/437* (2013.01); *A61K 31/4439* (2013.01); *A61K 31/444* (2013.01); *A61K 31/519* (2013.01); *A61K 31/5377* (2013.01); *A61K 33/24* (2013.01); *A61K 33/243* (2019.01); *A61K 45/06* (2013.01); *A61P 35/00* (2018.01); *C07D 401/12* (2013.01); *C07D 401/14* (2013.01); *C07D 405/12* (2013.01); *C07D 471/04* (2013.01); *C07D 473/34* (2013.01)

(58) Field of Classification Search

CPC .. A61K 31/496; A61K 33/243; A61K 31/437; A61K 31/4439; A61K 31/444; A61K 31/519; A61K 31/5377; A61K 33/24; A61K 45/06; A61P 35/00; C07D 401/12; C07D 401/14; C07D 405/12; C07D 471/04; C07D 473/34

See application file for complete search history.

(56) References Cited

U.S. PATENT DOCUMENTS

| | | | |
|---|---|---|---|
| 3,758,681 | A | 9/1973 | Hamill et al. |
| 4,140,707 | A | 2/1979 | Cleare et al. |
| 4,169,846 | A | 10/1979 | Kidani et al. |
| 5,072,011 | A | 12/1991 | Abrams et al. |
| 5,244,919 | A | 9/1993 | Abrams et al. |
| 5,420,319 | A | 5/1995 | Okamoto et al. |
| 5,665,771 | A | 9/1997 | Murrer |
| 5,716,988 | A | 2/1998 | Ibrahim et al. |

(Continued)

FOREIGN PATENT DOCUMENTS

| | | | |
|---|---|---|---|
| FR | 2664277 | A1 | 10/1992 |
| WO | WO-2013049770 | A2 * | 4/2013 |

(Continued)

OTHER PUBLICATIONS

Cheng et al. "Overexpression of CARM1 in breast cancer is correlated with poorly characterized clinicopathologic parameters and molecular subtypes," Diagnostic Pathology 2013, 8:129 pp. 1-9 (Year: 2013).*

(Continued)

*Primary Examiner* — Adam C Milligan
*Assistant Examiner* — William Y Lee
(74) *Attorney, Agent, or Firm* — Morgan, Lewis & Bockius LLP

(57) ABSTRACT

In some embodiments, therapeutic treatments for a disease such as a cancer are disclosed, including pharmaceutical compositions and methods of using pharmaceutical compositions for treating the cancer wherein the cancer cells overexpress arginine methyltransferase CARM1. In some embodiments, the therapeutic treatments disclosed include methods comprising the step of administering a therapeutically effective dose of an enhancer of zeste homolog 2 (EZH2) inhibitor to a subject, including a human subject, wherein the cancer cells of the subject overexpress arginine methyltransferase CARM1. In some embodiments, the EZH2 inhibitors are administered in conjunction with platinum-based antineoplastic drugs.

7 Claims, 39 Drawing Sheets

Specification includes a Sequence Listing.

(56) References Cited

U.S. PATENT DOCUMENTS

| | | | |
|---|---|---|---|
| 6,511,676 B1 | 1/2003 | Boulikas | |
| 6,518,428 B1 | 2/2003 | Wong et al. | |
| 8,410,088 B2 | 4/2013 | Kuntz et al. | |
| 8,536,179 B2 | 9/2013 | Miller et al. | |
| 8,637,509 B2 | 1/2014 | Burgess et al. | |
| 8,765,732 B2 | 7/2014 | Kuntz et al. | |
| 8,846,935 B2 | 9/2014 | Duquenne et al. | |
| 9,018,382 B2 | 4/2015 | Duquenne et al. | |
| 9,090,562 B2 | 7/2015 | Kuntz et al. | |
| 10,987,353 B2 * | 4/2021 | Zhang | A61K 31/5377 |
| 12,036,222 B2 * | 7/2024 | Zhang | A61K 35/00 |
| 2015/0051163 A1 * | 2/2015 | Keilhack | A61K 31/675 514/171 |
| 2016/0361309 A1 | 12/2016 | McCabe et al. | |
| 2019/0134025 A1 | 5/2019 | Zhang et al. | |

FOREIGN PATENT DOCUMENTS

| | | |
|---|---|---|
| WO | 2015128837 A1 | 9/2015 |
| WO | 2017192290 A1 | 11/2017 |

OTHER PUBLICATIONS

Petroni et al. "FISH testing of HER2 immunohistochemistry 1+ invasive breast cancer with unfavorable characteristics," Oncology Letters 12: 3115-3122, 2016 (Year: 2016).*

Karakashev et al. CARM1-expressing ovarian cancer depends on the histone methyltransferase EZH2 activity Nat Commun. Feb. 12, 2018;9(1) (Year: 2018).*

Wang, et al., CARM1 Methylates Chromatin Remodeling Factor BAF155 to Enhance Tumor Progression and Metastasis, Cancer Cell, 2014, 25, pp. 21-36.

Wilson, et al., Epigenetic Antagonism between Polycomb and SWI/SNF Complexes during Oncogenic Transformation, Cancer Cell 2010, 184, 316-328.

Morin et al., Frequent mutation of histone modifying genes in non-Hodgkin lymphoma, Nature 2011, 476, 298-303.

Ryan et al., EZH2 Codon 641 Mutations are Common in BCL2-Rearranged Germinal Center B Cell Lymphomas, PLoS ONE 2011, 6, e28585.

Morin et al., Somatic mutation of EZH2 (Y641) in Follicular and Diffuse Large B-cell Lymphomas of Germinal Center Origin, Nature Genet. 2010, 42, 181-185.

Côté, Targeting of cancer stem cells by inhibitors of DNA and histone methylation, Expert Opin. Investig. Drugs 2015, 24, 1031-43.

Melnick, Epigenetic Therapy Leaps Ahead with Specific Targeting of EZH2, Cancer Cell 2012, 22, 569-70.

Knutson et al., Selective Inhibition of EZH2 by EPZ-6438 Leads to Potent Antitumor Activity in EZH2-Mutant Non-Hodgkin Lymphoma, Mol. Cancer. Ther. 2014, 13, 842-854.

Mullany et al., Minireview: Animal Models and Mechanisms of Ovarian Cancer Development, Endocrinology 2012, 153, 1585-92.

Fong et al., Ovarian cancer mouse models: a summary of current models and their limitations, J. Ovarian Res. 2009, 2, 12.

Herreros-Villanueva et al., Mouse models of pancreatic cancer, World J. Gastroenterol. 2012, 18, 1286-1294.

Fantozzi, Mouse models of breast cancer metastasis, Breast Cancer Res. 2006, 8, 212.

Damsky et al., Mouse melanoma models and cell lines, Pigment Cell & Melanoma Res. 2010, 23, 853-859.

Meuwissen et al., Mouse models for human lung cancer, Genes & Development, 2005, 19, 643-664.

Kim, Animal Models of Cancer in the Head and Neck Region, Clin. Exp. Otorhinolaryngol. 2009, 2, 55-60.

Sano, Xenograft models of head and neck cancers, Head Neck Oncol. 2009, 1, 32.

Illidge, et al., Cancer Biother. & Radiopharm. 2000, 15, 571-80.

Timmerman et al., Idiotype-encoding recombinant adenoviruses provide protective immunity against murine B-cell lymphomas, Blood 2001, 97, 1370-77.

Penichet et al.,A murine B cell lymphoma expressing human HER2/neu undergoes spontaneous tumor regression and elicits antitumor immunity, Cancer Immunolog. Immunother. 2000, 49, 649-662.

Dutt et al., CD8+CD44hi but not CD4+ CD44hi Memory T cells Mediate Potent Graft Antilymphoma Activity without GVHD, Blood 2011, 117, 3230-29.

Qi et al., Selective inhibition of Ezh2 by a small molecule inhibitor blocks tumor cells proliferation, Proc. Natl. Acad. Sci. USA 2012, 109, 21360-65.

Maguire et al., J. Org. Chem. 1990, 55, 948.

Zheng, et al., J. Am. Chem. Soc. 2012, 134, 18004-14.

Kelland, Nature Rev. Cancer 2007, 7, 573-84.

Wheate, et al., Dalton Trans. 2010, 39, 8113-27.

Alberts et al., In vitro phase II comparison of the cytotoxicity of a novel platinum analog, nedaplatin (254-S), with that of cisplatin and carboplatin against fresh, human ovarian cancers, Cancer Chemother. Pharmacol. 1997, 39, 493-497.

Wang et al., Arginine methylation of MDH1 by CARM1 inhibits Glutamine Metabolism and Suppress Pancreatic Cancer, Mol Cell. Nov. 17, 2016;64(4):673-687. doi: 10.1016/j.molcel.2016.09.028.

Yadav et al., Specific protein methylation defects and gene expression perturbations in coactivator-associated arginine methyltransferase 1-deficient mice, Proc Natl Acad Sci U S A. May 27, 2003;100(11):6464-8.

Stathopoulos et al., Comparison of liposomal cisplatin versus cisplatin in non-squamous cell non-small-cell lung cancer, Cancer Chemtherapy & Pharmacol. 2011, 68, 945-950.

Shalem et al., Genome-Scale CRISPR-Cas9 Knockout Screening in Human Cells, Science (2014) 343:84-7.

Bitler et al., Targeting EZH2 methyltransferase activity in ARID1A mutated cancer cells is synthetic lethal, Nature Medicine (2015) 21:231-8.

Aird et al., Suppression of Nucleotide Metabolism Underlies the Establishment and Maintenance of Oncogene-Induced Senescence, Cell Reports (2013) 3:1252-65.

Li et al., Enhancer of zeste homolog 2 (EZH2) promotes the proliferation and invasion of epithelial ovarian cancer cells, MCR (2010) 8:1610-8.

Ye et al., Definition of pRB- and p53-Dependent and -Independent Steps in HIRA/ASF1a-Mediated Formation of Senescence-Associated Heterochromatin Foci, Mol. Cell Biol. (2007) 27:2452-65.

Apps et al., The state-of-play and future of platinum drugs, Endocrine-Related Cancer 2015, 22, 219-233.

Bitler et al., Wnt5a Suppresses Epithelial Ovarian Cancer by Promoting Cellular Senescence, Cancer Research (2011) 71:6184-94.

Tu et al., Oncogenic Ras Regulates BRIP1 Expression to Induce Dissociation of BRCA1 from Chromatin, Inhibit DNA Repair, and Promote Senescence, Developmental Cell (2011) 21:1077-91.

Langmead et al., Fast gapped-read alignment with Bowtie 2, Nat Methods (2012) 9:357-9).

Langmead et al., Ultrafast and memory-efficient alignment of short DNA sequences to the human genome, Genome Biol. (2009) 10:R25.

Heinz et al., Simple Combinations of Lineage-Determining Transcription Factors Prime cis-Regulatory Elements Required for Macrophage and B Cell Identities, Mol Cell (2010) 38:576-89.

Mok et al., A Gene Signature Predictive for Outcome in Advanced Ovarian Cancer Identifies a Survival Factor: Microfibril-Associated Glycoprotein 2, Cancer Cell (2009) 16:521-532.

Bowtell et al., Rethinking ovarian cancer II: reducing mortality from high-grade serous ovarian cancer, Nat Rev Cancer (2015) 15:668-79.

Dubeau et al., Coming into focus: the nonovarian origins of ovarian cancer, Ann Oncol. (2013) 24 Suppl 8, viii28-viii35.

Tone et al., Gene Expression Profiles of Luteal Phase Fallopian Tube Epithelium from BRCAMutation Carriers Resemble High-Grade Serous Carcinoma, Clin Cancer Res. (2008) 14:4067-78.

(56) References Cited

OTHER PUBLICATIONS

Cancer Genome Atlas Research, Integrated Genomic Analyses of Ovarian Carcinoma, Nature (2011) 474:609-15.
Yang et al., Protein arginine methyltransferases and cancer, Nat Rev Cancer (2013) 13:37-50.
McCabe et al. Nature (2012) 492:108-12.
Konze et al., An Orally Bioavailable Chemical Probe of the Lysine Methyltransferases EZH2 and EZH1, ACS Chem Biol. (2013) 8: 1324-34.
He et al., Disabled-2 Exerts Its Tumor Suppressor Activity by Uncoupling c-Fos Expression and MAP Kinase Activation, J Biol Chem. (2001) 276:26814-8.
Barras et al., Cancer Metastasis Rev. (2014) 33:87-100.
Ploner et al., Noxa: at the tip of the balance between life and death, Oncogene (2008) 27 Suppl 1: S84-92).
Kadoch et al., Mammalian SWI/SNF chromatin remodeling complexes and cancer: Mechanistic Insights Gained from Human Genomics, Sci Adv. (2015) 1: e1500447.
Vu, LP et al. PRMT4 Blocks Myeloid Differntiation by Assembling a Methyl-RUNX1-Dependendnt Repressor Complex, Cell Reports 5(6), pp. 1625-1638, 2013.
Li, H et al. Enhancer of Zeste Homolog 2 (EZH2) Promotes the Proliferation and Invastion of Epithelial Ovarian Cancer Cells, Molecular Cancer Research 8(12), pp. 1610-1618, 2010.
International Search Report, issued in corresponding International Patent Application No. PCT/US2017/029170, dated Jul. 17, 2017.
National Center for Biotechnology Information. PubChem Database. CPI-1205, Source=IUPHAR/BPS Guide to Pharmacology, SID=315661200, https://pubchem.ncbi.nlm.nih.gov/substance/315661200.

* cited by examiner

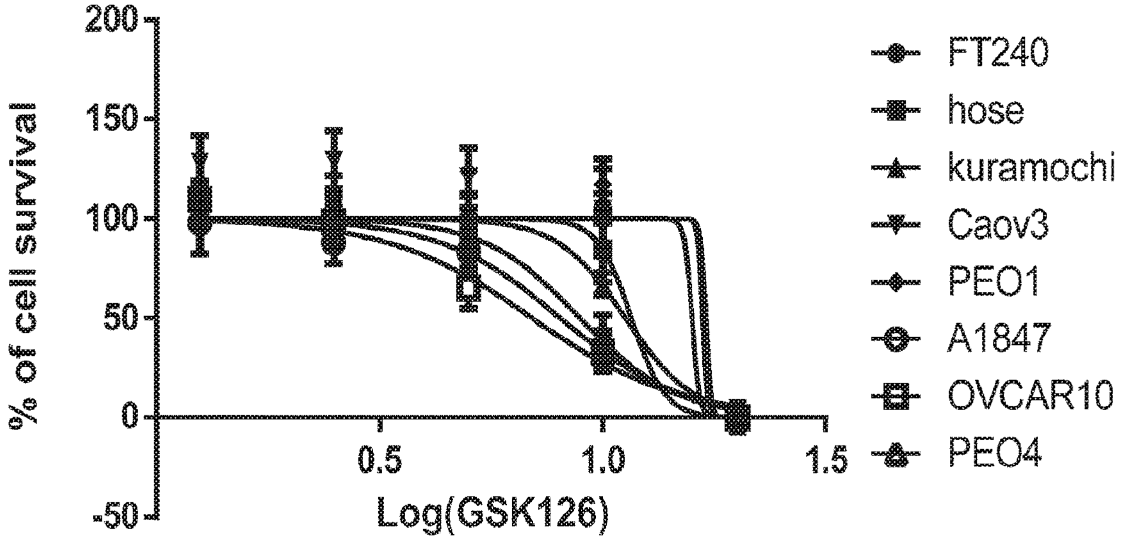
FIG. 7
| | FT240 | hose | kuramochi | Caov3 | PEO1 | A1847 | OVCAR10 | PEO4 |
|---|---|---|---|---|---|---|---|---|
| IC50 | 16.73 | 11.59 | 11.25 | 16.99 | 15.83 | 8.048 | 6.956 | 8.905 |
FIG. 8
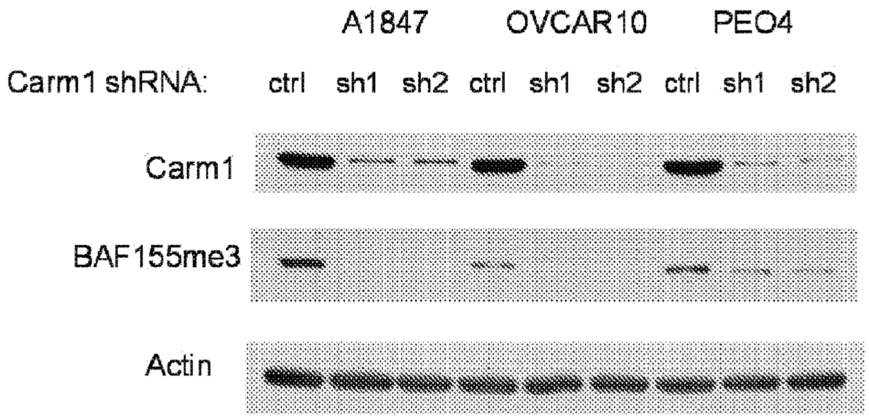
FIG. 9

Supplementary Table 1. EZH2 inhibitors are selective against CARM1 expression

| Compound | Target | Dose, μM | CARM1 High Parental A1847 Relative Growth | CARM1 High Parental A1847 S.E.M. | CARM1 Knockout Relative Growth | CARM1 Knockout S.E.M. | *P*-value |
|---|---|---|---|---|---|---|---|
| A366 | G9a, GLP | 20 | 1.12610177 | 0.026994901 | 1.083216187 | 0.024462549 | 0.284100154 |
| Bromosporine | pan-Bromodomain | 20 | 0.00076137 | 0.00076137 | 0.013530824 | 0.011493706 | 0.347865117 |
| C1994 | CREBBP/EP300 | 3.6 | 0.00010305 | 0.000103051 | 0.031107943 | 0.014268088 | 0.118116966 |
| C646 | CREBBP, EP300 | 0.8 | 0.92105820 | 0.01489038 | 1.102442703 | 0.013846102 | 0.000113966 |
| CBP112 | CREBBP, EP300 | 7.8 | 0.94978798 | 0.026387138 | 0.65895342 | 0.209455497 | 0.259485988 |
| CBP30 | HDAC1 | 20 | 0.99663221 | 0.018982712 | 0.54380163 | 0.040955842 | 0.000416278 |
| DMSO | LSD1 | 20 | 0.98728639 | 0.006584402 | 1.007863957 | 0.034432096 | 0.595855393 |
| GSK/LSD1 | Control | 0 | 0.95170977 | 0.023908506 | 1.062526654 | 0.030591842 | 0.030917171 |
| **GSK126** | **EZH2** | **10** | **0.15651653** | **0.080547528** | **0.532314948** | **0.051413606** | **0.010631224** |
| GSK2901 | BAZ2A, BAZ2B | 0.4 | 0.89260249 | 0.018578154 | 1.170477089 | 0.021930676 | 8.23709E-05 |
| GSKJ4 | JMJD3, UTX | 0.61 | 1.16061609 | 0.018984972 | 1.063614933 | 0.008768788 | 0.008546659 |
| IOX1 | pan-2-OG | 16 | 0.03557553 | 0.010172418 | 0.281729478 | 0.034844998 | 0.003916368 |
| IOX2 | PHD2 | 0.03 | 1.05962417 | 0.028477162 | 1.020770482 | 0.035433688 | 0.426973425 |
| JQ1 | BRD2, BRD3, BRD4, BRDT (BET) | 20 | 0.00115055 | 0.000340774 | 0.007319818 | 0.004529224 | 0.26655804 |
| LAQ824 | HDACs | 0.02 | 0.00009757 | 9.75693E-05 | 0.004824201 | 0.001825039 | 0.080873167 |
| LLY-507 | SMYD2 | 2.7 | 1.04802932 | 0.029072456 | 0.856154144 | 0.023618675 | 0.002454216 |
| Olaparib | PARP | 0.7 | 0.01828986 | 0.014278756 | 0.02455379 | 0.008317064 | 0.720739487 |
| PFI-1 | BRD2, BRD3, BRD4, BRDT (BET) | 0.8 | 0.19467600 | 0.021110016 | 0.013219267 | 0.012196005 | 0.000821766 |
| PFI-2 | SETD7 | 20 | 0.95709362 | 0.028031604 | 1.0820438 | 0.045106733 | 0.065165254 |
| PFI-3 | SMARCA,PB1 | 20 | 0.90866744 | 0.030985436 | 1.104246892 | 0.011560561 | 0.004730005 |
| UNC0638 | G9a, GLP | 20 | 0.08062460 | 0.011946064 | 0.047423828 | 0.016990494 | 0.166662741 |
| UNC0642 | G9a, GLP | 8 | 0.24296953 | 0.039794339 | 0.015929696 | 0.009532955 | 0.008612528 |
| UNC1215 | HDAC6, HDAC2, HDAC3, HDAC8 | 20 | 0.92996441 | 0.039479602 | 1.046045711 | 0.031762606 | 0.063852099 |
| **UNC1999** | **EZH2** | **0.48** | **0.56224648** | **0.058501852** | **0.761331101** | **0.037563764** | **0.034353525** |

FIG. 27

| Pathway/Function | *P* value | Number of Genes |
|---|---|---|
| Apoptosis | $2.6 \times 10^{-6}$ | 19 (e.g. *DAB2*, *DLC1*, *NOXA*) |

| Upstream transcription regulator | $P$-value | Number of genes |
|---|---|---|
| SMARCA4 (SWI/SNF) | 1.22 X 10$^{-30}$ | 175 |

| | Correlation between with CARM1 expression in TCGA samples | | | |
|---|---|---|---|---|
| | Pearson Correlation | | Spearman Correlation | |
| Gene | R value | p-value | R value | p-value |
| MAP3K5 | -0.198965049 | **4.08177E-06** | -0.217951734 | **4.25453E-07** |
| PMAIP1 | -0.175084537 | **5.23484E-05** | -0.175419055 | **5.06219E-05** |
| TGFBI | -0.156839732 | **0.000297147** | -0.14902825 | **0.000591471** |
| DAB2 | -0.13373293 | **0.002073418** | -0.147861187 | **0.000653711** |
| ITGA4 | -0.139887941 | **0.001270235** | -0.142587487 | **0.001018204** |
| RND3 | -0.167642586 | **0.000108644** | -0.140071566 | **0.00125142** |
| PPARGC1A | -0.116077901 | **0.007585654** | -0.139752622 | **0.001284266** |
| DLC1 | -0.140648915 | **0.001193924** | -0.133147796 | **0.002170058** |
| PDE4B | -0.092141219 | **0.034282702** | -0.130370969 | **0.002687269** |
| FMN2 | -0.12600036 | **0.003731964** | -0.121151589 | **0.005311183** |
| MME | -0.104759346 | **0.016035316** | -0.111333348 | **0.010462821** |
| TNC | -0.110565685 | **0.011009917** | -0.106999047 | **0.013897985** |
| KLF5 | -0.11041769 | **0.011118258** | -0.104742287 | **0.016052644** |
| EPHA4 | -0.086673905 | **0.046520259** | -0.100322606 | **0.021133339** |
| ANTXR1 | -0.094541709 | **0.02984649** | -0.099743744 | **0.021892744** |
| FN1 | -0.116142316 | **0.007552021** | -0.099172431 | **0.022665348** |
| ANTXR2 | -0.091802828 | **0.034951143** | -0.095685501 | **0.027911995** |
| GPR37 | -0.098490018 | **0.023619066** | -0.091042741 | **0.036493133** |
| TGFBR2 | -0.087770064 | **0.043808917** | -0.087845362 | **0.043627654** |

FROM FIG.49

| mRNA expression | | | | | | | ChIP-seq signal intensity | | | |
|---|---|---|---|---|---|---|---|---|---|---|
| Control/CARM1 knockout | | | RNA seq count | | RNA seq FPKM | | Control | | CARM1 knockout | |
| fold change | p-value | fdr | Control | CARM1 knockout | Control | CARM1 knockout | EZH2 | H3K27me3 | EZH2 | H3K27me3 |
| -3.185196512 | 5.45E-09 | 0% | 881 | 4428 | 4.29 | 18.12 | 4.71 | 4.90 | 0.00 | 0.00 |
| -3.382108093 | 3.6E-10 | 0% | 153 | 544 | 1.14 | 3.88 | 3.28 | 4.68 | 0.00 | 0.00 |
| -4.296812722 | 1.3E-16 | 0% | 110 | 465 | 0.75 | 3.04 | 3.01 | 4.41 | 0.00 | 0.00 |
| -3.92934096 | 1.3E-11 | 0% | 106 | 438 | 0.99 | 4.79 | 4.05 | 4.61 | 0.00 | 0.00 |
| -3.184665486 | 5.8E-10 | 0% | 239 | 800 | 3.05 | 8.65 | 3.71 | 3.15 | 0.00 | 0.00 |
| -5.93743752 | 1.4E-22 | 0% | 6 | 50 | 0.17 | 1.7 | 3.33 | 5.90 | 0.00 | 0.00 |
| -23.86194957 | 1.5E-06 | 0% | 1 | 28 | 0.01 | 0.42 | 3.50 | 3.49 | 0.00 | 0.00 |
| -3.555559726 | 7.3E-13 | 0% | 1027 | 3837 | 6.56 | 20.43 | 5.10 | 5.94 | 0.00 | 0.00 |
| -14.31136541 | 3E-16 | 0% | 8 | 122 | 0.16 | 2.37 | 5.40 | 5.45 | 0.00 | 0.00 |
| -4.572896825 | 2.7E-14 | 0% | 115 | 553 | 2.22 | 9.63 | 3.26 | 3.69 | 0.00 | 0.00 |
| -4.366394913 | 2.4E-15 | 0% | 280 | 1285 | 2.76 | 11.66 | 5.14 | 4.79 | 0.00 | 0.00 |
| -12.75997307 | 2.2E-29 | 0% | 619 | 3001 | 3.94 | 17.78 | 4.53 | 3.37 | 0.00 | -3.60 |
| -4.054372234 | 1E-14 | 0% | 541 | 2305 | 8.15 | 37.42 | 3.20 | 5.51 | 0.00 | 0.00 |
| -8.265600453 | 2.3E-20 | 0% | 30 | 261 | 0.33 | 2.76 | 3.59 | 6.07 | 0.00 | 0.00 |
| -4.641694733 | 1.2E-16 | 0% | 299 | 946 | 1.8 | 5.43 | 3.91 | 3.20 | 0.00 | 0.00 |
| -14.58093837 | 2E-45 | 0% | 1 | 19 | 0.04 | 0.71 | 4.65 | 3.78 | 0.00 | 0.00 |
| -3.071935896 | 4.6E-10 | 0% | 6 | 38 | 0.15 | 0.88 | 5.87 | 4.01 | 0.00 | 0.00 |
| -3.051285042 | 0.00013 | 0% | 23 | 74 | 0.26 | 0.81 | 4.40 | 4.40 | 0.00 | 0.00 |
| -3.313985283 | 9.3E-11 | 0% | 294 | 1024 | 2.15 | 7.14 | 5.76 | 3.99 | 0.00 | 0.00 |

FIG. 49 CONTINUED

| Top 10 upstream transcription factors that are enriched by the differentially expressed genes. | | | | |
|---|---|---|---|---|
| Upstream transcription Regulator | p-value of overlap | Number of genes | | |
| SMARCA4 | 1.22E-30 | 175 | | |
| CTNNB1 | 7.00E-28 | 190 | | |
| JUN | 2.71E-18 | 119 | | |
| CREB1 | 5.16E-18 | 140 | | |
| TP53 | 2.94E-17 | 280 | | |
| SOX2 | 6.43E-17 | 94 | | |
| NFKBIA | 5.84E-16 | 115 | | |
| STAT3 | 9.43E-16 | 130 | | |
| NEUROG1 | 9.79E-16 | 35 | | |
| NKX2-3 | 1.44E-15 | 71 | | |

FIG. 51

METHODS OF TREATING CANCERS OVEREXPRESSING CARM1 WITH EZH2 INHIBITORS AND PLATINUM-BASED ANTINEOPLASTIC DRUGS

CROSS-REFERENCE TO RELATED APPLICATIONS

This application is a continuation of U.S. Non-provisional application Ser. No. 16/098,753 filed Nov. 2, 2018, now allowed, which is the national stage entry of International Patent Application No. PCT/US2017/029170, filed Apr. 24, 2017, which in turn claims priority to, and the benefit of, U.S. Provisional Patent Application No. 62/331,792, filed May 4, 2016; U.S. Provisional Patent Application No. 62/331,936, filed May 4, 2016; and U.S. Provisional Patent Application No. 62/366,935, filed Jul. 26, 2016, all of which are incorporated herein by reference in their entireties.

GOVERNMENT SUPPORT

This invention was made with Government support under NIH Grant Nos. CA010815 and 5 R01 CA163377-04, awarded by the National Institutes of Health. The government has certain rights in the invention.

FIELD OF THE INVENTION

Therapeutic treatments of cancer based on overexpression of the arginine methyltransferase CARM1 gene are disclosed.

BACKGROUND OF THE INVENTION

Epithelial ovarian cancer (EOC) remains the most lethal gynecological malignancy in the United States. Despite the recent advances in targeted therapy in different types of cancer, platinum based therapies such as cisplatin remain the standard of care for EOC patients. Recent discoveries have demonstrated that ovarian cancer is composed of multiple separate diseases. High-grade serous ovarian cancer (HGSOC) is the most common subtype (>70% of EOC cases) and accounts for the majority of EOC-associated mortalities. Although many patients initially respond to cisplatin, the majority of these patients become resistant and the mechanism of this resistance is not fully understood. Epigenetic regulation has been shown to play an important role in tumor progression and specifically in the development of platinum therapy resistance. Thus, it is important to identify epigenetic factors that are responsible for cisplatin resistance in EOC.

SWI/SNF (Switch/Sucrose Non-Fermentable) is a chromatin remodeling complex that is often dysregulated in different types of cancer. The activity of the SWI/SNF complex is tightly regulated and multiple subunits of SWI/SNF are post-translationally modified. BAF155, one of the subunits of SWI/SNF complex, is methylated by coactivator-associated arginine methyltransferase 1 (CARM1), also known as protein arginine methyltransferase 4 (PRMT4). This modification has been shown to enhance tumor progression and metastasis. Wang, et al., *Cancer Cell*, 2014, 25, 21-36. CARM1 has been shown to methylate substrates involved in epigenetic chromatin remodeling. This suggests that epigenetic mechanisms play a key role in CARM1-expressing cancers. Interestingly, the CARM1 gene is amplified in 10% of high-grade ovarian cancer patients and CARM1 amplification is associated with poor prognosis in EOC patients.

Polycomb-repressive complex 2 (PRC2) is a multiprotein complex that negatively regulates the expression of large numbers of genes by generating a silencing histone modification (H3K27me3) through its catalytic subunit enhancer of zeste homolog 2 (EZH2). Many of the genes regulated by PRC2 are involved in cancer progression, and dysregulation of PRC2 function is observed in many different types of cancer including EOC. Recent studies have shown that SWI/SNF and PRC2 complexes play an antagonistic role in tumorigenesis. Wilson, et al., Cancer Cell 2010, 184, 316 328. EZH2 is highly expressed in many cancers, including breast cancer, prostate cancer, and lymphoma, and is frequently associated with tumor progression and poor outcomes. Furthermore, mutated forms of EZH2, including somatic heterozygous mutations of the Y641 and A677 residues of the catalytic SET domain, are observed in some cancers including diffuse large B-cell lymphoma (DLBCL) and follicular lymphoma. Morin, et al., *Nature* 2011, 476, 298-303; Ryan, et al. *PLoS ONE* 2011, 6, e28585; Morin, et al., *Nature Genet.* 2010, 42, 181-185.

A number of selective small molecule EZH2 inhibitors have been identified and progressed into clinical development. Momparler and Côté, *Expert Opin. Investig. Drugs* 2015, 24, 1031-43; Melnick, *Cancer Cell* 2012, 22, 569-70. EZH2 inhibitors are currently being investigated for the treatment of cancers exhibiting overexpression of EZH2, including B cell lymphomas such as DLBCL, Germinal center B-cell DLBCL (GCB-DLBCL), and non-Hodgkin's lymphoma, follicular lymphoma, multiple myeloma, INI1-negative tumors, synovial sarcoma, breast cancer, prostate cancer, and other solid tumors. For example, the EZH2 inhibitor tazemetostat (EPZ-6438) has potent activity against EZH2-mutated non-Hodgkin's lymphoma. Knutson, et al., *Mol. Cancer. Ther.* 2014, 13, 842-854.

The present invention provides the unexpected finding that EZH2 inhibitors may be used to effectively treat cancers that overexpress CARM1. The present invention further provides the unexpected finding that combinations of EZH2 inhibitors and platinum-based antineoplastic agents are surprisingly effective in the treatment of any of several subtypes of cancers, such as solid tumor cancers, wherein a biological sample exhibits CARM1 overexpression.

SUMMARY OF THE INVENTION

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the cancer is ovarian cancer.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the cancer is epithelial ovarian cancer.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the cancer is an epithelial ovarian tumor.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the cancer is malignant ovarian cancer.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the EZH2 inhibitor is selected from the group consisting of(S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide (GSK 126):

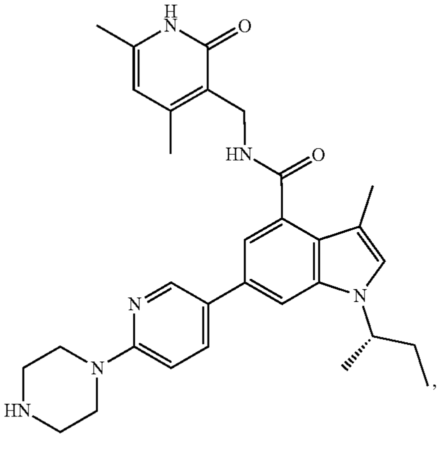 [SMILES: CC[C@H](C)n1cc(C)c2c(C(=O)NCc3c(C)cc(C)[nH]c3=O)cc(-c3ccc(N4CCNCC4)nc3)cc21]

tazemetostat:

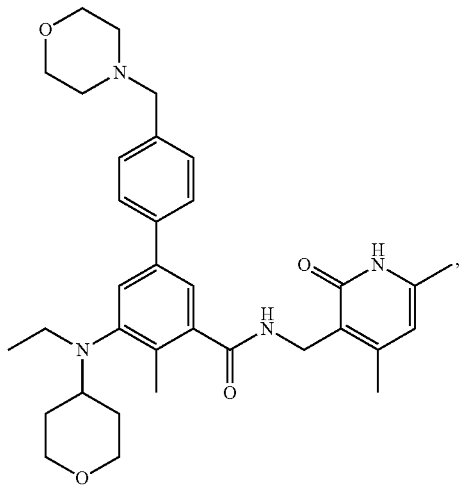 [SMILES: CCN(c1cc(-c2ccc(CN3CCOCC3)cc2)cc(C(=O)NCc2c(C)cc(C)[nH]c2=O)c1C)C1CCOCC1]

(R,Z)-1-(1-(1-(ethylsulfonyl)piperidin-4-yl)ethyl)-N-((2-hydroxy-4-methoxy-6-methylpyridin-3-yl)methyl)-2-methyl-1H-indole-3-carbimidic acid (CPI-169):

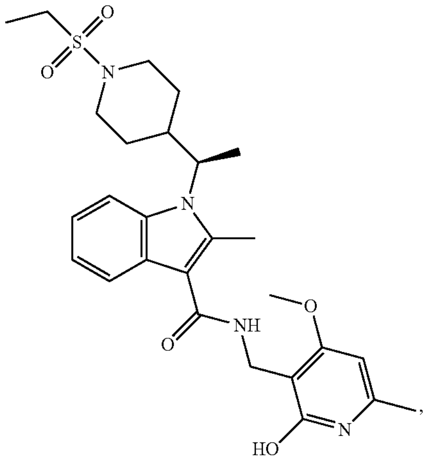 [SMILES: CCS(=O)(=O)N1CCC([C@@H](C)n2c(C)c(C(=O)NCc3c(OC)cc(C)nc3O)c3ccccc32)CC1]

1-cyclopentyl-N-((4,6-dimethyl-2-oxo-1,2-dihydropyridin-3-yl)methyl)-6-(4-(morpholinomethyl)phenyl)-1H-indazole-4-carboxamide (EPZ-5687):

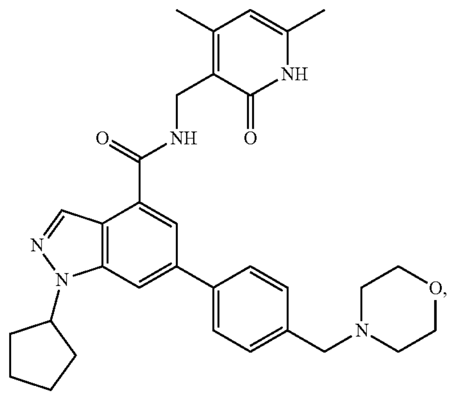 [SMILES: Cc1cc(C)c(CNC(=O)c2cc(-c3ccc(CN4CCOCC4)cc3)cc3c2cnn3C2CCCC2)c(=O)[nH]1]

N-((4,6-dimethyl-2-oxo-1,2-dihydropyridin-3-yl)methyl)-3-(ethyl((1R,4R)-4-((2-methoxyethyl)(methyl)amino)cyclohexyl)amino)-2-methyl-5-(3-morpholinoprop-1-yn-1-yl)benzamide (EPZ-11989):

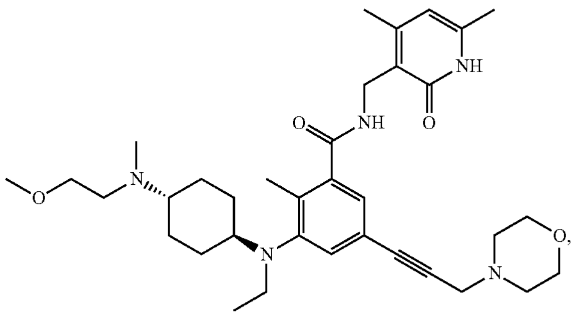 [SMILES: CCN(c1cc(C#CCN2CCOCC2)cc(C(=O)NCc2c(C)cc(C)[nH]c2=O)c1C)[C@H]1CC[C@H](N(C)CCOC)CC1]

1-isopropyl-N-((6-methyl-2-oxo-4-propyl-1,2-dihydropyridin-3-yl)methyl)-6-(2-(4-methylpiperazin-1-yl)pyridin-4-yl)-1H-indazole-4-carboxamide (GSK343):

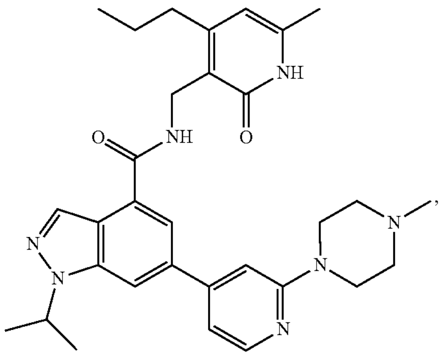 [SMILES: CCCc1cc(C)[nH]c(=O)c1CNC(=O)c1cc(-c2ccnc(N3CCN(C)CC3)c2)cc2c1cnn2C(C)C]

N-((4,6-dimethyl-2-oxo-1,2-dihydropyridin-3-yl)methyl)-1-isopropyl-3-methyl-6-(6-(4-methylpiperazin-1-yl)pyridin-3-yl)-1H-indole-4-carboxamide (GSK503):

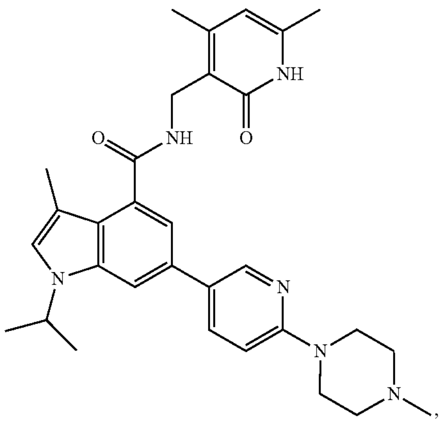 [SMILES: Cc1cc(C)c(CNC(=O)c2cc(-c3ccc(N4CCN(C)CC4)nc3)cc3c2c(C)cn3C(C)C)c(=O)[nH]1]

1-isopropyl-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide (UNC-1999):

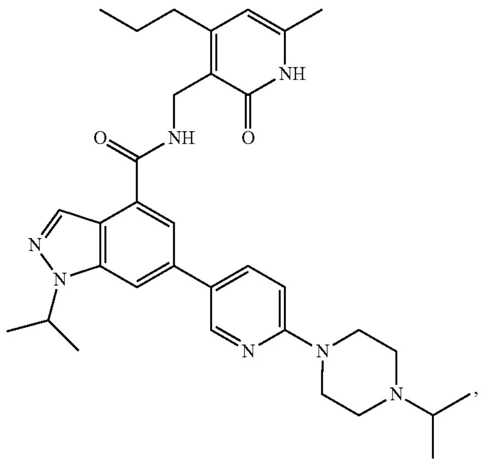 [SMILES: CCCc1cc(C)[nH]c(=O)c1CNC(=O)c1cc(-c2ccc(N3CCN(C(C)C)CC3)nc2)cc2c1cnn2C(C)C]

6-cyano-N-((4,6-dimethyl-2-oxo-1,2-dihydropyridin-3-yl)methyl)-1-(pentan-3-yl)-1H-indole-4-carboxamide (E11):

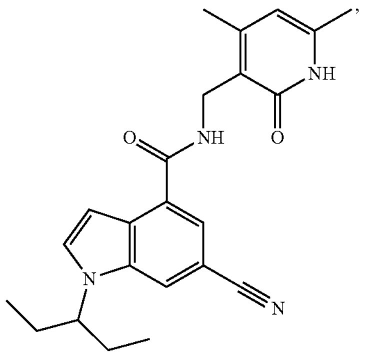 [SMILES: CCC(CC)n1ccc2c(C(=O)NCc3c(C)cc(C)[nH]c3=O)cc(C#N)cc21]

(1S,2R,5R)-5-(4-amino-1H-imidazo[4,5-c]pyridin-1-yl)-3-(hydroxymethyl)-3-cyclopentene-1,2-diol (DZNep):

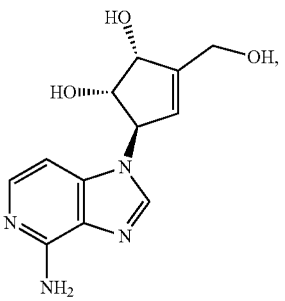 [SMILES: Nc1nccc2c1ncn2[C@@H]1C=C(CO)[C@@H](O)[C@H]1O]

sinefungin:

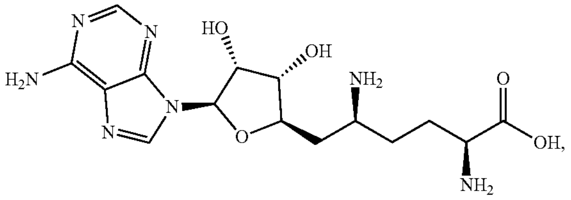 [SMILES: Nc1ncnc2c1ncn2[C@@H]1O[C@H](C[C@@H](N)CC[C@H](N)C(=O)O)[C@@H](O)[C@H]1O]

and pharmaceutically acceptable salts, solvates, hydrates, cocrystals, or prodrugs thereof.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, wherein the overexpression of arginine methyltransferase CARM1 is at a level selected from the group of at least 2%, at least 5%, at least 8%, at least 10%, and at least 15% relative to a level in normal epithelial cells.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, and further comprising the step of administering a therapeutically effective dose of a platinum drug to the human subject.

In an embodiment, the invention includes a method of treating a cancer in a human subject suffering from the cancer in which cancer cells overexpress arginine methyltransferase CARM1, the method comprising the step of administering a therapeutically effective dose of an EZH2 inhibitor to the human subject, and further comprising the step of administering a therapeutically effective dose of a platinum drug to the human subject, wherein the platinum drug is selected from the group consisting of cisplatin, carboplatin, oxaliplatin, satraplatin, picoplatin, nedaplatin, triplatin tetranitrate, lipoplatin (liposomal cisplatin), and pharmaceutically acceptable salts, solvates, hydrates, cocrystals, or prodrugs thereof.

In an embodiment, the invention includes a pharmaceutical composition for treating a cancer in a human subject suffering from the cancer in which cancer cells overexpress arginine methyl transferase CARM1, the pharmaceutical composition including a therapeutically effective amount of an enhancer of zeste homolog 2 (EZH2) inhibitor or a pharmaceutically acceptable salt, solvate, hydrate, cocrystal, or prodrug thereof, and a pharmaceutically acceptable carrier. In some embodiments, the pharmaceutical composition includes a therapeutically effective amount of a platinum drug or a pharmaceutically acceptable salt, solvate, hydrate, cocrystal, or prodrug thereof.

BRIEF DESCRIPTION OF THE DRAWINGS

The foregoing summary, as well as the following detailed description of the invention, will be better understood when read in conjunction with the appended drawings.

FIG. 7 illustrates GSK 126 response curves in a panel of normal and ovarian cancer cell lines. Error bars indicate standard error (S.E.) for n=3. *, p≤0.05.

FIG. 8 illustrates $IC_{50}$ results for the panel of normal and ovarian cancer cell lines.

FIG. 9 illustrates a Western blot of CARM1 and BAF155me2 in CARM1 depleted cells with a control (Actin).

FIG. 27 illustrates a table of EZH2 inhibitors that are selective against CARM1 expression. CARM1-high parental controls and CARM1 knockout A1847 cells were treated with the indicated concentration of the small molecules in a 14-day colony formation assay. Integrated density for each well was calculated using NIH Image J software. The relative growth of the indicated cells was determined by normalizing to the vehicle control treated cells. n=4 and p-value was calculated using a two-tailed t-test.

FIGS. 46 and 47 illustrate ChIP-seq peaks compilations of EZH2 (FIG. 46) and H3K27Me3 (FIG. 47) relative to transcription starting site (TSS) of the 218 direct EZH2/H3K27Me3 target genes that are upregulated in CARM1 knockout cells compared with control CARM1-high A1847 cells. FIG. 48 illustrates that EZH2/H3K27Me3 direct target genes are enriched in genes upregulated by CARM1 knockout.

FIG. 49 illustrates a table that lists 19 identified EZH2/H3K27Me3 target apoptosis-promoting genes that are upregulated by CARM1 knockout and negatively correlate with CARM1 expression in the 579 TCGA high grade serous ovarian carcinoma database.

FIG. 51 illustrates a table that lists the top 10 upstream transcription factors that are enriched by the differentially expressed genes in control parental and CARM1 knockout A1847 cells determined by Ingenuity Pathway Analysis.

FIG. 53 illustrates that the indicated CARM1-high cells were infected with the indicated shCARM1 or controls. Expression of CARM1 and BAF155Me levels and loading control (β-actin) was determined by immunoblot. FIG. 54 illustrates that the indicated cells were treated with 10 μM GSK126 or vehicle control for 7 days. Expression of BAF155 and a loading control (β-actin) was determined by immunoblot.

FIG. 67 illustrates CARM1-expressing A1847 cells that were infected with a lentivirus encoding shBAF155 targeting the 3' untranslated region (UTR) of the human BAF155 gene together with a retrovirus encoding wild-type BAF155 (WT) or a BAF155 R1064K mutant. Expression of BAF155 and BAF155Me was determined by immunoblot. β-actin expression was used as a loading control. FIG. 68 illustrates the expression of the indicated BAF155/EZH2 target genes by qRT-PCT. FIGS. 69 to 71 illustrate the results of a ChIP analysis using anti-EZH2 (FIG. 69), anti-H3K27Me3 (FIG. 70), or anti-BAF155 (FIG. 71) antibodies, where isotype-matched IgG was used as a negative control. ChIP products were subjected to qPCR analysis using primers specific for the promoter regions of the human DAB2, DLC1, and NOXA genes. Error bars represent SEM. P-values are from a two-tailed t-test.

FIG. 72A illustrates the expression of the BAF155Me target gene TIMP3. CARM1-expressing A1847 cells were infected with a lentivirus encoding shBAF155 targeting the 3' untranslated region (UTR) of the human BAF155 gene together with a retrovirus encoding wild-type BAF155 (WT) or a BAF155 R1064K mutant. Expression of BAF155Me target gene TIMP3 was determined by qRT-PCR in the indicated cells. Mean of three independent experiments with SEM. *$p<0.001$. FIG. 72B illustrates the results of a ChIP analysis using an anti-BAF155 antibody in CARM1-expressing A1847 cells. An isotype matched IgG was used as a negative control. ChIP products were subjected to qPCR analysis using primers specific for the promoter of the human TIMP3 gene. Error bars represent SEM. *$p<0.001$.

FIG. 73 illustrates images of tumors dissected from control or GSK126 treated mice. CARM1-high A1847 cells were injected subcutaneously into immunocompromised NSG mice (n=5/group). Tumors were allowed to establish for one week before the mice were randomized into two different treatment groups. Mice were treated with vehicle control or GSK126 (50 mg/kg daily) for an additional three weeks. At the end of treatment, the mice were euthanized. Bar=1 cm. FIG. 74 illustrates a difference in tumor size measured as a surrogate for tumor burden from the control and GSK 126 treated mice at the indicated time point. FIG. 75 illustrates a difference in tumor weight measured as a surrogate for tumor burden from control and GSK 126-treated mice. The mice were injected with CARM1 knockout A1847 cells.

DETAILED DESCRIPTION OF THE INVENTION

Figure 1:
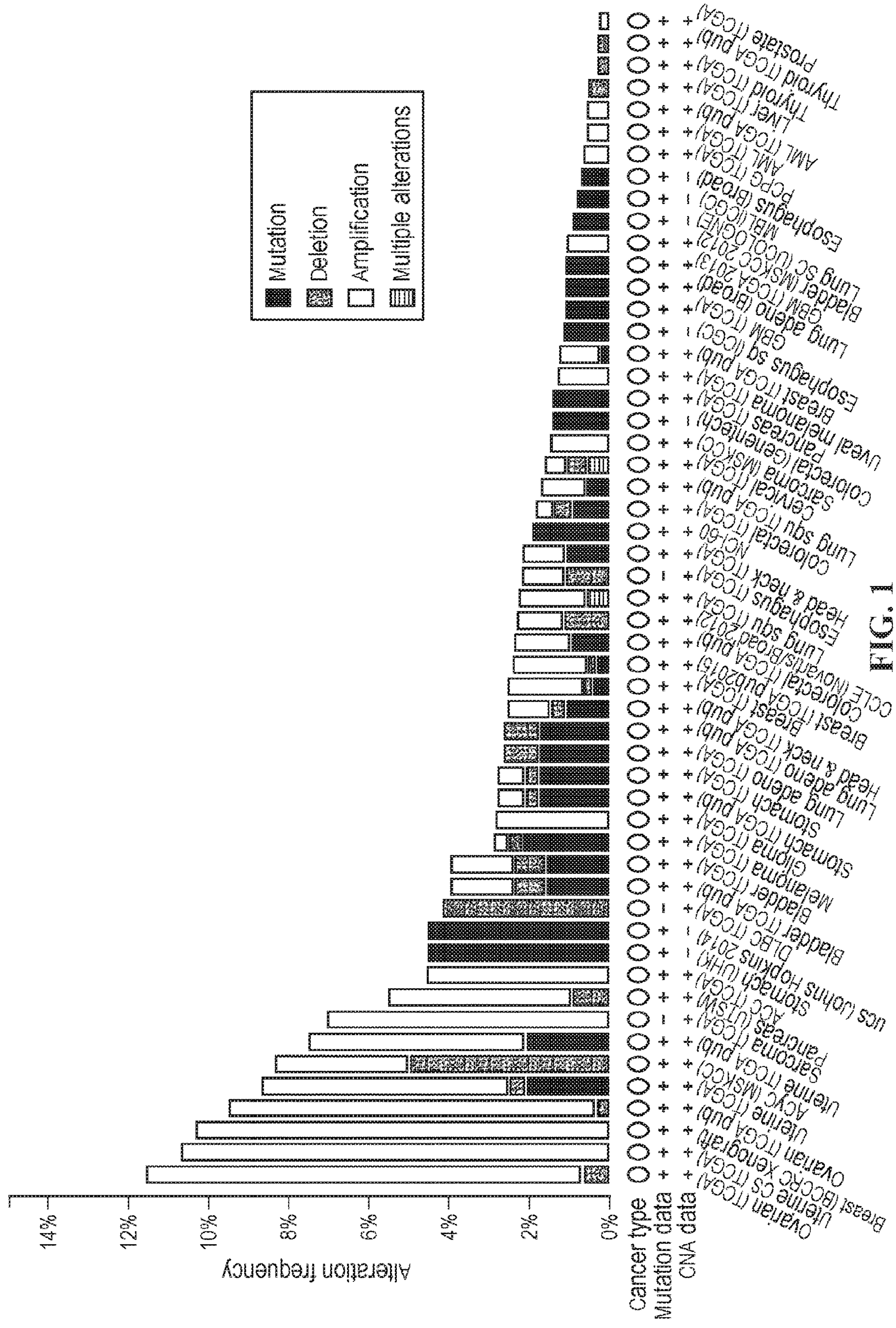
FIG. 1 illustrates CARM1 expression in different types of cancer.

Unless defined otherwise, all technical and scientific terms used herein have the same meaning as is commonly understood by one of skill in the art to which this invention belongs. All patents and publications referred to herein are incorporated by reference in their entireties.

Definitions

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The terms "active pharmaceutical ingredient" and "drug" include EZH2 inhibitors and platinum-based antineoplastic drugs.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, *Design of Prodrugs*, Elsevier, Amsterdam, 1985). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, cither in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$- or $^{14}C$-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds used in the methods of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In selected embodiments, the cancer is selected from the group consisting of ovarian cancer, epithelial ovarian cancer, non-Hodgkin's lymphomas (such as diffuse large B-cell lymphoma), acute myeloid leukemia, thymus cancer, brain cancer, lung cancer, squamous cell cancer, skin cancer, eye cancer, retinoblastoma, intraocular melanoma, oral cavity and oropharyngeal cancer, bladder cancer, gastric cancer, stomach cancer, pancreatic cancer, breast cancer, cervical cancer, head and neck cancer, renal cancer, kidney cancer, liver cancer, prostate, colorectal cancer, bone (e.g., metastatic bone), esophageal cancer, testicular cancer, gynecological cancer, thyroid cancer, central nervous system lymphomas, AIDS-related cancers (e.g. lymphoma and Kaposi's sarcoma), viral-induced cancers such as cervical carcinoma (human papillomavirus), B-cell lymphoproliferative disease and nasopharyngeal carcinoma (Epstein-Barr virus), Kaposi's sarcoma and primary effusion lymphomas, hepatocellular carcinoma (hepatitis B and hepatitis C viruses), and T-cell leukemias (human T-cell leukemia virus-1), B cell acute lymphoblastic leukemia, Burkitt's leukemia, juvenile myelomonocytic leukemia, hairy cell leukemia, Hodgkin's disease, multiple myeloma, mast cell leukemia, and mastocytosis.

In an embodiment, the hyperproliferative disorder is EZH2-mutated cancer. EZH2-mutated cancers are described, e.g., in International Patent Application Publication No. WO 2015/128837 A1 and U.S. Patent Application Publication No. 2016/0361309, the disclosures of which are incorporated by reference herein. EZH2-mutated cancers include point mutations, such as the alanine-to-valine mutation at residue 687 of EZH2 (the A687V mutation).

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32. Models for determining efficacy in B cell lymphomas, such as diffuse large B cell lymphoma (DLBCL), include the PiBCL1 murine model with BALB/c (haplotype H-2d) mice. Illidge, et al., *Cancer Biother. & Radiopharm.* 2000, 15, 571-80. Efficacy of treatments for Non-Hodgkin's lymphoma may be assessed using the 38C13 murine model with C3H/HeN (haplotype 2-Hk) mice or alternatively the 38C13 Her2/neu model. Timmerman, et al., Blood 2001, 97, 1370-77; Penichet, et al., *Cancer Immunolog. Immunother.* 2000, 49, 649-662. Efficacy of treatments for chronic lymphocytic leukemia (CLL) may be assessed using the BCL1 model using BALB/c (haplotype H-2d) mice. Dutt, et al., *Blood* 2011, 117, 3230-29.

EZH2 Inhibitors

In an embodiment, the invention includes a method of treating a cancer in a human subject suffering from the cancer in which cancer cells overexpress arginine methyltransferase CARM1, the method comprising the step of administering a therapeutically effective dose of an active pharmaceutical ingredient that is an EZH2 inhibitor to the human subject. In an embodiment, the foregoing method further comprises the step of administering a therapeutically effective dose of another active pharmaceutical ingredient, such as a platinum-based drug. The EZH2 inhibitor may be any EZH2 inhibitor known in the art. Suitable EZH2 inhibitors are described, for example, in Momparler and Côté, *Expert Opin. Investig. Drugs* 2015, 24, 1031-43. In particular, the EZH2 inhibitor is an EZH2 inhibitor described in more detail in the following paragraphs.

In an embodiment, the EZH2 inhibitor is (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide, also known as GSK2816126 or GSK126 (Formula (1)):

Formula (1)

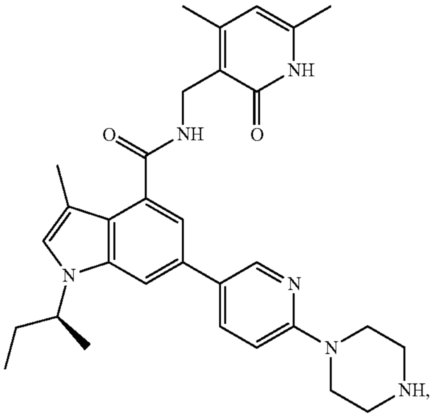

or a pharmaceutically acceptable salt, solvate, hydrate, cocrystal, tautomer, or prodrug thereof. GSK126 is commercially available from multiple suppliers. The synthesis and properties of GSK126 and other suitable EZH2 inhibitors are described in, e.g., U.S. Pat. Nos. 8,536,179, 8,846,935, and 8,637,509, the disclosures of which are incorporated by reference herein.

In an embodiment, the EZH2 inhibitor is N-((4,6-dimethyl-2-oxo-1,2-dihydropyridin-3-yl)methyl)-1-isopropyl-3-methyl-6-(6-(4-methylpiperazin-1-yl)pyridin-3-yl)-1H-indole-4-carboxamide, also known as GSK503 (Formula (2)):

Formula (2)

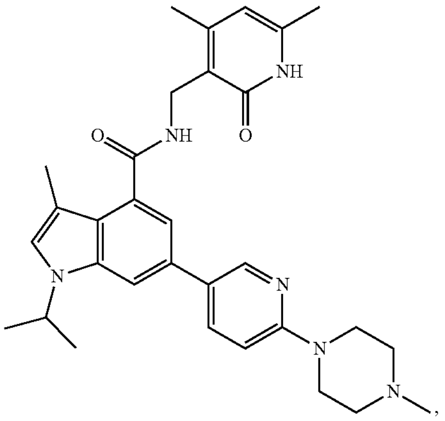

or a pharmaceutically acceptable salt, solvate, hydrate, cocrystal, tautomer, or prodrug thereof. The synthesis and properties of Formula (2) are described in, e.g., U.S. Pat. Nos. 8,536,179, 8,846,935, and 8,637,509, the disclosures of which are incorporated by reference herein.

In an embodiment, the EZH2 inhibitor is 1-isopropyl-N-((6-methyl-2-oxo-4-propyl-1,2-dihydropyridin-3-yl)methyl)-6-(2-(4-methylpiperazin-1-yl)pyridin-4-yl)-1H-indazole-4-carboxamide, also known as GSK343 (Formula (3)):

Formula (3)

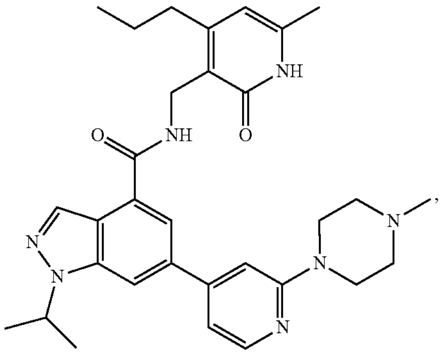

or a pharmaceutically acceptable salt, solvate, hydrate, cocrystal, tautomer, or prodrug thereof. The synthesis and properties of Formula (3), and other EZH2 inhibitors suitable for use with the present methods, are described in, e.g., U.S. Pat. Nos. 8,637,509, 8,846,935, and 9,018,382, the disclosures of which are incorporated by reference herein.

In an embodiment, the EZH2 inhibitor is N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide, also known as tazemetostat or EPZ-6438 (Formula (4)):

Formula (4)

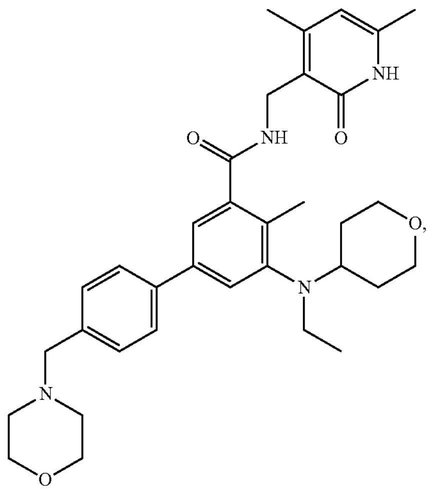

or a pharmaceutically acceptable salt, solvate, hydrate, cocrystal, tautomer, or prodrug thereof. Tazemetostat is commercially available from Epizyme, Inc., and is described in Knutson, et al., *Mol. Cancer Ther.* 2014, 13, 842-54. The synthesis and properties of tazemetostat and other suitable EZH2 inhibitors are described in, e.g., U.S. Pat. Nos. 8,765,732, 8,410,088, and 9,090,562, the disclosures of which are incorporated by reference herein.

In an embodiment, the EZH2 inhibitor is (R,Z)-1-(1-(1-(ethylsulfonyl)piperidin-4-yl)ethyl)-N-((2-hydroxy-4-methoxy-6-methylpyridin-3-yl)methyl)-2-methyl-1H-indole-3-carbimidic acid, also known as CPI-169 (Formula (5)):

Formula (5)

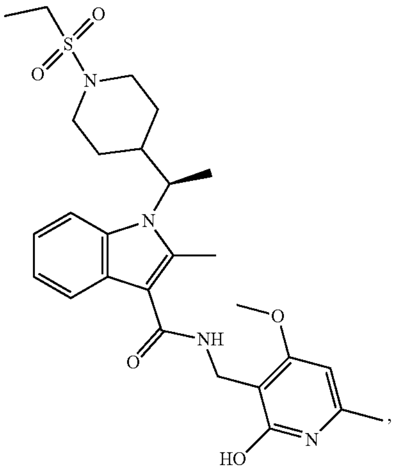

or a pharmaceutically acceptable salt, solvate, hydrate, cocrystal, tautomer, or prodrug thereof. The synthesis and properties of Formula (5) and other suitable EZH2 inhibitors are described in, e.g., U.S. Patent Application Publication No. US 2016/0009718 A1, the disclosures of which are incorporated by reference herein.

In an embodiment, the EZH2 inhibitor is 1-cyclopentyl-N-((4,6-dimethyl-2-oxo-1,2-dihydropyridin-3-yl)methyl)-6-(4-(morpholinomethyl)phenyl)-1H-indazole-4-carboxamide, also known as EPZ-5687 (Formula (6)):

Formula (6)

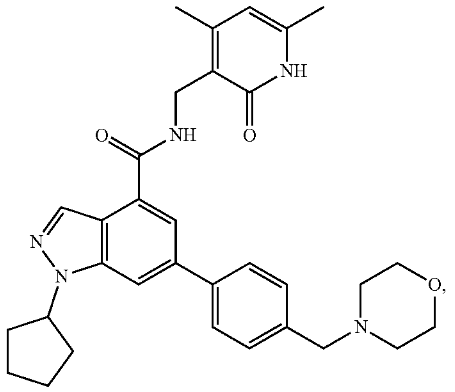

or a pharmaceutically acceptable salt, solvate, hydrate, cocrystal, tautomer, or prodrug thereof.

In an embodiment, the EZH2 inhibitor is N-((4,6-dimethyl-2-oxo-1,2-dihydropyridin-3-yl)methyl)-3-(ethyl((1R, 4R)-4-((2-methoxyethyl)(methyl)amino)cyclohexyl)amino)-2-methyl-5-(3-morpholinoprop-1-yn-1-yl)benzamide, also known as EPZ-11989 (Formula (7)):

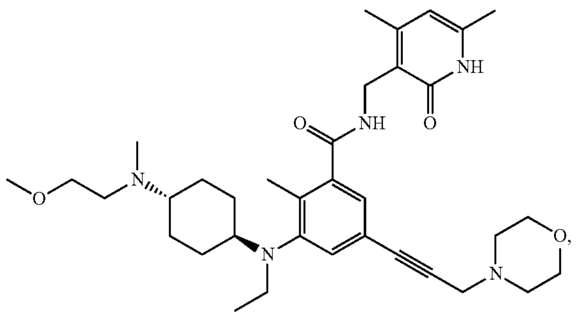 [SMILES: CCN(c1cc(C#CCN2CCOCC2)cc(C(=O)NCc2c(C)cc(C)[nH]c2=O)c1C)[C@H]1CC[C@H](N(C)CCOC)CC1]

or a pharmaceutically acceptable salt, solvate, hydrate, cocrystal, tautomer, or prodrug thereof.

In an embodiment, the EZH2 inhibitor is 1-isopropyl-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide, also known as UNC-1999 (Formula (8)):

Formula (8)

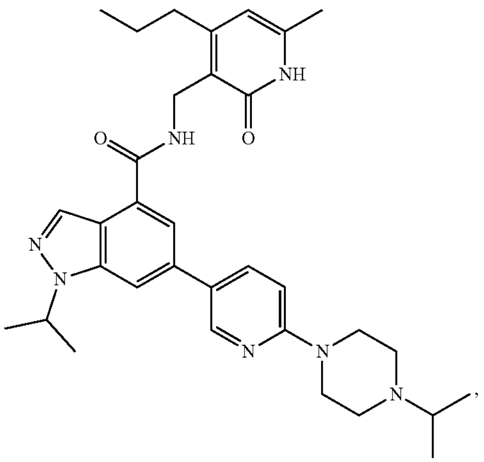

or a pharmaceutically acceptable salt, solvate, hydrate, cocrystal, tautomer, or prodrug thereof.

In an embodiment, the EZH2 inhibitor is 6-cyano-N-((4,6-dimethyl-2-oxo-1,2-dihydropyridin-3-yl)methyl)-1-(pentan-3-yl)-1H-indole-4-carboxamide, also known as E11 (Formula (9)):

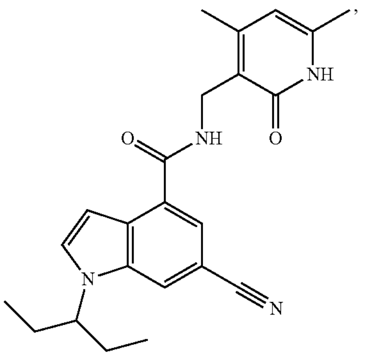 [SMILES: CCC(CC)n1ccc2c(C(=O)NCc3c(C)cc(C)[nH]c3=O)cc(C#N)cc21]

or a pharmaceutically acceptable salt, solvate, hydrate, cocrystal, tautomer, or prodrug thereof. The synthesis and properties of E11 are described in, e.g., Qi, et al., *Proc. Natl. Acad. Sci. USA* 2012, 109, 21360-65.

In an embodiment, the EZH2 inhibitor is (1S,2R,5R)-5-(4-amino-1H-imidazo[4,5-c]pyridin-1-yl)-3-(hydroxymethyl)-3-cyclopentene-1,2-diol, also known as DZNep (Formula (10)):

Formula (10)

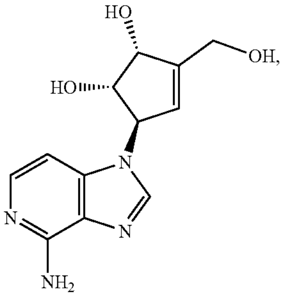

or a pharmaceutically acceptable salt, solvate, hydrate, cocrystal, tautomer, or prodrug thereof.

In an embodiment, the EZH2 inhibitor is (2S,5S)-2,5-diamino-6-((2R,3S,4R,5R)-5-(6-amino-9H-purin-9-yl)-3,4-dihydroxytetrahydrofuran-2-yl) hexanoic acid, also known as 5'-deoxy-5'-(1,4-diamino-4-carboxybutyl) adenosine and sinefungin (Formula (11)):

Formula (11)

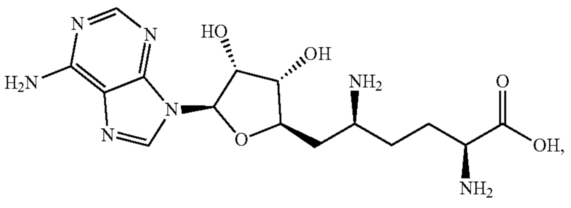

or a pharmaceutically acceptable salt, solvate, hydrate, cocrystal, tautomer, or prodrug thereof. The isolation of sinefungin is described, e.g., in U.S. Pat. No. 3,758,681, the disclosure of which is incorporated by reference herein. The synthesis of sinefungin is described, e.g., in Maguire, et al., *J. Org. Chem.* 1990, 55, 948. In an embodiment, the EZH2 inhibitor is a derivative of sinefungin. Sinefungin derivatives, and are described, e.g., in French Patent No. FR 2664277 B1 and in Zheng, et al., *J. Am. Chem. Soc.* 2012, 134, 18004-14, the disclosures of which are incorporated by reference herein.

In an embodiment, the EZH2 inhibitor is CPI-1205, or a pharmaceutically acceptable salt, solvate, hydrate, cocrystal, tautomer, or prodrug thereof. CPI-1205 is available from Constellation Pharmaceuticals.

In some embodiments, the EZH2 inhibitor is GSK126, UNC1999, or a combination combination thereof, or a pharmaceutically acceptable salt, solvate, hydrate, cocrystal, tautomer, or prodrug thereof.

In some embodiments, the EZH2 inhibitor is GSK126 or a pharmaceutically acceptable salt, solvate, hydrate, cocrystal, tautomer, or prodrug thereof.

In some embodiments, the EZH2 inhibitor is UNC1999 or a pharmaceutically acceptable salt, solvate, hydrate, cocrystal, tautomer, or prodrug thereof.

Platinum-Based Antineoplastic Drugs

In an embodiment, the invention includes a method of treating a cancer in a human subject suffering from the cancer in which cancer cells overexpress arginine methyltransferase CARM1, the method comprising the step of administering a therapeutically effective dose of an active pharmaceutical ingredient that is an EZH2 inhibitor to the human subject, and further comprising the step of administering an active pharmaceutical ingredient that is a platinum-based antineoplastic drug. The platinum-based antineoplastic drug may be administered before, concurrently with, or after the EZH2 inhibitor. Any platinum-based antineoplastic drug known in the art may be used, as described, e.g., in Kelland, *Nature Rev. Cancer* 2007, 7, 573-84. In particular, it is one of the platinum-based antineoplastic drugs described in more detail in the following paragraphs.

In an embodiment, the platinum-based antineoplastic drug is selected from the group consisting of cisplatin, carboplatin, oxaliplatin, satraplatin, picoplatin, nedaplatin, triplatin tetranitrate, lipoplatin (liposomal cisplatin), combinations thereof, and pharmaceutically acceptable salts, solvates, hydrates, cocrystals, or prodrugs thereof. The properties of cisplatin, carboplatin, oxaliplatin, satraplatin, picoplatin, nedaplatin, triplatin tetranitrate, and lipoplatin are known to those of ordinary skill in the art, and the active pharmaceutical ingredients and formulated products are commercially available. Wheate, et al., *Dalton Trans.* 2010, 39, 8113-27; Apps, et al., *Endocrine-Related Cancer* 2015, 22, 219-233.

In an embodiment, the platinum-based antineoplastic drug is cisplatin, which has the chemical name (SP-4-2)-diamminedichloroplatinum(II) (Formula (12)):

Formula (12)

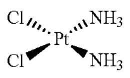

or a pharmaceutically acceptable salt, solvate, hydrate, cocrystal, or prodrug thereof. The preparation and properties of cisplatin are described in, e.g., von Hoff and Rozencweig, *Adv. Pharmacol. & Chemtherapy* 1979, 16, 273-294.

In an embodiment, the platinum-based antineoplastic drug is carboplatin, which has the chemical name cis-diammine (cyclobutane-1,1-dicarboxylate-O,O')platinum (II) (Formula (13)):

Formula (13)

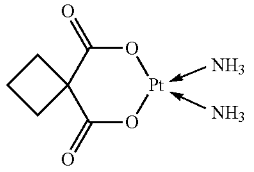

or a pharmaceutically acceptable salt, solvate, hydrate, cocrystal, or prodrug thereof. The preparation and properties of carboplatin are described in U.S. Pat. No. 4,140,707, the disclosure of which is incorporated by reference herein.

In an embodiment, the platinum-based antineoplastic drug is oxaliplatin, which has the chemical name [(1R,2R)-cyclohexane-1,2-diamine](ethanedioato-O,O')platinum(II) or cis-[(1R,2R)-1,2-cyclohexanediamine-N,N] [oxalato (2-)—$O_1$O] platinum (Formula (14)):

Formula (14)

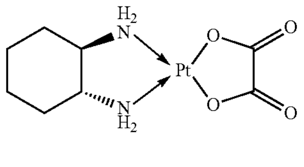

or a pharmaceutically acceptable salt, solvate, hydrate, cocrystal, or prodrug thereof. The preparation and properties of oxaliplatin are described in U.S. Pat. Nos. 4,169,846; 5,420,319; and 5,716,988, the disclosures of which are incorporated by reference herein.

In an embodiment, the platinum-based antineoplastic drug is satraplatin, which has the chemical name (OC-6-43)-bis (acetato)amminedichloro(cyclohexylamine)platinum or bis (acetato) ammine dichloro (cyclohexylamine) platinum (IV) (Formula (15)):

Formula (15)

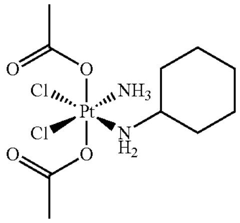

or a pharmaceutically acceptable salt, solvate, hydrate, cocrystal, or prodrug thereof. The preparation and properties of satraplatin are described in U.S. Pat. Nos. 5,072,011; 5,244,919; 6,518,428, the disclosures of which are incorporated by reference herein.

In an embodiment, the platinum-based antineoplastic drug is picoplatin, which has the chemical name azane; 2-methylpyridine; platinum (2+); dichloride (Formula (16)):

Formula (16)

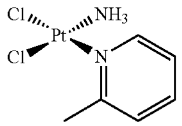

or a pharmaceutically acceptable salt, solvate, hydrate, cocrystal, or prodrug thereof. The preparation and properties of picoplatin are described in U.S. Pat. Nos. 5,665,771 and 6,518,428; the disclosures of which are incorporated by reference herein.

In an embodiment, the platinum-based antineoplastic drug is nedaplatin, which has the chemical name diammine [(hydroxy-κO)acetato(2-)-κO]platinum (Formula (17)):

Formula (17)

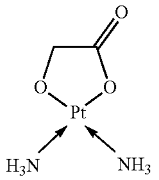

or a pharmaceutically acceptable salt, solvate, hydrate, cocrystal, or prodrug thereof. Nedaplatin has been described in Alberts, et al., *Cancer Chemother. Pharmacol.* 1997, 39, 493-497 and Wheate, et al., *Dalton Trans.* 2010, 39, 8113-8127.

In an embodiment, the platinum-based antineoplastic drug is triplatin or a pharmaceutically acceptable salt, solvate, hydrate, cocrystal, or prodrug thereof. In an embodiment, the platinum drug is triplatin tetranitrate (Formula (18)):

Formula (20)

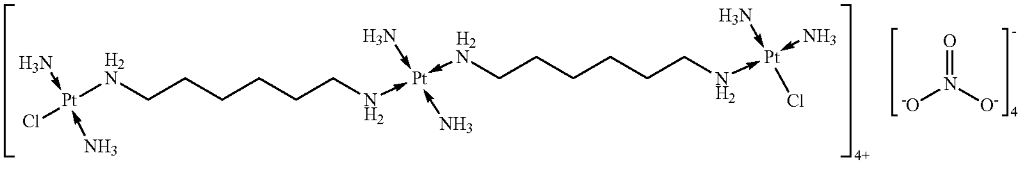

In an embodiment, the platinum-based antineoplastic drug is lipoplatin, which is a nanoparticle containing a combination of lipids and cisplatin. The clinical efficacy of lipoplatin is described in Stathopoulos, et al., *Cancer Chemtherapy & Pharmacol.* 2011, 68, 945-950. The preparation, properties, and uses of lipoplatin are described in U.S. Pat. No. 6,511,676, the disclosure of which is incorporated by reference herein.

Pharmaceutical Compositions

In an embodiment, an active pharmaceutical ingredient or combination of active pharmaceutical ingredients, such as any of the foregoing EZH2 inhibitors and optionally platinum-based antineoplastic drugs, is provided as a pharmaceutically acceptable composition.

In some embodiments, the concentration of each of the active pharmaceutical ingredients provided in the pharmaceutical compositions of the invention, such as any of the foregoing EZH2 inhibitors, is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of each of the active pharmaceutical ingredients provided in the pharmaceutical compositions of the invention, such as any of the foregoing EZH2 inhibitors, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing EZH2 inhibitors, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of each of the active pharmaceutical ingredients provided in the pharmaceutical compositions of the invention, such as any of the foregoing EZH2 inhibitors, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of each of the active pharmaceutical ingredients provided in the pharmaceutical compositions of the invention, such as any of the foregoing EZH2 inhibitors, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the foregoing EZH2 inhibitors, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the foregoing EZH2 inhibitors may also be used if appropriate.

In an embodiment, the molar ratio of two active pharmaceutical ingredients in the pharmaceutical compositions is in the range from 10:1 to 1:10, from 2.5:1 to 1:2.5, and about 1:1. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In an embodiment, the pharmaceutical compositions of the present invention, such as any of the foregoing EZH2 inhibitors, are for use in the treatment of cancers associated with overexpression or amplification of CARM1. In an embodiment, the pharmaceutical compositions of the present invention are for use in the treatment of a cancer associated with overexpression or amplification of CARM1 selected from the group consisting of bladder cancer, squamous cell carcinoma including head and neck cancer, pancreatic ductal adenocarcinoma, pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, esophageal cancer, testicular cancer, gynecological cancer, thyroid cancer, acquired immune deficiency syndrome (AIDS)-related lymphoma, Kaposi's sarcoma, viral-induced cancer, glioblastoma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

Described below are non-limiting pharmaceutical compositions and methods for preparing the same.

Pharmaceutical Compositions for Oral Administration

In some embodiments, the invention provides a pharmaceutical composition for oral administration containing the active pharmaceutical ingredient or combination of active pharmaceutical ingredients, such as the EZH2 inhibitors described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

Pharmaceutical Compositions for Injection

In some embodiments, the invention provides a pharmaceutical composition for injection containing an active pharmaceutical ingredient or combination of active pharmaceutical ingredients, such as an EZH2 inhibitor and optionally a platinum-based antineoplastic drug, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, the invention provides a pharmaceutical composition for transdermal delivery containing an active pharmaceutical ingredient or combination of active pharmaceutical ingredients, such as the EZH2 inhibitors described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the EZH2 inhibitors described herein. The compositions are administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, orally or nasally, from devices that deliver the formulation in an appropriate manner. Dry powder inhalers may also be used to provide inhaled delivery of the compositions.

Other Pharmaceutical Compositions

Pharmaceutical compositions of the EZH2 inhibitors described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., *Handbook of Clinical Drug Data*, Tenth Edition, McGraw-Hill, 2002; and Pratt and Taylor, eds., *Principles of Drug Action*, Third Edition, Churchill Livingston, 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), via local delivery by catheter or stent or through inhalation. The active pharmaceutical ingredient or combination of active pharmaceutical ingredients can also be administered intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g., PEO-PLLA); polydimethylsiloxane, poly (ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. The active pharmaceutical ingredient or combination of active pharmaceutical ingredients may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. The active pharmaceutical ingredient or combination of active pharmaceutical ingredients may additionally be administered intravascularly from a balloon used during angioplasty. Extravascular administration of an active pharmaceutical ingredient or combination of active pharmaceutical ingredients via the pericard or via advential application of formulations of the invention may also be performed to decrease restenosis.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit comprising a composition comprising a therapeutically effective amount of an active pharmaceutical ingredient or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides a kit comprising (1) a composition comprising a therapeutically effective amount of an active pharmaceutical ingredient or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

The kits described above are for use in the treatment of the diseases and conditions described herein. In an embodiment, the kits are for use in the treatment of cancer. In some embodiments, the kits are for use in treating solid tumor cancers.

In an embodiment, the kits of the present invention are for use in the treatment of cancer. In an embodiment, the kits of the present invention are for use in the treatment of a cancer selected from the group consisting of bladder cancer, squamous cell carcinoma including head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, renal cancer, kidney cancer, liver cancer, ovarian cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophageal tumors, hematological neoplasms, non-small-cell lung cancer, chronic myelocytic leukemia, diffuse large B-cell lymphoma, esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, indolent non-Hodgkin's lymphoma, ovary tumor, pancreas tumor, renal cell carcinoma, small-cell lung cancer, stage IV melanoma, chronic lymphocytic leukemia, B-cell acute lymphoblastic leukemia (ALL), mature B-cell ALL, follicular lymphoma, mantle cell lymphoma, and Burkitt's lymphoma.

Dosages and Dosing Regimens

The amounts of the pharmaceutical compositions administered using the methods herein, such as the dosages of EZH2 inhibitors, will be dependent on the human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in $mg/m^2$ of body surface area.

In some embodiments, the invention includes a methods of treating a cancer in a human subject suffering from the cancer in which cancer cells overexpress arginine methyltransferase CARM1, the method comprising the steps of administering a therapeutically effective dose of an active pharmaceutical ingredient that is an EZH2 inhibitor and an active pharmaceutical ingredient that is an platinum-based antineoplastic drug to the human subject. In some embodiments, the EZH2 inhibitor is administered before the platinum-based antincoplastic drug. In some embodiments, the platinum-based antineoplastic drug is administered concurrently with the EZH2 inhibitor. In some embodiments, the EZH2 inhibitor is administered after the platinum-based antineoplastic drug.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients in the methods of the invention may continue as long as necessary. In selected embodiments, a pharmaceutical composition is administered for more than 1, 2, 3, 4, 5, 6, 7, 14, or 28 days. In some embodiments, a pharmaceutical composition is administered for less than 28, 14, 7, 6, 5, 4, 3, 2, or 1 day. In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an effective dosage of an active pharmaceutical ingredient disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of an active pharmaceutical ingredient disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect—e.g., by dividing such larger doses into several small doses for administration throughout the day.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—CARM1 is Associated with Poor Prognosis in Ovarian Cancer Patients

Figure 2:
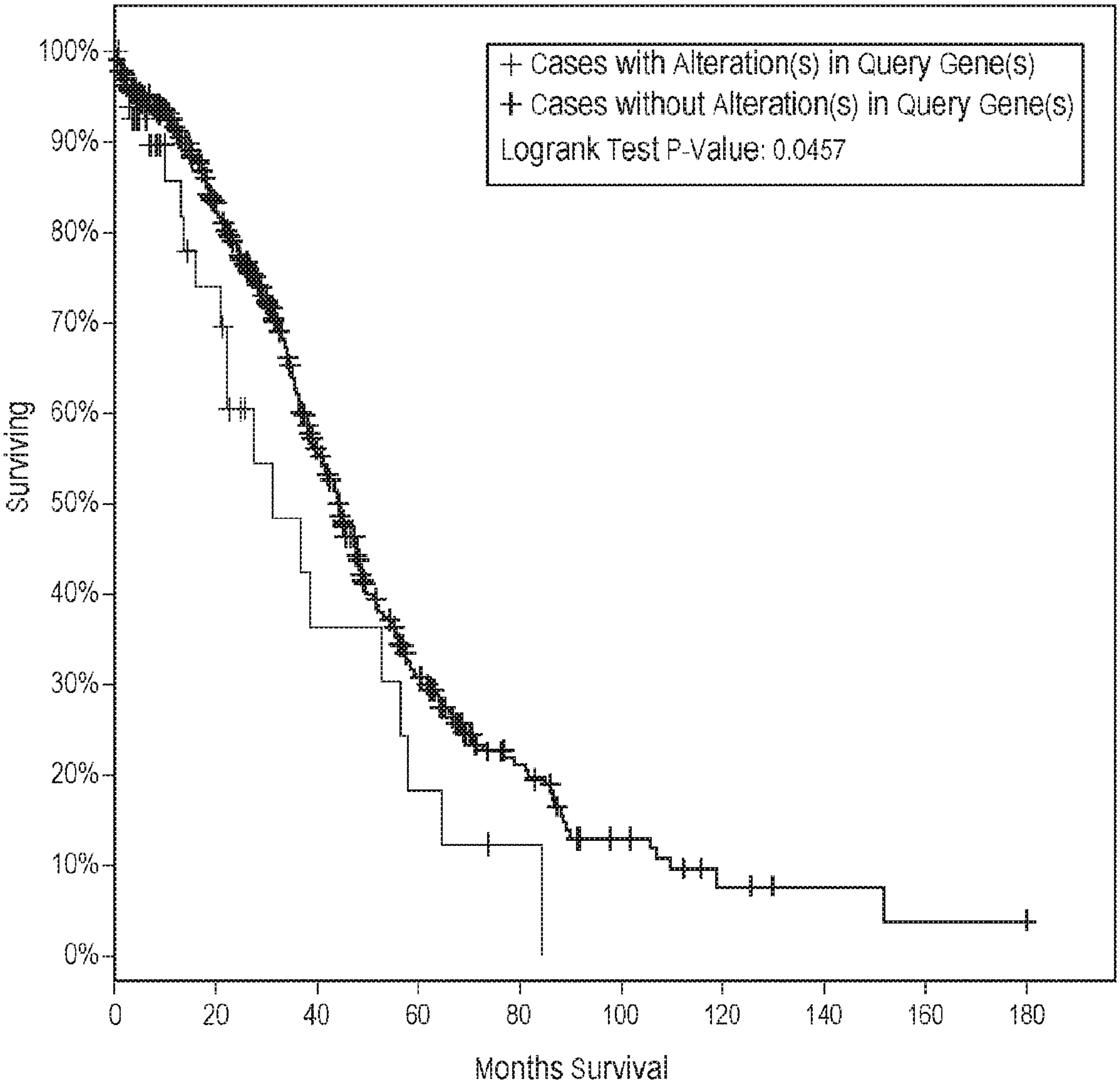
FIG. 2 illustrates overall survival in CARM1-expressing cells. Data was obtained from the Cancer Genome Atlas.
Figure 3:
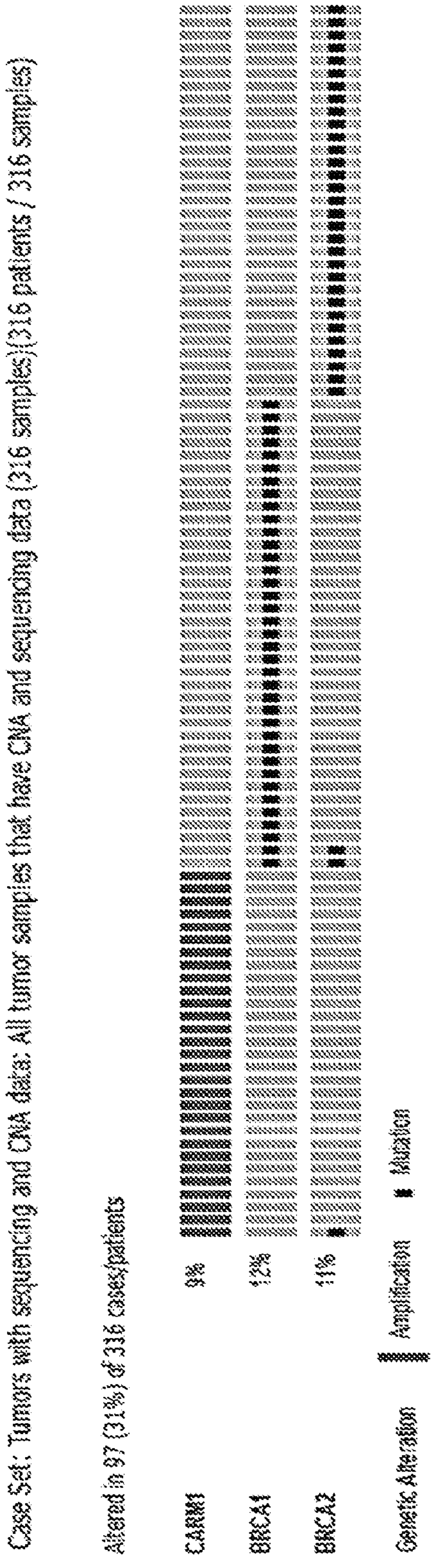
FIG. 3 illustrates the co-occurrence of CARM1 amplification with the mutations in HR DNA repair genes, BRCA1 and BRCA2.

In FIG. 1, CARM1 expression in different types of cancer is illustrated. Significant amplification is observed in a number of cancers, including ovarian, uterine, breast, sarcoma, and pancreatic cancers and glioma. In FIG. 2, overall survival in CARM1-expressing cells is shown to be poor. Data was obtained from the Cancer Genome Atlas. FIG. 3 illustrates the lack of co-occurrence of CARM1 amplification with mutations in the homologous recombination (HR) DNA repair genes BRCA1 and BRCA2. Overall, the results indicate that CARM1 is amplified in a variety of cancers, including 10% of high-grade ovarian carcinomas. CARM1 amplification does not co-occur with mutations in the HR DNA repair pathway, and CARM1 amplification is associated with poor prognosis.

Example 2—CARM1-Expressing Cells are Sensitive to the EZH2 Inhibitor GSK 126

Figure 4:
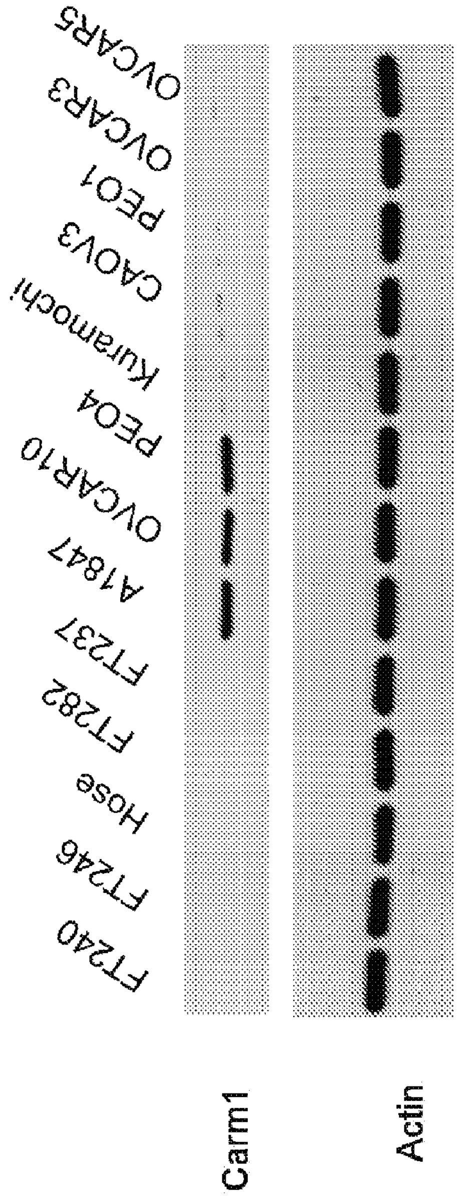
FIG. 4 illustrates CARM1 expression in a panel of high-grade ovarian carcinoma.
Figure 5:
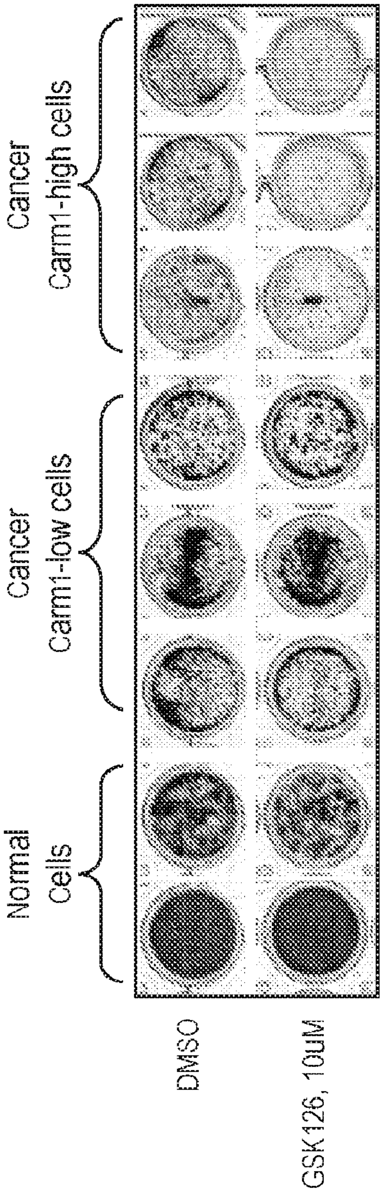
FIG. 5 illustrates the results of a colony formation assay with a panel of normal and ovarian cancer cell lines in the presence of GSK126.
Figure 6:
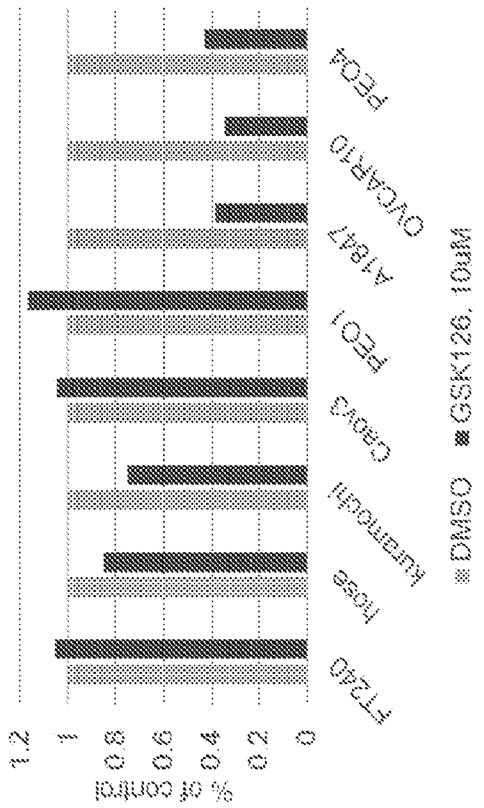
FIG. 6 illustrates a quantification of the data shown in FIG. 5.

In FIG. 4, CARM1 expression in a panel of high-grade ovarian carcinomas is depicted. FIG. 5 illustrates the results of a colony formation assay with a panel of normal and ovarian cancer cell lines with DMSO and with 10 μM of the EZH2 inhibitor GSK 126 (Formula (1)). The data in FIG. 5 is quantitatively assessed in FIG. 6, with both figures illustrating the particular sensitivity of CARM1-expressing cells to the EZH2 inhibitor.

In FIG. 7, response curves for GSK126 in a panel of normal and ovarian cancer cell lines are shown. The $IC_{50}$ values determined from these curves for the panel of normal and ovarian cancer cell lines are listed in FIG. 8. Significantly reduced $IC_{50}$ values are observed for the CARM1-expressing cell lines (A1847, OVCAR10, and PEO4).

Overall, the results demonstrate the surprising finding that CARM1-expressing cells are sensitive to the EZH2 inhibitor GSK126. Sensitization of CARM1-expressing cells to an EZH2 inhibitor may be further exploited by administration of one or more platinum-based antineoplastic drugs.

Figure 10:
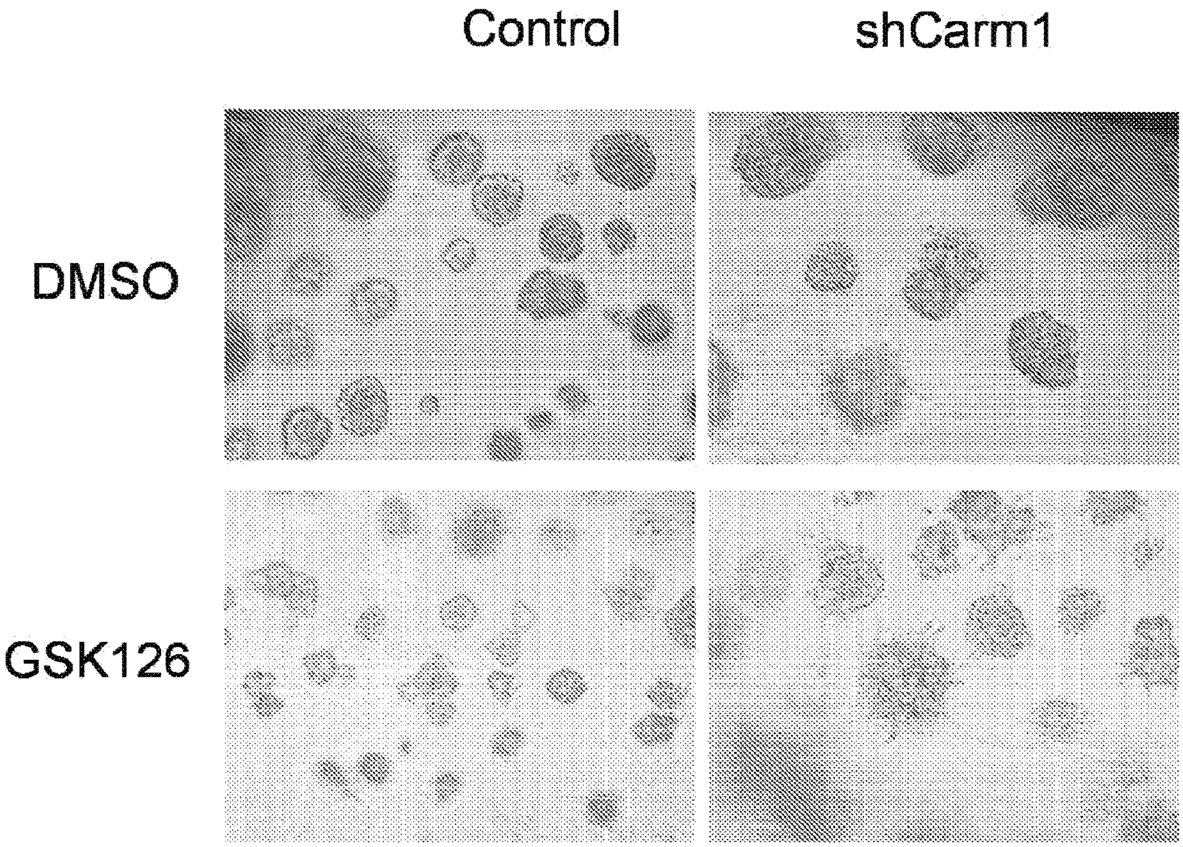
FIG. 10 illustrates the results of a colony formation assay (unstained, magnified) with normal and CARM1-depleted cells, in DMSO (control) and treated with GSK126.
Figure 11:
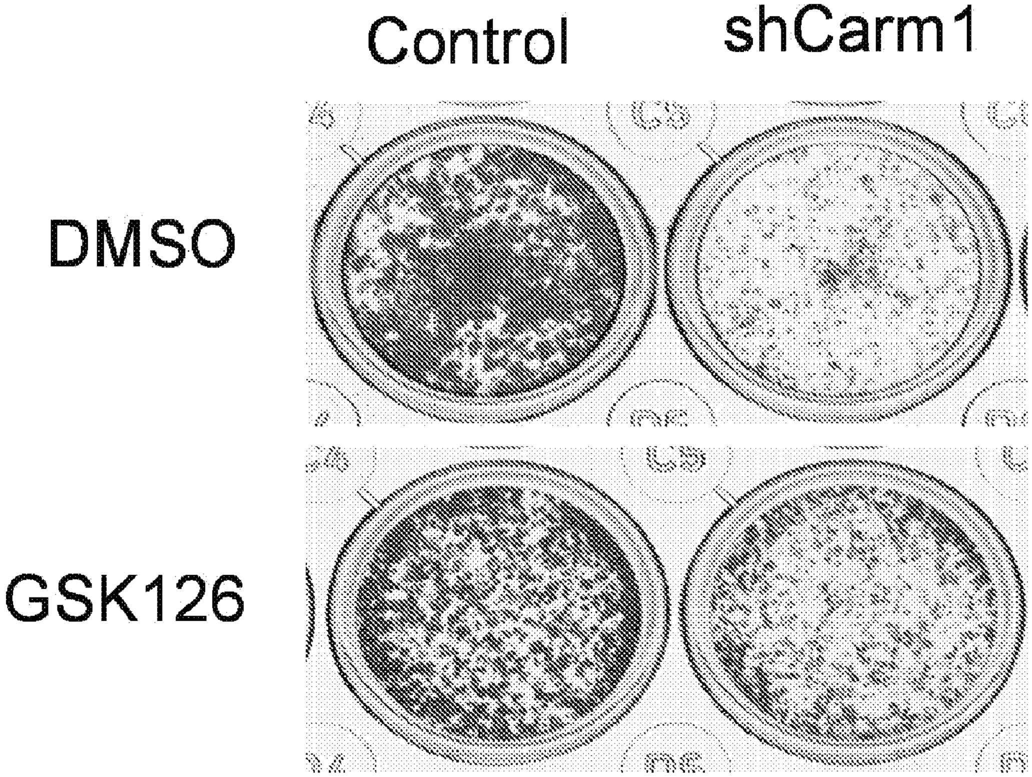
FIG. 11 illustrates the results of a colony formation assay with normal and CARM1-depleted cells, in DMSO (control) and treated with GSK126.
Figure 12:
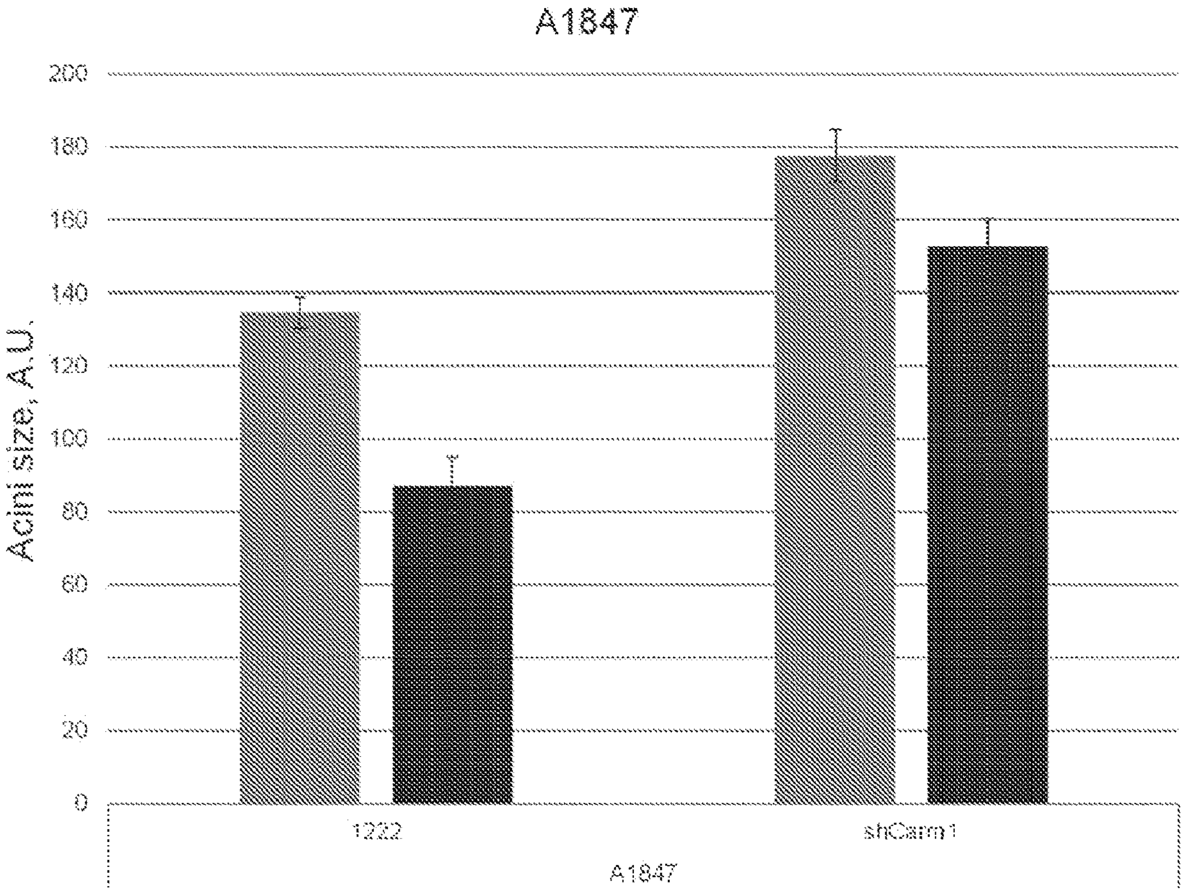
FIG. 12 illustrates a quantification of the data shown in FIG. 11.
Figure 13:
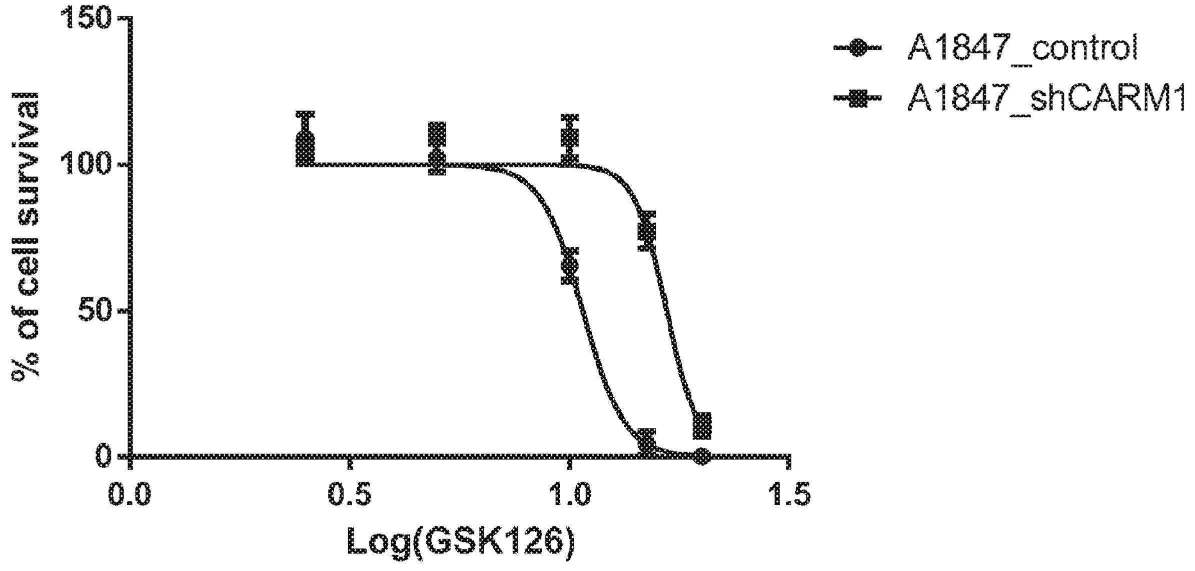
FIG. 13 illustrates the results of treatment of CARM1 depleted cells with GSK126. Error bars indicate S.E. for n=3. *, p≤0.05.

Example 3—CARM1 Depletion Abrogates GSK126 Sensitivity in CARM1-Expressing Cells To confirm the relationship between CARM1 overexpression and sensitivity to EZH2 inhibition, further studies were performed to assess the impact of CARM1 depletion. In FIG. 9, a Western blot of CARM1 and BAF155me2 in CARM1 depleted cells with a control (Actin) is shown. In addition, the results of a colony formation assay (unstained, magnified) with normal and CARM1-depleted cells, in DMSO (control) and treated with GSK126, are shown in FIG. 10. A colony formation assay with normal and CARM1-depleted cells, in DMSO (control) and after treatment with GSK 126 is shown in FIG. 11, with the results quantified in FIG. 12. Finally, FIG. 13 illustrates the results of treatment of CARM1 depleted cells with GSK126. Together, the results indicate that CARM1 depletion leads to decreased BAF155 methylation, while also abrogating the sensitivity of the EZH2 inhibitor GSK 126 in CARM1-expressing cells.

Example 4—CARM1-Expressing Ovarian Cancer Depends on the Histone Methyltransferase EZH2 Activity In this example, it is shown that EZH2 inhibition is selective against CARM1 expression in epithelial ovarian cancer. High CARM1 expression predicts a shorter survival in ovarian cancer patients. Inhibition of EZH2 activity using a clinically applicable small molecule inhibitor significantly suppressed the growth of CARM1-expressing, but not CARM1 deficient, ovarian tumors in two xenograft models and improved the survival of mice bearing CARM1-expressing tumors. The observed selectivity correlates with upregulation of EZH2 target genes in a CARM1-dependent manner. CARM1 promotes EZH2 dependent gene silencing of EZH2/BAF155 target tumor suppressor genes by methylating BAF155 to alter the antagonism between EZH2 and BAF155. Together, these results indicate that pharmacological inhibition of EZH2 is a novel therapeutic strategy for CARM1-expressing cancers.

Methods

Cell Lines and Culture Conditions.

Human EOC cell lines were obtained from ATCC within 3 years or obtained as described in Li, et al. *MCR* (2010) 8:1610-8, and were re-authenticated by The Wistar Institute's Genomics Facility at the end of experiments within last three months using short tandem repeat profiling using AmpFISTR Identifiler PCR Amplification kit (Life Technologies) and cultured as described in Li, et al. *MCR* (2010) 8:1610-8. Human ovarian surface epithelial cells were obtained and cultured as described in Li, et al. *MCR* (2010) 8:1610-8, Mycoplasma testing was performed by LookOut Mycoplasma PCR detection (Sigma).

Reagents and Antibodies.

Small molecules used in the epigenetic screen were obtained from Structural Genomics Consortium or The Wistar Institute Molecular Screening Facility. GSK126 was obtained from Active Biochem or Xcess Biosciences. Antibodies were obtained from: mouse anti-CARM1 (Cell Signaling, Cat. No: 12495, 1:1000 for immunoblotting), goat anti-BAF155 (Santa Cruz, Cat. No: SC9746, 1:1000 for immunoblotting), rabbit anti-methylated R1064 BAF155 (Millipore, Cat. No: ABE1339, 1:1000 for immunoblotting), rabbit anti-EZH2 (Cell Signaling, Cat. No: 5246, 1:1000 for immunoblotting), rabbit anti-cleaved PARP p85 (Promega, Cat. No: G7341, 1:1000 for immunoblotting), mouse anti-Ki67 (Cell Signaling, Cat. No: 9449, 1:500 for IHC), rabbit anti-cleaved caspase 3 (Cell Signaling, Cat. No: 9661, 1:1000 for immunoblotting and 1:50 for IHC), rabbit anti-H3K27Me3 (Cell Signaling, Cat. No: 9733, 1:1000 for immunoblotting and 1:100 for IHC), mouse anti-β-actin (Sigma, Cat. No: A1978, 1:20,000 for immunoblotting), rabbit anti-RNA pol II (Santa Cruz, Cat. No: sc-899). Growth factor reduced basement membrane matrix (Matrigel) was obtained from Corning.

CRISPR-Mediated CARM1 Knockout.

pLentiCRISPR-CARM1 was constructed by inserting the CARM1 guide RNA (gRNA; 5'-AGCACGGAAAATC-TACGCGG-3' (SEQ ID NO: 1)) according to Shalem, et al. Science (2014) 343:84-7. In brief, pLentiCRISPR v2 (Addgene) was digested and dephosphorylated with BsmBI restriction enzyme (Fermentas) for 30 min at 37° C. The digested plasmid was run on a 1% agarose gel, cut out, and purified using the Wizard SV Gel and PCR Clean Up kit (Promega). The oligonucleotides were phosphorylated using T4 PNK (M0201S) with T4 Ligation Buffer (New England Biolabs, Inc.). Samples were annealed in a thermocycler at 37° C. for 30 min and then at 95° C. for 5 min and then were ramped down to 25° C. at 5° C./min. Annealed oligonucleotides were diluted 1:200 in RNase/DNase-free water. Ligation of the annealed oligonucleotide and digested pLentiCRISPR v2 plasmid was performed using Quick Ligase (New England Biolabs, Inc.).

Lentivirus and Retrovirus Infection.

Retrovirus production and transduction were performed as described in Bitler et al. *Nature Medicine* (2015) 21:231-8 and Aird et al. *Cell Reports* (2013) 3:1252-65. Phoenix cells were used to package the viruses. Lentivirus was packaged using the Virapower Kit from Invitrogen according to the manufacturer's instructions as described in Li, et al. *MCR* (2010) 8:1610-8 and Ye, et al. *Mol. Cell Biol.* (2007) 27:2452-65. The following shRNAs obtained from the Molecular Screening Facility at The Wistar Institute were used: pLKO.1-shCARM1 (TRCN0000059090 and TRCN0000059090), pLKO.1-shEZH2 (TRCN0000040073) and pLKO.1-shBAF155 (TRCN00001353636). Cells infected with viruses encoding the puromycin resistance gene were selected in 1 μg/ml puromycin.

Reverse-Transcriptase Quantitative PCR (RT-qPCR).

RNA was isolated by RNeasy Mini Kit (Qiagen). mRNA relative expression for DAB2, DLC1, and PMAIP was determined using SYBR green 1-step iScript (Bio-Rad) with a Life Technologies QuantStudio 3. The primers were: 5'-TTCATTGCCCGTGATGTGACA-3' (DAB2 forward (SEQ ID NO: 2)) and 5'-CCTGTTGCCCGGTTTTTATGG-3' (DAB2 reverse (SEQ ID NO: 3)); 5'-AACCCAAGACTACGGCTATTCA-3' (DLC1 forward (SEQ ID NO: 4)) and 5'-CATAAAGCTGTGCATACTGGGG-3' (DLC1 reverse (SEQ ID NO: 5)); 5'-ACCAAGCCGGATTTGCGATT-3' (NOXA forward (SEQ ID NO: 6)) and 5'-ACTTGCACTTGTTCCTCGTGG-3' (NOXA reverse (SEQ ID NO: 7)); and 5'-CATGTGCAGTACATCCATACGG-3' (TIMP3 forward (SEQ ID NO: 8)) and 5'-CATCATAGACGCGACCTGTCA-3' (TIMP3 reverse (SEQ ID NO: 9)).

Annexin V Assay.

Phosphatidylserine externalization was detected using an Annexin V staining kit (Millipore) following the manufacturer's instructions. Annexin V-positive cells were detected using the Guava System and analyzed with the Guava Nexin software Module (Millipore).

3D Matrigel Assays.

Matrigel was coated on the bottom of 8-well chamber slides and cells were plated on the matrigel (4,000 cells/well) in a 3% Matrigel/Media mixture. Media, matrigel and treatment (drug/vehicle) were replenished every fourth day. On day 12, five bright-field images were captured from each well/treatment. Acini diameter was measured from images with Image-J software (NIH). Also, on day 12 cell recovery solution (BD) was used to remove acini from Matrigel, treated with trypsin and total number of cells was counted for each treatment.

Colony Formation Assay.

500 to 5,000 cell were plated into a 24 well tissue culture plate and treated with the indicated compounds. Medium was changed every three days with appropriate drug doses for 12 days or until control wells became confluent. Colonies were washed twice with PBS and fixed with 10% methanol and 10% acetic acid in distilled water. Fixed colonies were stained with 0.005% crystal violet. Integrated density was measured using NIH ImageJ software.

Intrabursal Orthotopic Xenograft Models In Vivo.

The protocols were approved by the Institutional Animal Care and Use Committee (IACUC). For in vivo experiments, the sample size of 5 mice per group was determined based on the data shown from in vitro experiments. Intrabursal orthotopic xenograft was performed as described in Bitler, et al. *Nature Medicine* (2015) 21:231-8 and Bitler et al. *Cancer Research* (2011) 71:6184-94. Briefly, $1\times10^6$ A1847 parental or A1847 CARM1 knockout cells were unilaterally injected into the ovarian bursa of 6-8-week old female immunocompromised NSG mice (n=5 per group). One week after injection the mice were randomized into two groups and treated with vehicle control (20% captisol) or GSK126 (50 mg/kg daily) for three weeks. At the end of the experiments, tumors were surgically dissected and tumor burden was calculated based on tumor weight. For survival experiments, after stopping the treatment, the mice were followed for mortality or when the tumor burden reached 10% of body weight as determined by The Wistar Institute IACUC guideline.

Subcutaneous Xenograft Models In Vivo.

The protocols were approved by the Institutional Animal Care and Use Committee (IACUC). $5\times10^6$ control A1847 or A1847 CARM1 knockout cells were unilaterally injected subcutaneously into 6-8-week old female immunocompromised NSG mice (n=5 per group). One week after injection the mice were randomized and treated with vehicle control (20% captisol) or GSK126 (50 mg/kg daily). Tumor size was measured every 3 days for 3 weeks. At end of the experiments, tumors were surgically dissected and tumor burden was calculated based on tumor weight.

Epigenetic Targeting Small Molecule Set Screen.

A1847 parental and CARM1 knockout cells were plated in 24-well plates and treated with 24 epigenetic compounds. Cell medium was changed every three days with appropriate drug doses for 14 days or until control wells became confluent. Colonies were washed twice with PBS and fixed with 10% methanol and 10% acetic acid in distilled water. Fixed colonies were stained with 0.005% crystal violet. Integrated density was measured using NIH ImageJ software as a surrogate for cell growth.

RNA Sequencing (RNA-Seq) and Chromatin Immunoprecipitation Followed by Sequencing (ChIP-Seq).

RNA was extracted with Trizol (Invitrogen) and subsequently cleaned and DNase-treated using RNeasy columns (Qiagen). DNase treated RNA was subjected to library preparation. Libraries for RNA-seq were prepared with ScriptSeq complete Gold kit (Epicentre) and subjected to a 75 bp paired-end sequencing run on NextSeq 500, using Illumina's NextSeq 500 high output sequencing kit following the manufacturer's instructions.

For ChIP-seq, cells were cross-linked with 1% formaldehyde for 10 min, followed by quenching with 125 mM glycine for 5 min. Fixed cells were resuspended in cell lysis buffer (10 mM Tris-HCl, pH7.5, 10 mM NaCl, 0.5% NP-40) and incubated on ice for 10 min. The lysates were washed with MNase digestion buffer (20 mM Tris-HCl, pH7.5, 15 mM NaCl, 60 mM KCl, 1 mM $CaCl_2$)) once and incubated for 20 minutes at 37° C. in the presence of 1,000 Gel units of MNase (NEB, M0247S) in 250 μl, reaction volume. After adding the same volume of sonication buffer (100 mM Tris-HCl, pH8.1, 20 mM EDTA, 200 mM NaCl, 2% Triton X-100, 0.2% sodium deoxycholate), the lysates were sonicated for 5 min (30 sec-on/30 sec-off) in a Diagenode bioruptor and centrifuged at 15,000 rpm for 10 min. The cleared supernatant equivalent to $2\text{-}4\times10^6$ cells was incubated with 2.5 μg of anti-EZH2 antibody (Cell Signaling, Cat. No. 5246) or 2 μg anti-H3K27Me3 antibody (Cell Signaling, Cat. No. 9733) on a rocker overnight. Bound chromatin was eluted and reverse-crosslinked at 65° C.

overnight. For next-generation sequencing, ChIP-seq libraries were prepared from 10 ng of ChIP and input DNA with the Ovation Ultralow DR Multiplex system (NuGEN). The ChIP-seq libraries were sequenced in a 51 base pairs paired end run using the Illumina HiSeq 2000.

Chromatin Immunoprecipitation (ChIP).

ChIP was performed as described in Tu et al. *Developmental Cell* (2011) 21:1077-91. The following antibodies were used to perform ChIP: anti-H3K27Me3 (Cell Signaling, Cat. No: 9733), anti-BAF155 (Santa Cruz, Cat. No: sc-9746), anti-RNA polymerase II (Santa Cruz, Cat. No: sc-899) or anti-EZH2 (Cell Signaling, Cat. No: 5246). An isotype matched IgG was used as a negative control. ChIP DNA was analyzed by quantitative PCR against the promoter of the indicated genes using the following primers: DAB2 Forward: 5'-GTGTTCGGGGAGAAGTCAAA-3' (SEQ ID NO: 10) and DAB2 Reverse: 5'-ACGGATCTGTGAAACGAAGC-3' (SEQ ID NO: 11); DLC1 Forward: 5'-AAAATTTCCAAGCGCCACTA-3' (SEQ ID NO: 12) and DLC1 Reverse: 5'-ACACCGCCTTCTACCTTCCT-3' (SEQ ID NO: 13); NOXA Forward: 5'-TATTGTGGGAGGTGGGGATA-3' (SEQ ID NO: 14) and NOXA Reverse: 5'-GGCCTGAAAACTTACGATGG-3' (SEQ ID NO: 15); TIMP3 Forward: 5'-ACTCCCCTACGCAAGGATTC-3' (SEQ ID NO: 16) and TIMP3 Reverse: 5'-CGTGTGAAGGCAGTTTGGTT-3' (SEQ ID NO: 17).

Bioinformatics Analysis.

RNA-seq data was aligned using bowtie2 (see, e.g., Langmead, et al. *Nat Methods* (2012) 9:357-9) against hg19 version of the human genome and RSEM v1.2.12 software (see, e.g., Li et al. *BMC Bioinformatics* (2011) 12:323) was used to estimate raw read counts and RPKM using Ensemble gtf tracks. EdgeR (see, e.g., Robinson et al. *Bioinformatics* (2010) 26:139-40) was used to estimate significance of differential expression between KO and parental samples. Overall gene expression changes were considered significant if passed FDR<5%, Fold>3 thresholds. ChIP-seq data was aligned using bowtie (see, e.g., Langmead et al. *Genome Biol.* (2009) 10: R25) against hg19 version of the human genome and HOMER (see, e.g., Heinz et al. *Mol Cell* (2010) 38:576-89) was used to call significant peaks in parental vs. CARM1 knockout comparison using style histone option and peaks that passed FDR<1% threshold were called significantly decreased in knockout cells. Genes that had significantly decreased in knockout EZH2 and H3K27Me3 peak were considered and overlapped with genes significantly upregulated in knockout cells. Significance of overlap was tested using hypergeometric test using 57,736 Ensemble genes as a population size. Gene set enrichment analysis of gene sets was done using QIAGEN's Ingenuity® Pathway Analysis software (IPA®, QIAGEN Redwood City, www.qiagen.com/ingenuity) using "Diseases & Functions" and "Upstream Analysis" options. Functions with at least 10 member genes that passed $p<10^{-5}$ threshold and upstream regulators (transcription factors only) that passed $p<10^{-10}$ and had a significantly predicted activation state (|Z|>2) were considered. TCGA data RNASeqV2 level 3 expression data for 579 ovarian cancer (OV) patients was downloaded and tested for negative association with CARM1 expression using both Spearman and Pearson correlation and results overlapped with CARM1 parental/KO data using Entrez gene ID. The RNA-seq and ChIP-seq data was submitted to the Gene Expression Omnibus (GEO) database and can be accessed using accession number: GSE95645.

Statistical Analysis.

Statistical analyses were performed using GraphPad Prism 5 (GraphPad) for Mac OS. Quantitative data are expressed as mean±S.E.M. unless otherwise stated. Spearman's or Pearson's test was used to measure statistical correlation. For all statistical analyses, the level of significance was set at 0.05.

Results

CARM1 is Amplified in EOC and its Amplification/High Expression Correlates with Poor Survival.

Figure 14:
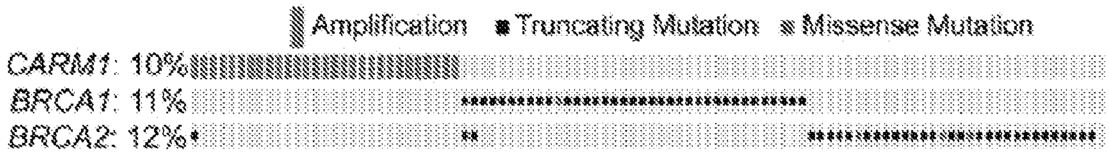
FIG. 14 illustrates CARM1 amplification and BRCA1/2 mutation profiles in the TCGA HGSOC database.
Figure 15:
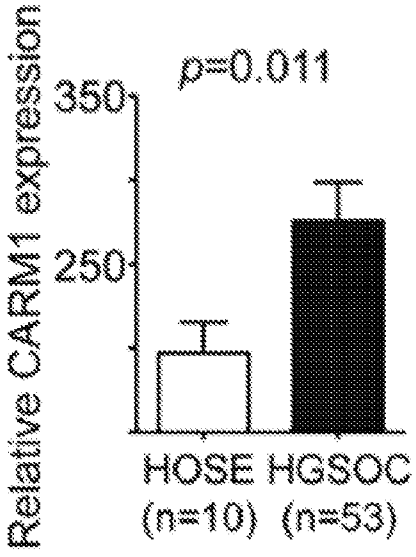
FIG. 15 illustrates relative expression of CARM1 in laser capture and microdissected (LCM) high-grade serous ovarian cancer (HGSOC) and normal human ovarian surface epithelial (HOSE) cells.
Figure 16:
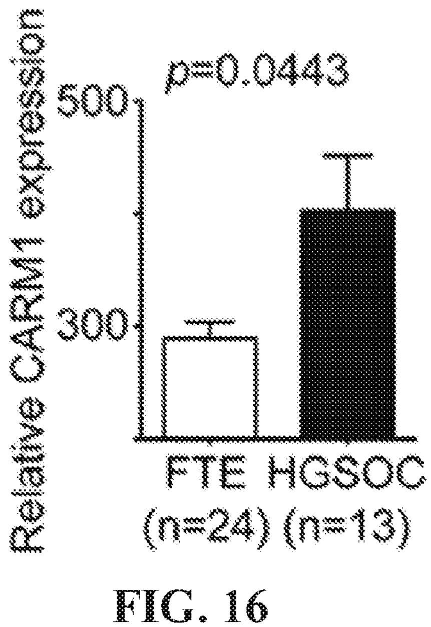
FIG. 16 illustrates relative expression of CARM1 in laser captured and microdissected HGSOC and fallopian tube epithelial (FTE) cells.
Figure 17:
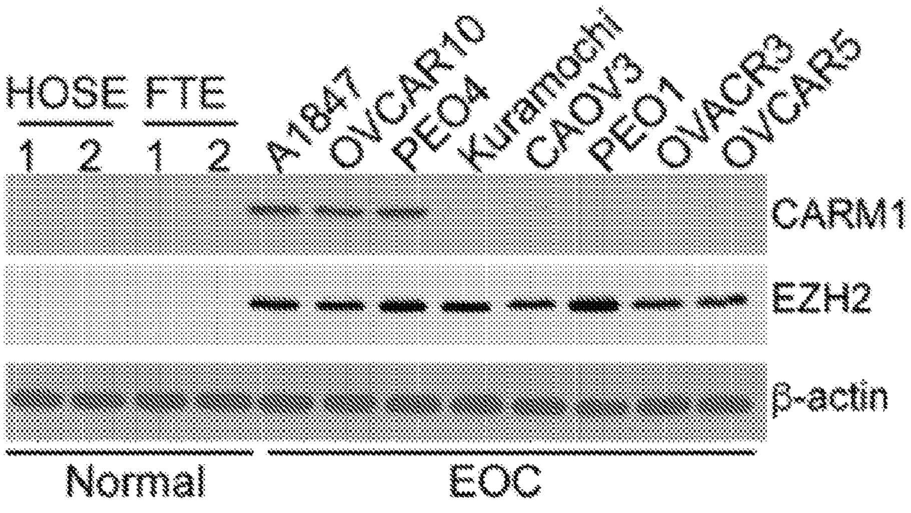
FIG. 17 illustrates expression of CARM1 and EZH2 in the indicated EOC cells lines, HOSE, and FTE cells determined by immunoblot. Expression of β-actin was used as a loading control.
Figure 18:
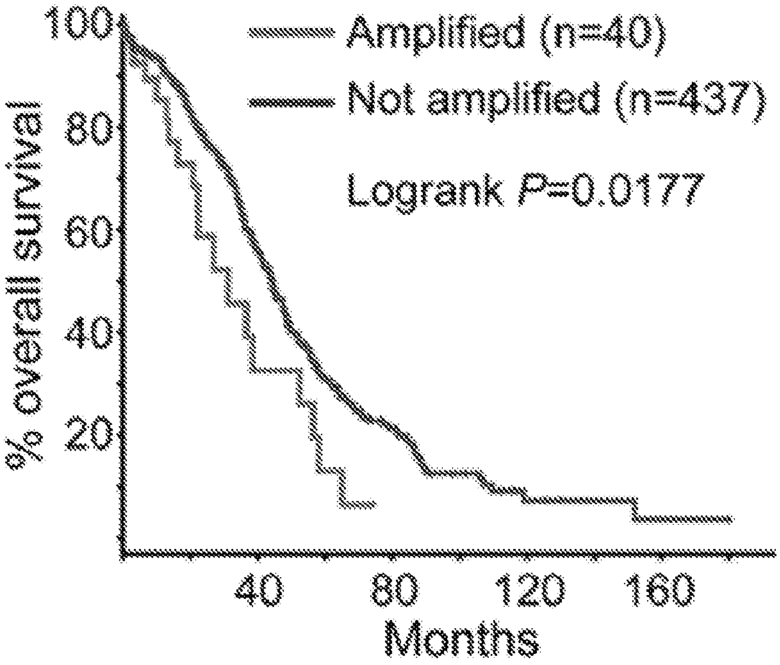
FIG. 18 illustrates overall survival of EOC patients with or without CARM1 amplification based on TCGA copy number analysis (n=477).
Figure 19:
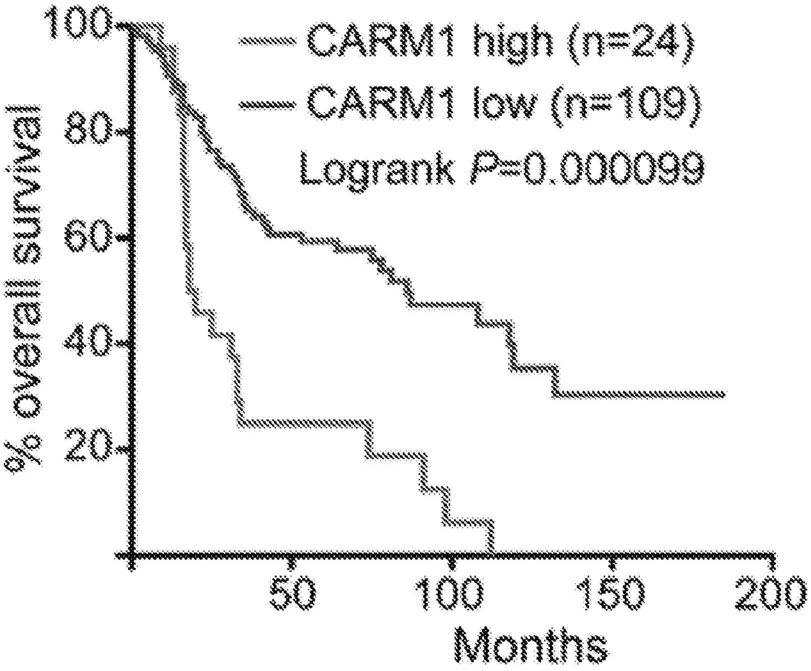
FIG. 19 illustrates overall survival of EOC patients with high or low CARM1 expression in an EOC microarray database. The cutoff expression level was statistically determined by a continuous expression model.

Analysis of high-throughput genetic profiles from The Cancer Genomics Atlas (TCGA) revealed amplification of CARM1 in ~10% of high-grade serous ovarian carcinomas (HGSOC) (FIG. 14) (Cancer Genome Atlas Research N. *Nature* (2011) 474:609-15). Consistently, CARM1 was expressed at a higher level in laser capture and microdissected HGSOCs compared with normal human ovarian surface epithelial (HOSE) cells (FIG. 15) (Mok et al. *Cancer Cell* (2009) 16:521-532). In addition, recent evidence indicates that the majority of HGSOC likely develops from the fallopian tube fimbriae epithelium (FTE) (see, e.g., Bowtell et al. *Nat Rev Cancer* (2015) 15:668-79 and Dubeau et al. *Ann Oncol.* (2013) 24 Suppl 8, viii28-viii35). Indeed, CARM1 was also expressed at a higher level in laser capture and microdissected HGSOCs compared with normal human fallopian tube epithelial (FTE) cells (FIG. 16) (Tone et al. *Clin Cancer Res.* (2008) 14:4067-78). Likewise, CARM1 was expressed at higher levels in a number of EOC cell lines compared with either FTE or HOSE cells (FIG. 17). Interestingly, CARM1 amplification and BRCA 1/2 mutations do not typically occur in the same tumor (FIG. 14) (Cancer Genome Atlas Research N. *Nature* (2011) 474:609-15). Consistent with its oncogenic role in EOC, CARM1 amplification or high expression predicted a shorter overall survival in TCGA HGSOC database and an independent EOC patient cohort based on gene expression profiling (FIGS. 18 and 19). Thus, CARM1 is amplified in EOC, and its amplification/high expression correlates with a poor overall survival in EOC patients.

Figure 20:
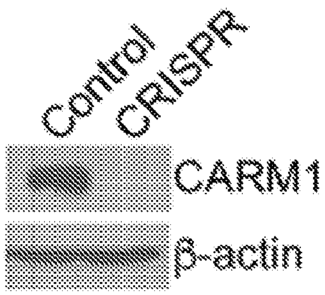
FIG. 20 illustrates expression of CARM1 and a loading control β-actin in CARM1 and a loading control β-actin in CARM1 high parental and CRISPR-mediated CARM1 knockout (KO) A1847 cells.
Figure 21:
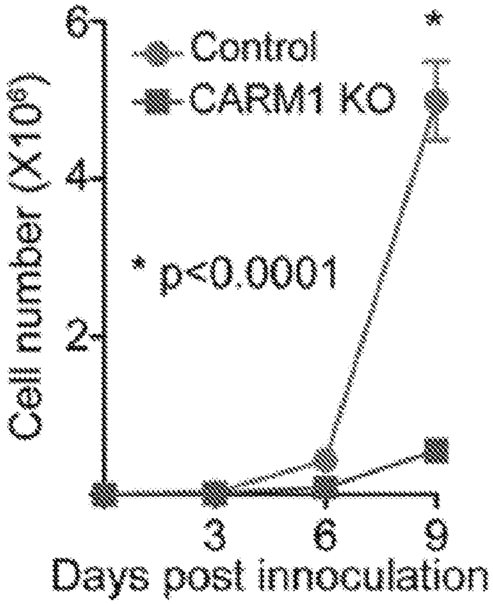
FIG. 21 illustrates growth curves of parental control and CARM1 knockout A1847 cells. Mean of three independent experiments with SEM.
Figure 22:
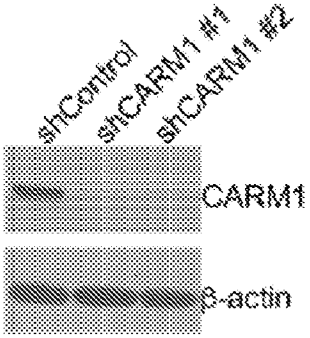
FIG. 22 illustrates the expression of CARM1 in A1847 cells expressing the indicated shCARM1 or controls.
Figure 23:
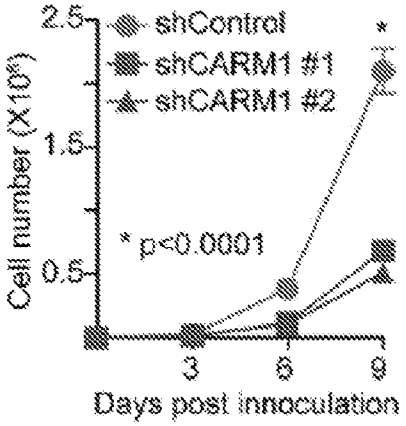
FIG. 23 illustrates growth curves of control and CARM1 knockdown A1847 cells. Mean of three independent experiments with standard deviation.
Figure 24:
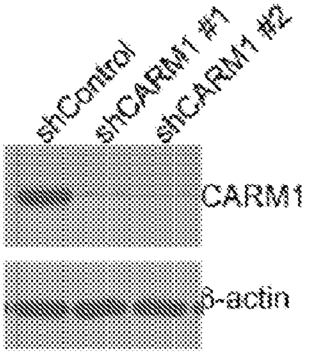
FIG. 24 illustrates the expression of CARM1 in high OVCAR10 EOC cells expressing the indicated shCARM1 or controls.
Figure 25:
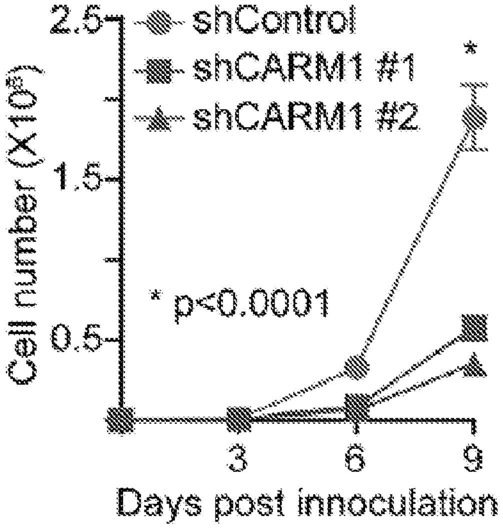
FIG. 25 illustrates growth curves of control and CARM1 knockdown high OVCAR10 EOC cells. Mean of three independent experiments with standard deviation.

Towards understanding the role of CARM1 in EOC, a CARM1 knockout (CARM1 KO) clone was generated in CARM1-high A1847 cells using the CRISPR methodology (FIG. 20). Consistent with CARM1 's growth-promoting role reported in other cancer types (Yang et al. *Nat Rev Cancer* (2013) 13:37-50), CARM1 KO A1847 cells exhibited a decrease in growth compared with parental controls (FIG. 21). Similar observations were made with shRNA-mediated CARM1 knockdown in CARM1-high EOC cell lines such as OVCAR10 and A1847 (FIGS. 22-25). Thus, CARM1 inhibition suppresses the growth of EOC cells.

EZH2 Inhibitors Selectively Suppress the Growth of CARM1-High Cells.

Figure 26:
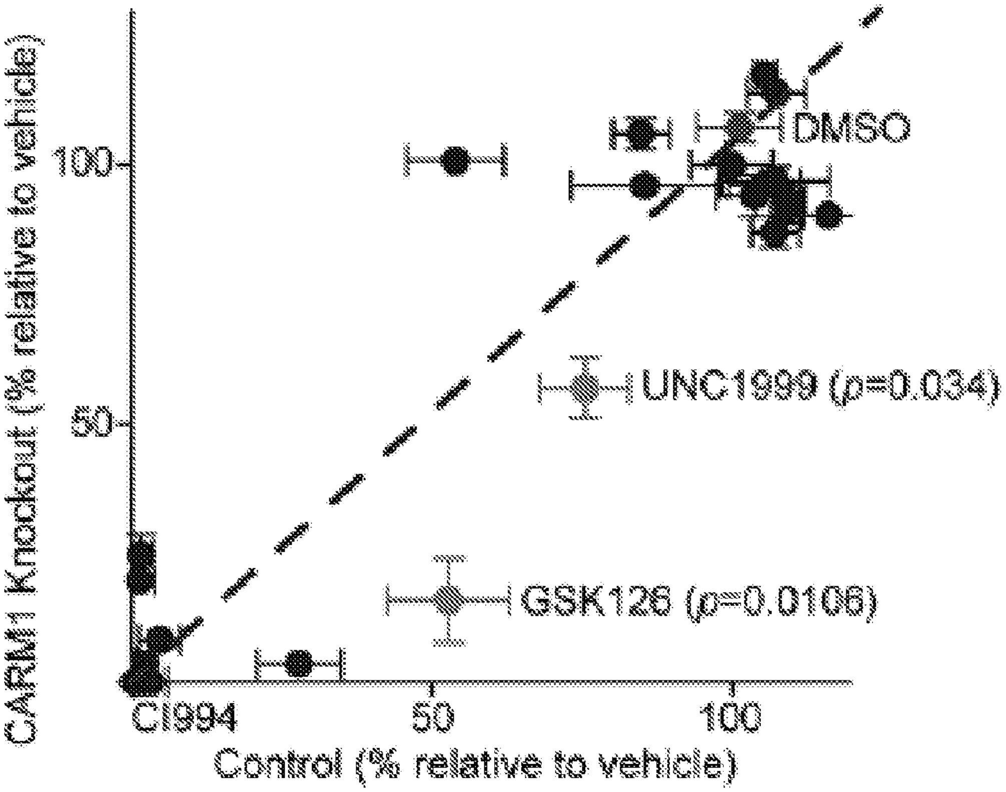
FIG. 26 illustrates that CARM1-expressing cells are selectively sensitized to EZH2 inhibitors. Equal number of parental control or CARM1 knockout A1847 cells were plated and treated with each of the 23 individual epigenetic inhibitors for 14 days. The media with the inhibitors was refreshed every 3 days. Cell growth was quantified as integrated density using NIH Image J software. Quantification of the average integrated density graphed as a scatter plot. The X-axis indicates the relative growth of treated CARM1 high parental A1847 cells compared with DMSO vehicle controls. Y-axis indicates the relative growth of treated CARM1 knockout A1847 cells compared with DMSO vehicle controls. n=4; and error bars represents SEM.
Figure 28:
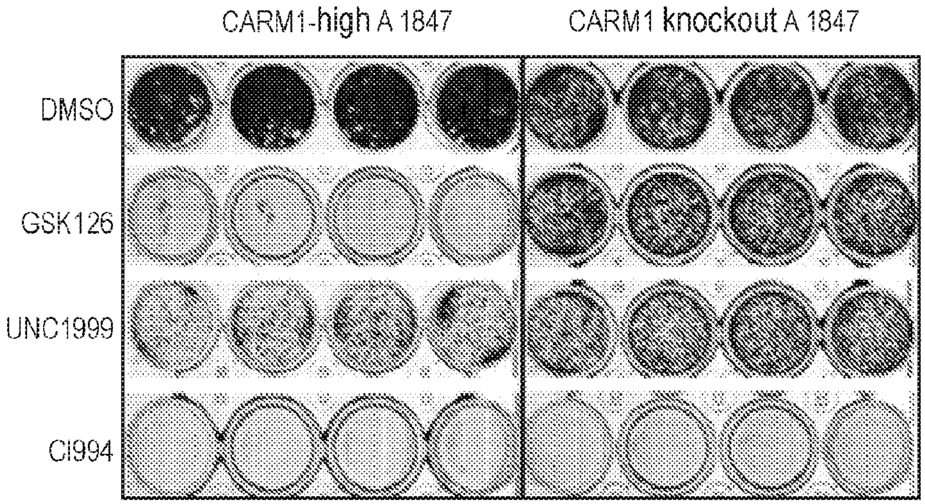
FIG. 28 illustrates representative images of colonies formed by the cells treated with the indicated inhibitors. GSK126 and UNC1999 representative positive hits from the screen. Note that CI994 was used a negative control that showed no difference between parental and CARM1 knockout cells.
Figure 29:
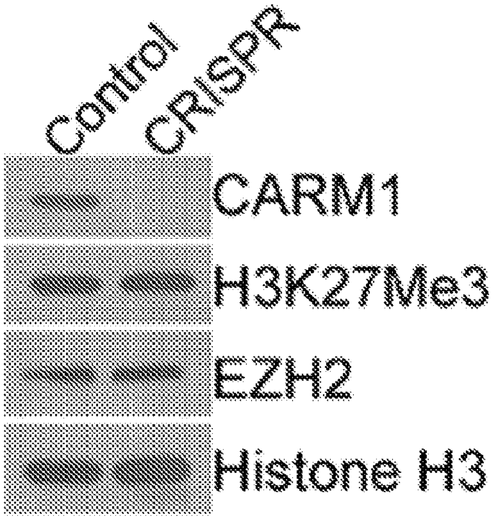
FIG. 29 illustrates the expression of CARM1, H3K27Me3, EZH2, and H3 in parental control and CARM1 knockout A1847 cells.
Figure 30:
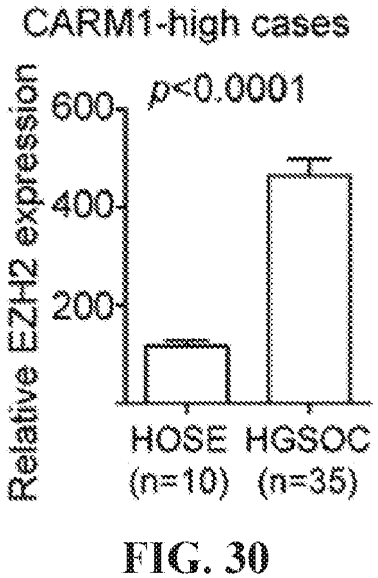
FIG. 30 illustrates relative expression of EZH2 in human ovarian surface epithelial (HOSE, n=10) cells and laser capture-microdissected high-grade serous ovarian carcinoma (LCM HGSOC, n=35) with high CARM1 expression.
Figure 31:
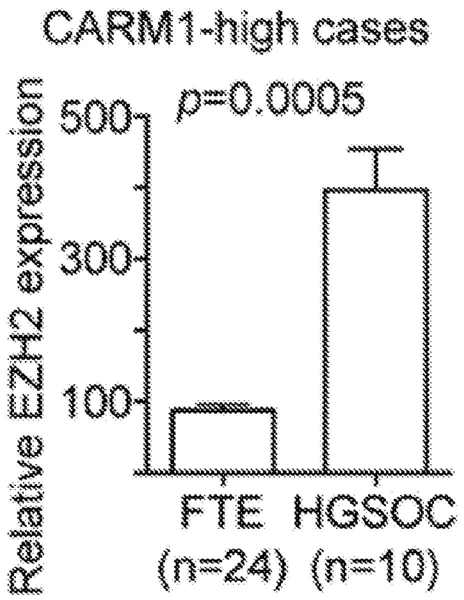
FIG. 31 illustrates relative expression of EZH2 in fallopian tube epithelial cells (n=24) and LCM HGSOC (n=10) with high CARM1 expression.

CARM1 asymmetrically dimethylates substrates involved in epigenetic gene transcription (Yang et al. *Nat Rev Cancer* (2013) 13:37-50). This suggests that epigenetic mechanisms play a key role in mediating the oncogenic activity of CARM1. Thus, an unbiased evaluation was performed of a set of 23 small molecule epigenetic inhibitors (Bitler et al. *Nature Medicine* (2015) 21:231-8). Each individual inhibitor was evaluated for its ability to selectively suppress the growth of CARM1-expressing cells compared with CARM1 KO cells. Interestingly, both of the EZH2 inhibitors in the set (namely GSK126 and UNC1999) showed selectivity against CARM1-expressing cells (FIGS. 26 and 27) (see, e.g., McCabe et al. *Nature* (2012) 492:108-12 and Konze et al. *ACS Chem Biol.* (2013) 8:1324-34). This is not due to a reduced proliferation of CARM KO cells because: (1) a number of small molecule inhibitors were equally effective in suppressing the growth of both CARM-expressing and KO cells (e.g., CI994, FIG. 28); and (2) the data was normalized to the growth of vehicle-treated CARM1-expressing or KO cells to control for variation in cell growth. The observed CARM1-dependent selectivity by EZH2 inhibitors was not due to changes in EZH2 levels because its expression was not altered and levels of its enzymatic product H3K27Me3 were not changed by CARM1 knockout (FIG. 29). However, EZH2 is overexpressed in CARM-high primary HGSOC and cell lines compared to either HOSE cells or FTE cells (FIGS. 17, 30, and 31) (Cancer Genome Atlas Research N. *Nature* (2011) 474:609-15 and Tone et al. *Clin Cancer Res*. (2008) 14:4067-78).

Figure 32:
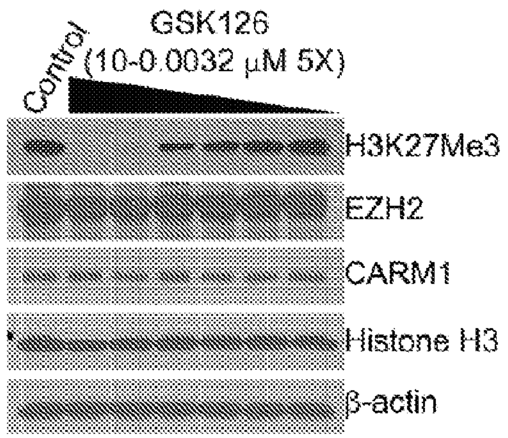
FIG. 32 illustrates that the EZH2 inhibitor GSK 126 decreases H3K27Me3 levels in a dose-dependent manner. A1847 cells were treated with the indicated concentrations of GSK126 for 72 hours and examined for expression of the indicated proteins by immunoblot. Expression of histone H3 and β-actin was used as a loading control.
Figure 33:
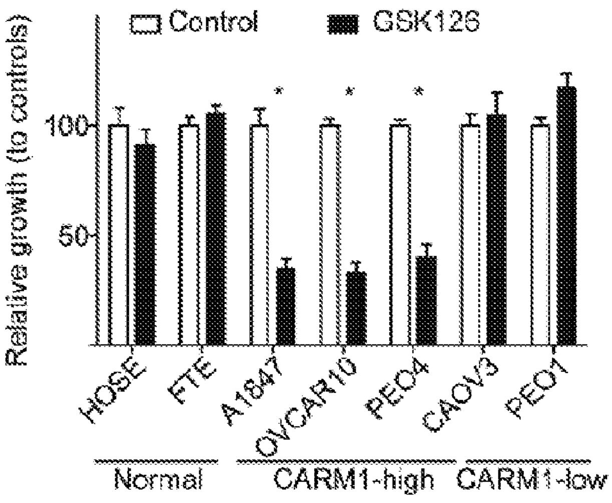
FIG. 33 illustrates relative growth of the indicated HOSE, FTE, and EOC cancer cell lines with high or low CARM1 expression treated with 10 μM GSK126 or vehicle in a colony formation assay as determined by NIH Image J quantification.
Figure 34:
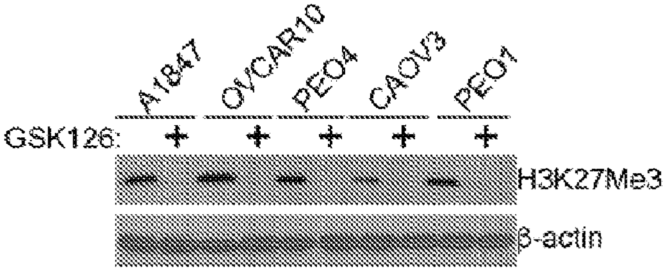
FIG. 34 illustrates expression of H3K27Me3 in the indicated EOC cell lines with high or low CARM1 expression treated with or without 10 μM GSK126. Expression of β-actin was used as a loading control.
Figure 35:
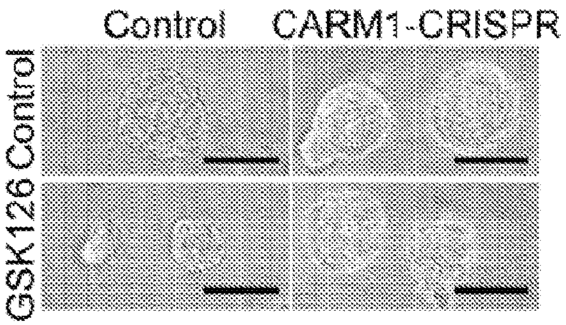
FIG. 35 illustrates representative images of acini formed by indicated cells treated with or without 10 μM GSK126 in 3D cultures using Matrigel extracelluar matrix for 12 days. Scale Bars=50 of measurable units (AU) using the NIH Image J Software.
Figure 36:
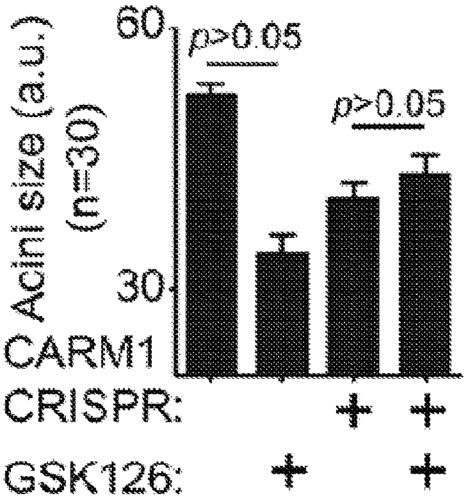
FIG. 36 illustrates the quantification of the diameter of acini formed by the indicated cells with or without 10 μM GSK 126 treatment in 3D culture for 12 days. (N=30 acini per sample).
Figure 37:
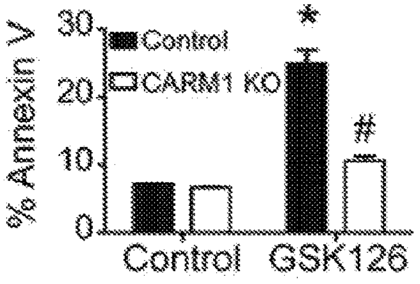
FIG. 37 illustrates control parental and CARM1 knockout A1847 cells were treated with 10 μM GSK126 or vehicle for 7 days. Percentage of Annexin V positive apoptotic cells was quantified. *p<0.001 and #p>0.05.
Figure 38:
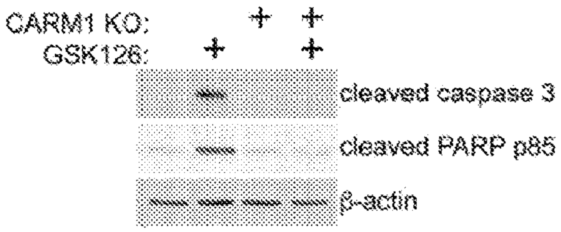
FIG. 38 illustrates levels of cleaved caspase 3 and cleaved PARP in control parental and CARM1 knockout A1847 cells treated with 10 μM GSK126 for 7 days. Expression of β-actin was used as a loading control.
Figure 39A:
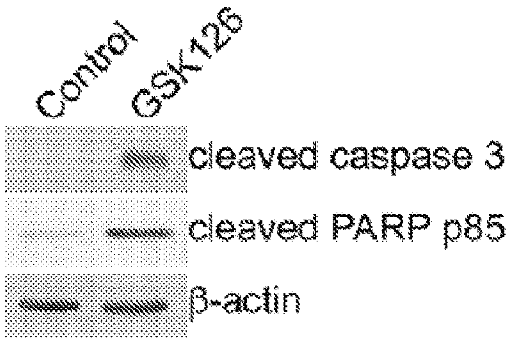
FIG. 39A illustrates the expression of apoptosis markers cleaved in CARM1 high OVCAR10 cells as a result of treatment with GSK126. CARM1 high OVCAR10 cells were treated with 10 μM GSK 126 or vehicle control for 7 days. The expression of apoptosis markers cleaved caspase 3 and cleaved PARP were determined by immunoblot. Expression of β-actin was used as a loading control.

These studies focus on GSK 126. It was determined that 10 μM GSK 126 was sufficient to inhibit >95% of the enzymatic activity of EZH2 as indicated by the decrease in H3K27Me3 levels (FIG. 32). Note that EZH2 inhibition did not affect the expression of CARM1 (FIG. 32). GSK126 did not affect EZH2 protein levels but instead selectively inhibited its methyltransferase activity as evidenced by a dose-dependent decrease in H3K27Me3 levels (FIG. 32). Thus, a concentration of 10 μM GSK126 was used for subsequent studies. Validating the pharmacological screen, there was a correlation between CARM1 expression levels and cellular response to GSK 126 in a panel of EOC cell lines (FIGS. 17, 33, and 34). Notably, GSK126 did not affect the growth of either HOSE or FTE cells (FIG. 33). Similar results were obtained in CARM1-high parental and CARM1 KO cells in both conventional 2D and 3D cultures using Matrigel extracellular matrix (FIGS. 35 and 36). EZH2 is expressed at comparable levels in normal controls and CARM1-low EOC cells that did not respond to GSK126 such as CAOV3 and PEO1 (FIGS. 17 and 33), indicating that the observed selectivity was not due to EZH2 upregulation alone. Consistent with the observed growth inhibition, markers of apoptosis were induced by EZH2 inhibition in a CARM1-dependent manner (e.g., FIGS. 37, 38, and 39A). These data point to sensitivity to EZH2 inhibitors as a unique and exploitable therapeutic vulnerability in CARM1-high EOCs.

Figure 39B:
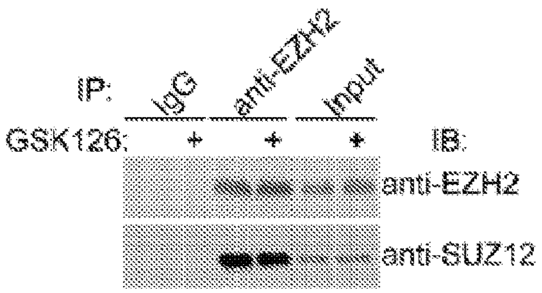
FIG. 39B illustrates that EZH2 inhibitor GSK126 did not affect PRC2 subunits EZH2 and SUZ12 interaction in CARM1 high A1847 cells. A1847 cells were treated with 10 μM GSK126 or vehicle control for 7 days. The cells were subjected to immunoprecipitation (IP) analysis by using an anti-EZH2 antibody. The immunoprecipitated product was examined for EZH2 and SUZ12 expression by immunoblot. An isotype-matched IgG was used as a control.
Figure 40:
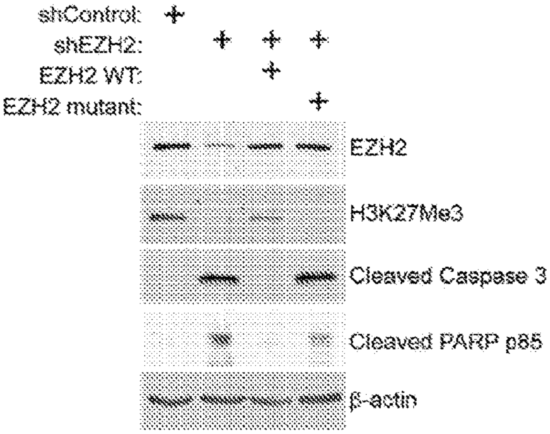
FIGS. 40 to 43 illustrate CARM1-high A1847 cells were infected with a lentivirus encoding shEZH2 targeting the 3' untranslated region (UTR) of the human EZH2 gene together with a retrovirus encoding wild-type EZH2 (WT) or a SET domain-deleted EZH2 mutant (EZH2 ΔSET). Drug-selected cells were examined for EZH2, H3K27Me3, apoptosis markers cleaved caspase 3 and cleaved PARP p85, and loading control (β-actin) by immunoblot (FIG. 40), quantified for Annexin positive apoptotic cells by FACS (FIG. 41), subjected to a colony formation assay (FIG. 42), and quantified for the relative cell growth based on colony formation using NIH Image J (FIG. 43). Means of three independent experiments with SEM are shown.
Figure 41:
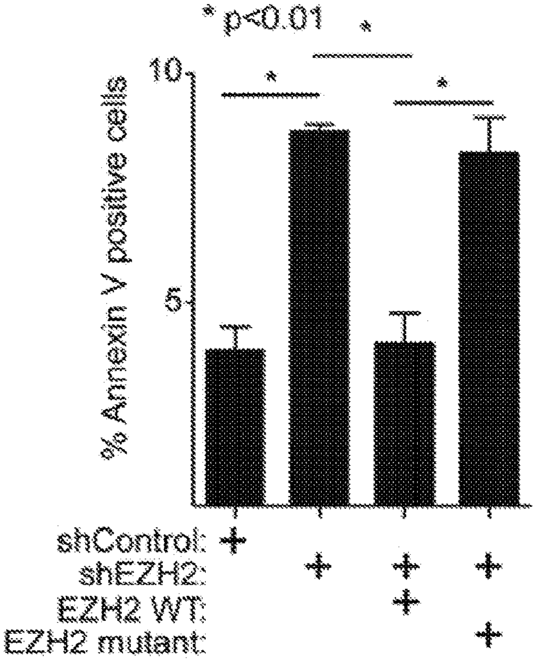
Figure 42:
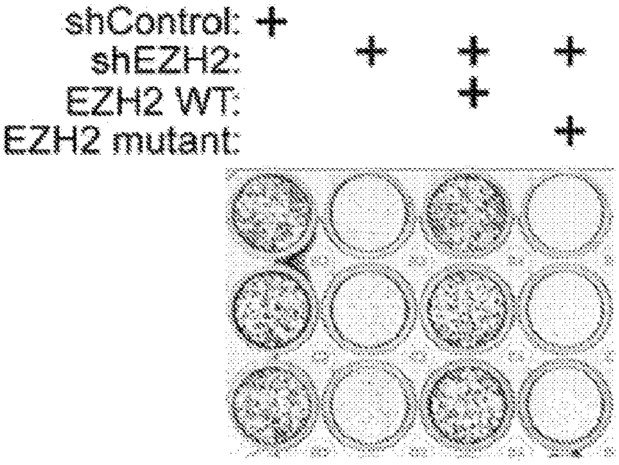
Figure 43:
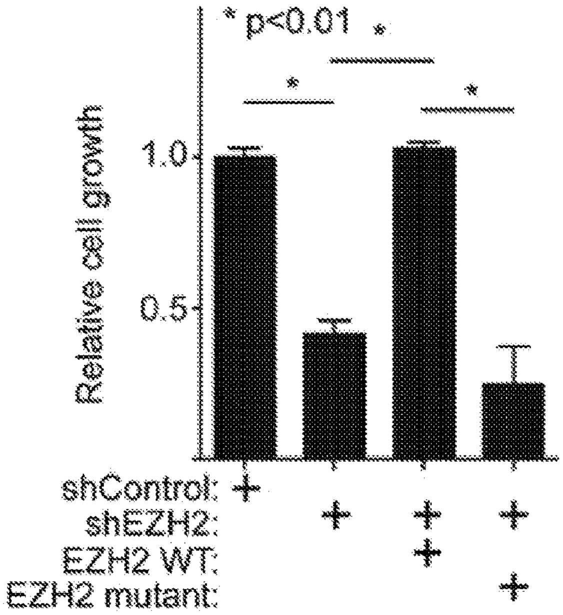

To limit the potential off-target effects and validate that the observed effects were due to inhibition of EZH2's methyltransferase activity, genetic rescue experiments were performed. Indeed, apoptosis induced by EZH2 knockdown could be rescued by wild-type EZH2 but not by a mutant with inactivated catalytic activity (FIGS. 40 and 41). Consistently, the cell growth inhibition induced by EZH2 knockdown was rescued by wild-type EZH2 but not by a catalytically inactive EZH2 mutant (FIGS. 42 and 43). Evidence suggests that EZH2 inhibitor can also affect cell growth by destabilizing PRC2 complex in a catalytic activity-independent manner. Notably, the EZH2 inhibitor GSK126 did not weaken the interaction between PRC2 subunits EZH2 and SUZ12 (FIG. 39B), supporting the notion that the observed selectivity against CARM1 was not due to destabilization of PRC2 complex. Together, and without being limited to any one theory, it has been concluded that the observed selectivity against CARM1 by EZH2 inhibitor is due to inhibition of its methyltransferase activity.

CARM1 Promotes the Silencing of EZH2 Target Tumor Suppressor Genes.

Figure 44:
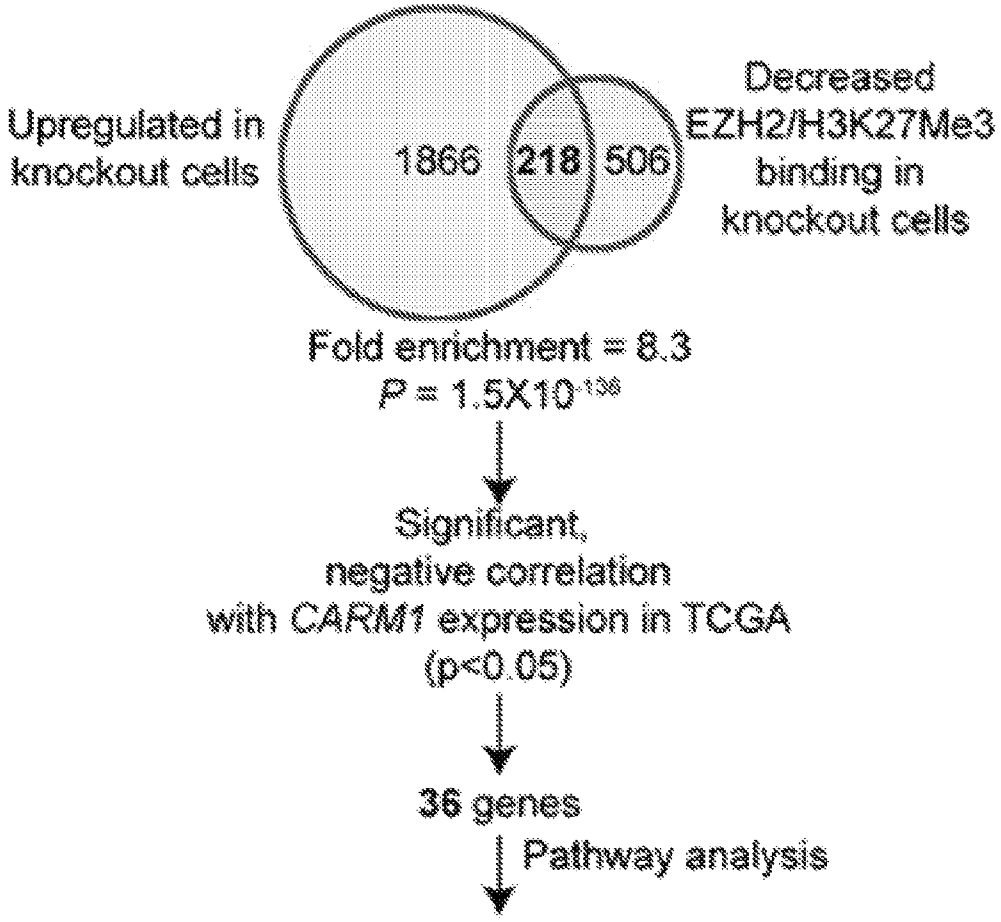
FIG. 44 illustrates an experimental strategy used to identify CARM1-regulated, clinically relevant EZH2/H3K27Me3 target genes. Ingenuity Pathway Analysis revealed that the top pathway enriched for the identified CARM1-regulated EZH2/H3K27Me3 target genes was apoptosis. Specifically, 19 of the 36 identified genes (including DAB2, DLC1, and NOXA) are known to promote apoptosis (the full list is available in FIG. 49).
Figure 45:
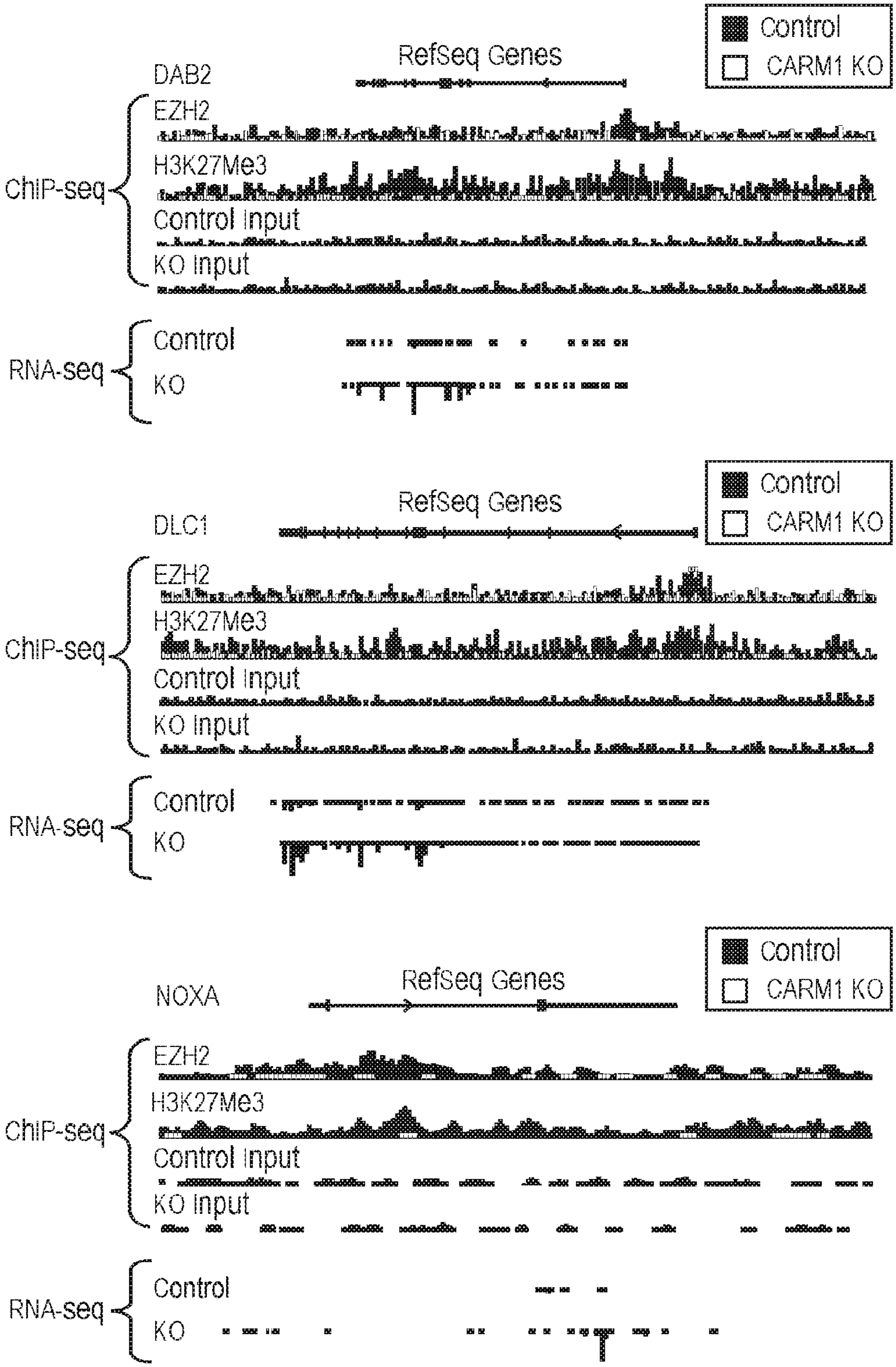
FIG. 45 illustrates examples of EZH2 and H3K27Me3 ChIP-seq and RNA-seq tracks of the newly identified CARM1-regulated EZH2/H3K27Me3 target genes in the indicated parental control and CARM1 knockout A1847 cells.
Figure 46:
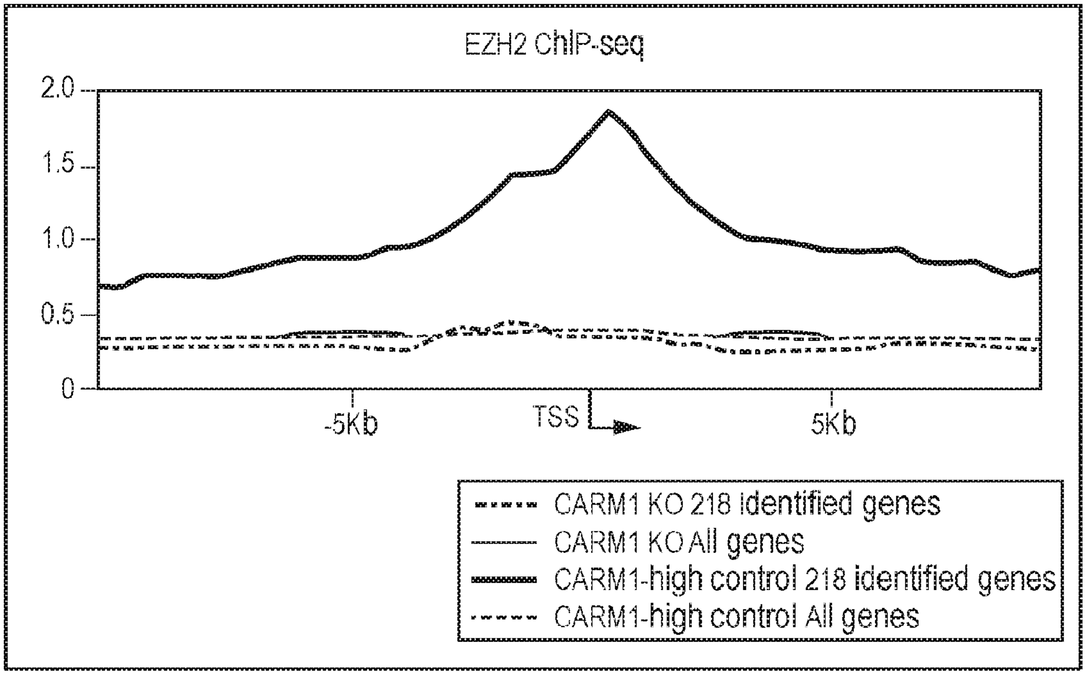
FIGS. 46 to 48 illustrate that EZH2/H3K27Me3 target genes are enriched in genes upregulated by CARM1 knockout in A1847 cells.
Figure 47:
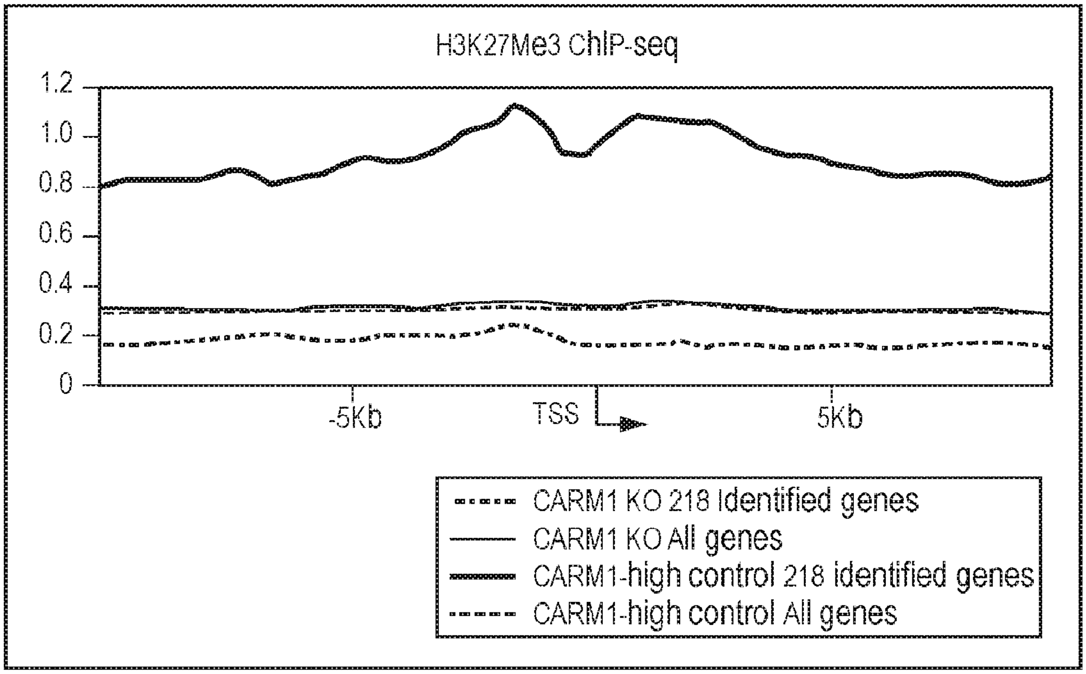
Figure 48:
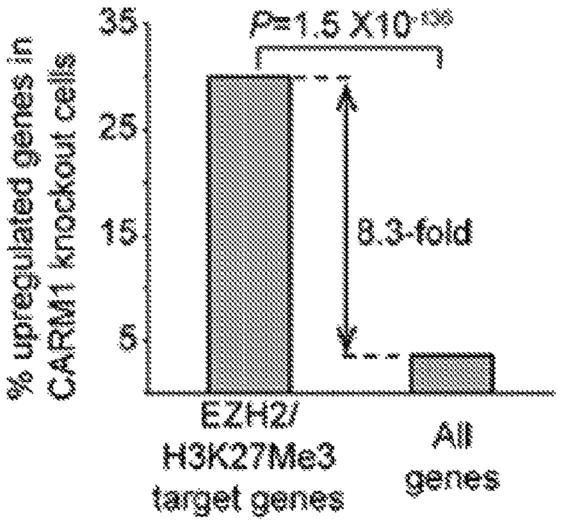

To explore the mechanistic basis of the selectivity against EZH2 inhibitor, RNA-deep sequencing (RNA-seq) was performed in parental control and CARM1 KO cells (FIG. 44). To identify direct EZH2 target genes that are regulated by CARM1, EZH2 and H3K27Me3 chromatin immunoprecipitation were performed followed by deep sequencing (ChIP-seq) analysis in control and CARM1 KO cells (FIG. 44). Since CARM1 may promote EZH2-dependent gene silencing, the genomic loci were focused upon that showed a decrease in association with EZH2/H3K27Me3 in CARM1 KO cells compared with controls (e.g., FIGS. 44 and 45). Cross-referencing RNA-seq and ChIP-seq data (GEO access number: GSE95645) revealed a list of 218 direct EZH2/H3K27Me3 target genes that were downregulated by CARM1 (>3-fold) (FIGS. 44, 46, and 47). This represents a 8.3-fold enrichment of EZH2/H3K27Me3 target genes among the 2084 genes upregulated at least 3-fold in CARM1 KO cells compared with parental controls ($P=1.5\times10^{-136}$) (FIG. 48). Finally, the list of 218 direct EZH2/H3K27Me3 target genes were cross-referenced with 528 TCGA high-grade serous ovarian carcinomas gene expression profiles and identified genes that negatively correlated with CARM1 expression in these cases (FIG. 44). These prioritizations led to a list of 36 EZH2 direct target genes that negatively correlated with CARM1 expression (FIG. 44). Pathway analysis revealed that the top functional pathway enriched in these genes was apoptosis ($n=19$, $P=2.6\times10^{-6}$) (FIGS. 44 and 49). Notably, three of the ranked apoptosis-regulating genes (DAB2 (He et al. *J. Biol Chem*. (2001) 276:26814-8), DLC1 (Barras et al. *Cancer Metastasis Rev*. (2014) 33:87-100 and Zhou et al. *Oncogene* (2004) 23:1308-13) and NOXA (Ploner et al. *Oncogene* (2008) 27 Suppl 1: S84-92)) were known tumor suppressors that are implicated in suppressing proliferation and promoting apoptosis (FIG. 45), i.e., the phenotypes observed when CARM1 was knocked out or EZH2 activity was inhibited with GSK126 (see, e.g., FIGS. 15-21, 26, and 28-31).

Figure 50:
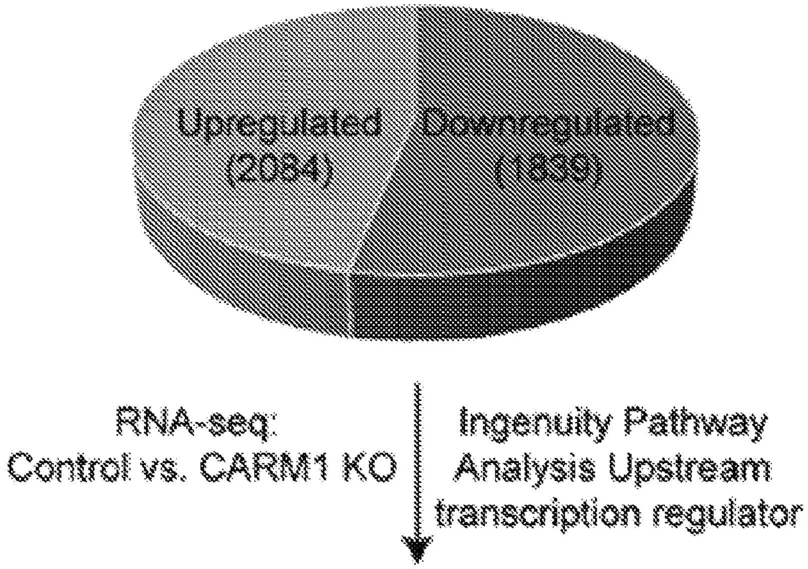
FIG. 50 illustrates differentially expressed genes in control parental and CARM1 knockout A1847 cells identified by RNA-seq (>3-fold) were subjected to Ingenuity Pathway Analysis for upstream regulators. The analysis revealed that SMARCA4 (also known as BRG1, a catalytic subunit of the SWI/SNF complex) was the top upstream regulator of these differentially expressed genes.
Figure 52:
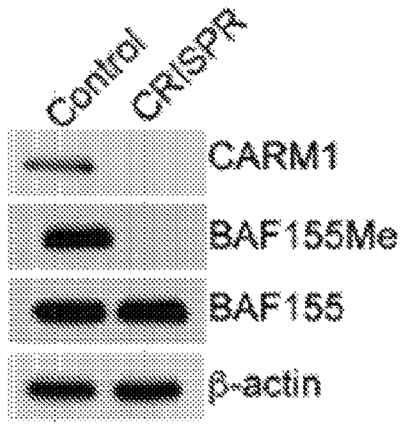
FIG. 52 illustrates the expression of CARM1, BAF155, and BAF155Me in control parental and CARM1 knockout A1847 cells. Expression of β-actin was used as a loading control.
Figure 53:
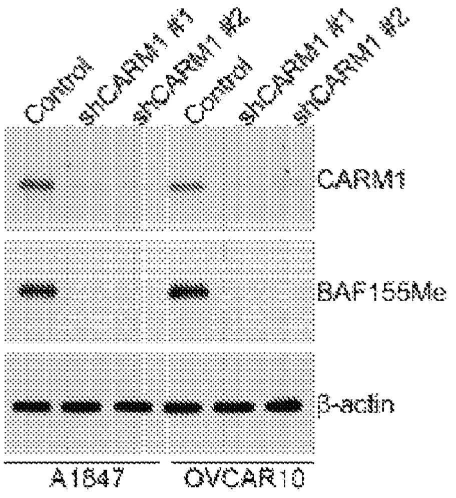
FIGS. 53 and 54 illustrate that CARM1 regulates BAF155Me and EZH2 inhibition did not affect BAF155Me levels.
Figure 54:
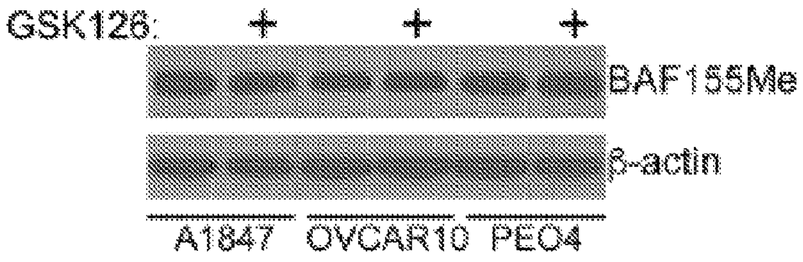

In parallel, Ingenuity Pathway Analysis was performed for the upstream transcription factor that regulates the genes differentially expressed in parental control and CARM1 KO cells. The top upstream transcription regulator identified was the SMARCA4 (also known as BRG1), the catalytic subunit of the SWI/SNF complex ($P=1.22\times10^{-30}$) (FIGS. 50 and 51). Notably, inhibition of EZH2 activity is known to be synthetically lethal with inactivation of the SWI/SNF complex due to antagonistic regulation of the same set of genes by the EZH2/PRC2 and the SWI/SNF complexes (Kadoch et al. *Sci Adv*. (2015) 1: e1500447). CARM1 methylates the R1064 residue of BAF155, a core subunit of the SWI/SNF complex (Wang et al. *Cancer Cell* (2014) 25:21-36). Indeed, the observed changes in selectivity against CARM1 KO or knockdown cells correlated with the decrease in R1064 methylated BAF155 (BAF155Me) levels (see FIGS. 50, 52, and 53). However, EZH2 inhibition did not affect BAF155Me levels (FIG. 54). Together, these data suggest that CARM1 may promote EZH2-mediated silencing by altering the antagonism between PRC2 and SWI/SNF complex via BAF155Me.

CARM1 Regulates Antagonism Between BAF155 and EZH2 by Methylating BAF155.

Figure 55:
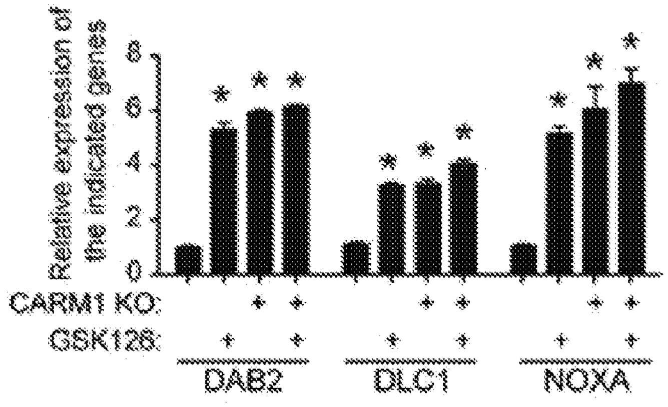
FIG. 55 illustrates the relative expression of DAB2, DLC1, and NOXA in parental control and CARM1 knockout A1847 cells that were treated with 10 μM GSK126 or vehicle controls. mRNA expression of the indicated genes was determined by qRT-PCR. *$p<0.002$ compared with parental controls.
Figure 56:
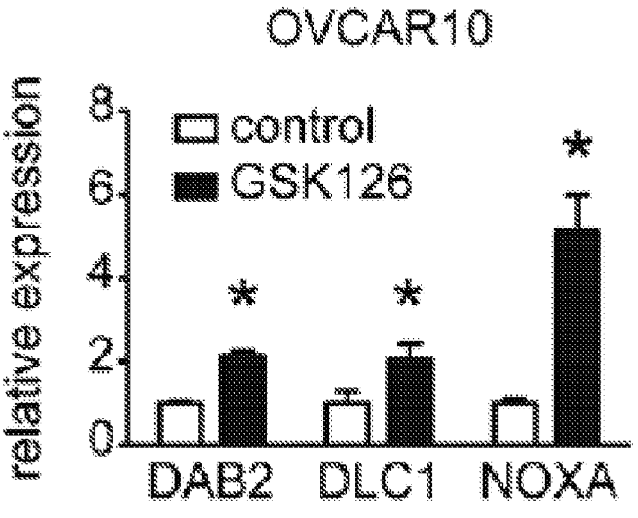
FIG. 56 illustrates the relative expression of DAB2, DLC1, and NOXA in CARM1 high OVCAR10 cells treated with 10 μM GSK 126 or vehicle control for 7 days. Expression of the indicated BAF155/EZH2 target genes was determined by qRT-PCR. *$p<0.001$. Mean of three independent experiments with SEM.
Figure 57:
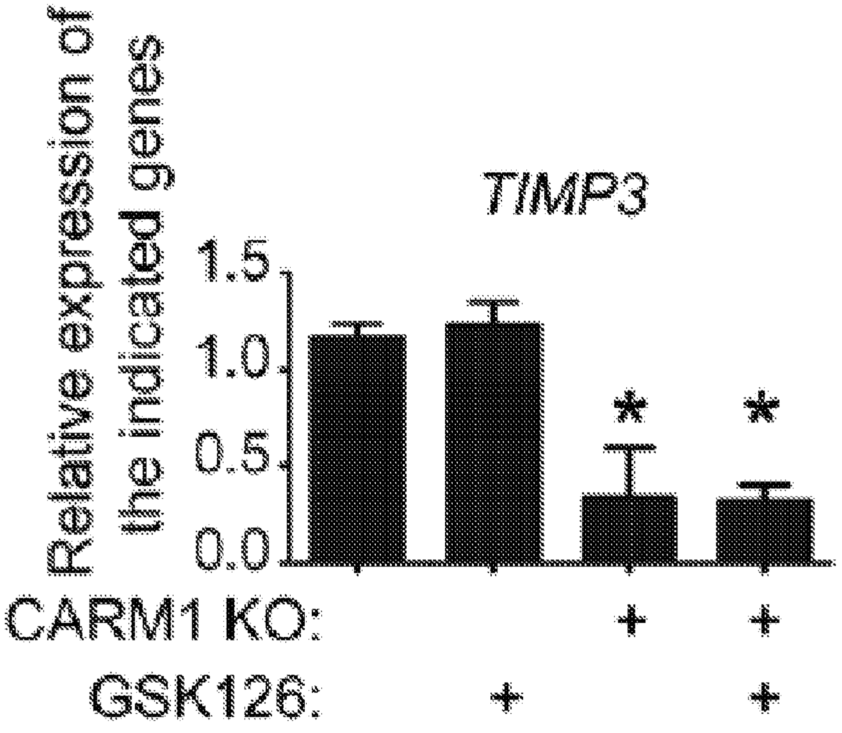
FIG. 57 illustrates the relative mRNA expression of BAF155Me target gene TIMP3, which was determined by qRT-PCR. Parental control and CARM1 knockout A1847 cells were treated with 10 μM GSK126 or vehicle controls. *$p<0.001$. Mean of three independent experiments with SEM.

A validation study was first performed to determine whether the identified genes were regulated by CARM1 and EZH2 inhibitor GSK126. Indeed, the expression of the identified genes was upregulated by either EZH2 inhibition by GSK126 treatment or CARM1 knockout or knockdown (FIGS. 55 and 56). Notably, GSK 126 treatment and CARM1 knockout did not appear to have additive effects on the expression of these genes (FIG. 55), indicating that they probably function in the same pathway to regulate the expression of these genes. As a control, known CARM1-regulated BAF155Me target genes such as the tumor suppressor TIMP3 (Wang et al. *Cancer Cell* (2014) 25:21-36) were downregulated by CARM KO but not by EZH2 inhibitor GSK126 (FIG. 57). This supports the notion that CARM1 promotes the silencing of EZH2/BAF155 target genes but mediates the expression of CARM1-regulated BAF155Me targeted genes in an EZH2-independent manner. Our results also suggest that EZH2 does not regulate BAF155Me target genes.

Figure 58:
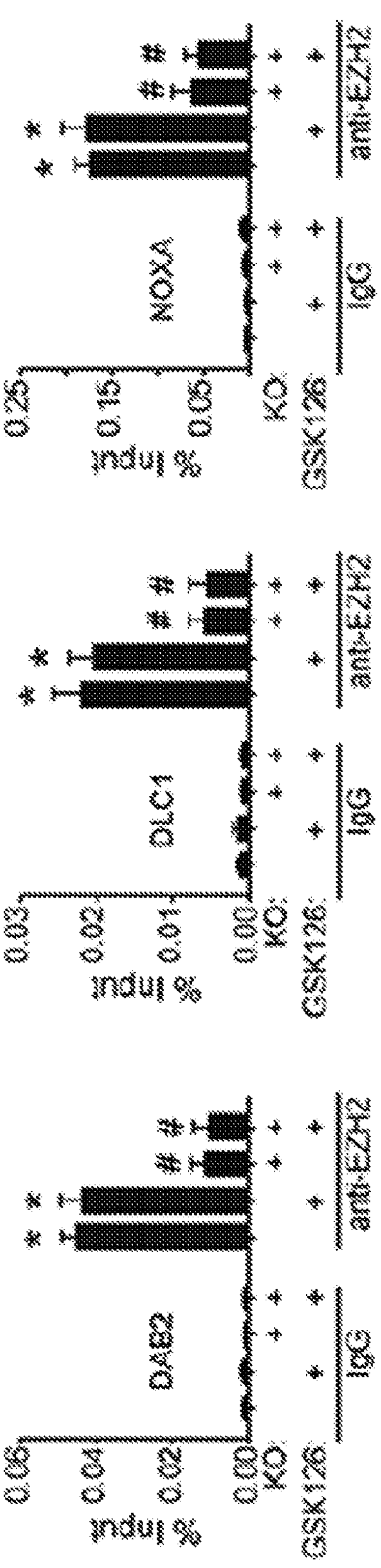
FIGS. 58 to 61 illustrate the results of a ChIP analysis using anti-EZH2 (FIG. 58), anti-H3K27Me3 (FIG. 59), anti-BAF155 (FIG. 60), or anti-RNA Pol II (FIG. 61) antibodies. An isotype matched IgG was used as a negative control. ChIP products were subjected to qPCR analysis using primers specific for the promoter regions of the human DAB2, DLC1, and NOXA genes. Data is representative of three independent experiments. *$p<0.001$ compared with IgG controls and #$p<0.001$ compared with parental controls.
Figure 59:
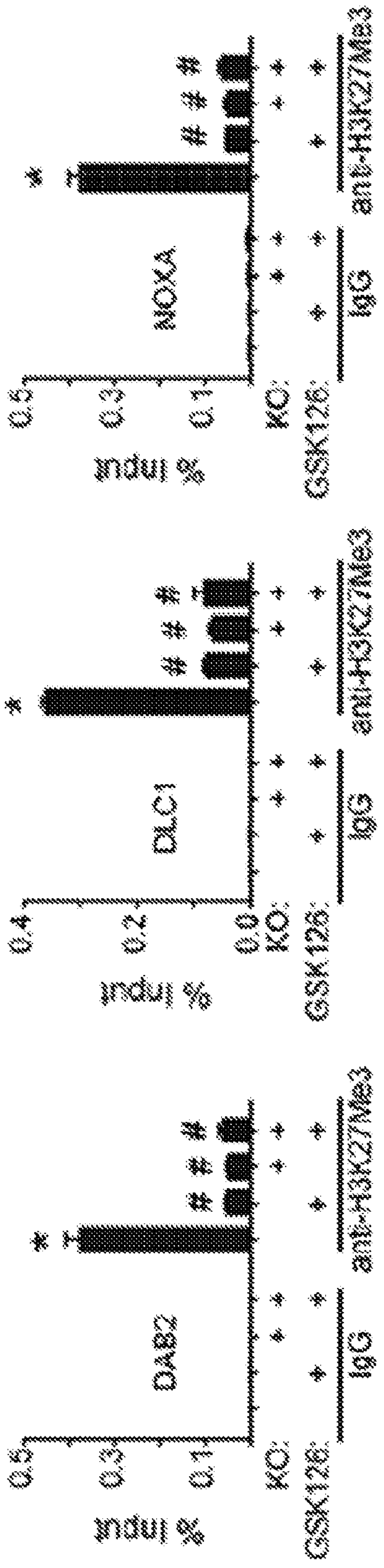
Figure 60:
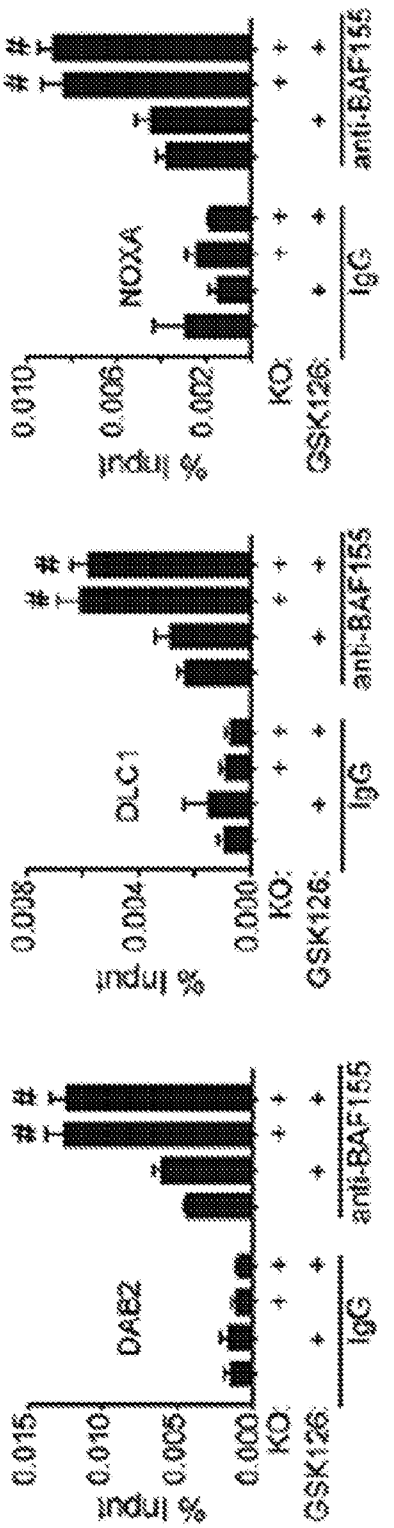
Figure 61:
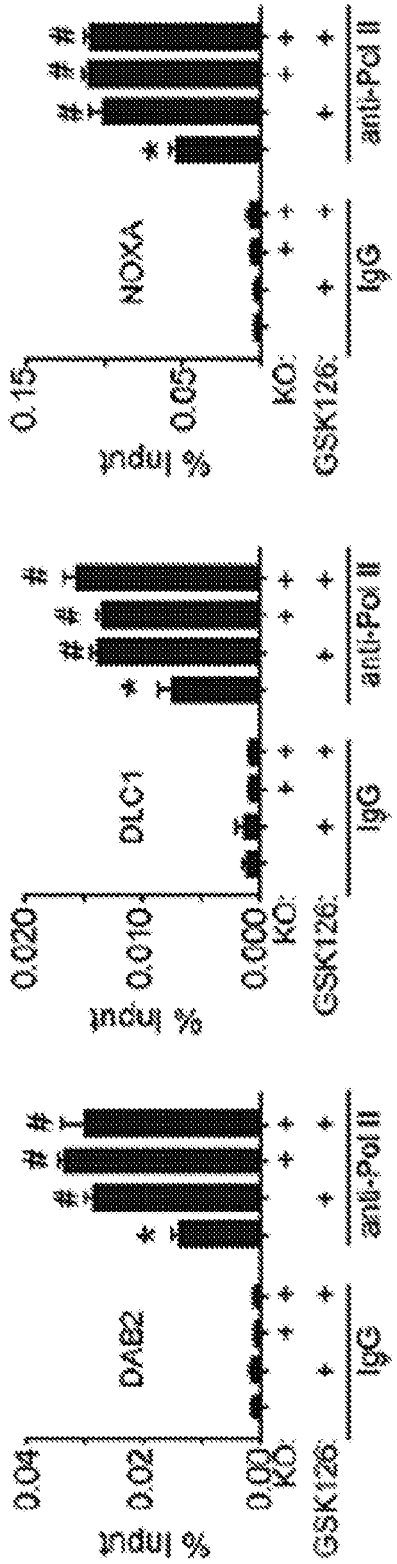
Figure 62:
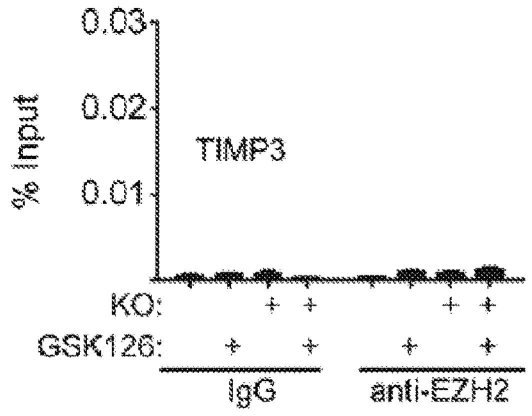
FIGS. 62 to 65 illustrate the results of a ChIP analysis in parental control and CARM1 knockout A1847 cells treated with 10 μM GSK 126 or vehicle controls. The cells were subjected to ChIP analysis using anti-EZH2 (FIG. 62), anti-H3K27Me3 (FIG. 63), anti-BAF155 (FIG. 64), or anti-RNA Pol II (FIG. 65) antibodies. An isotype-matched IgG was used as a negative control. ChIP products were subjected to qPCR analysis using primers specific for the promoter regions of the human TIMP3 genes. Mean of three independent experiments with SEM. *$p<0.001$ compared with controls.
Figure 63:
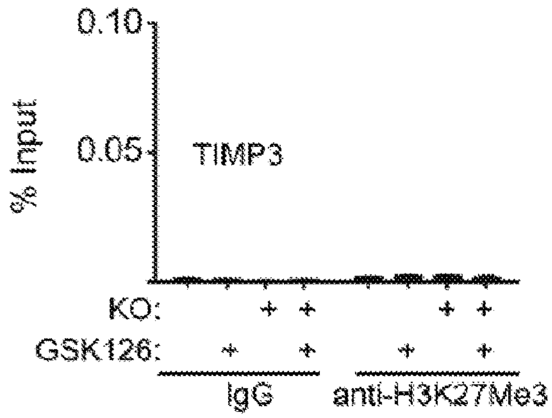
Figure 64:
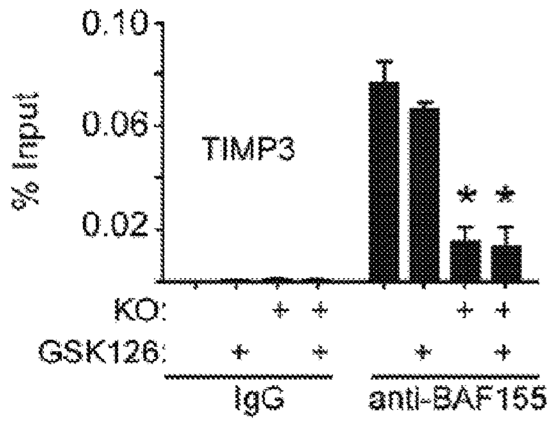
Figure 65:
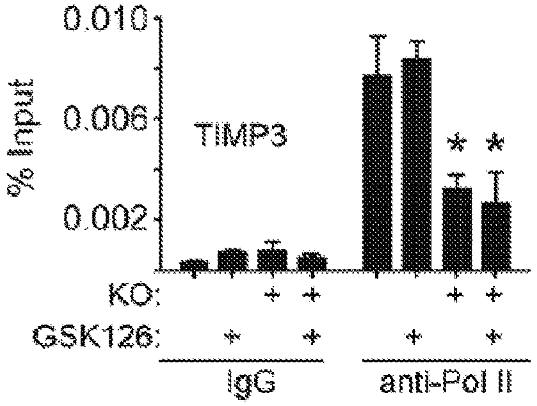
Figure 66:
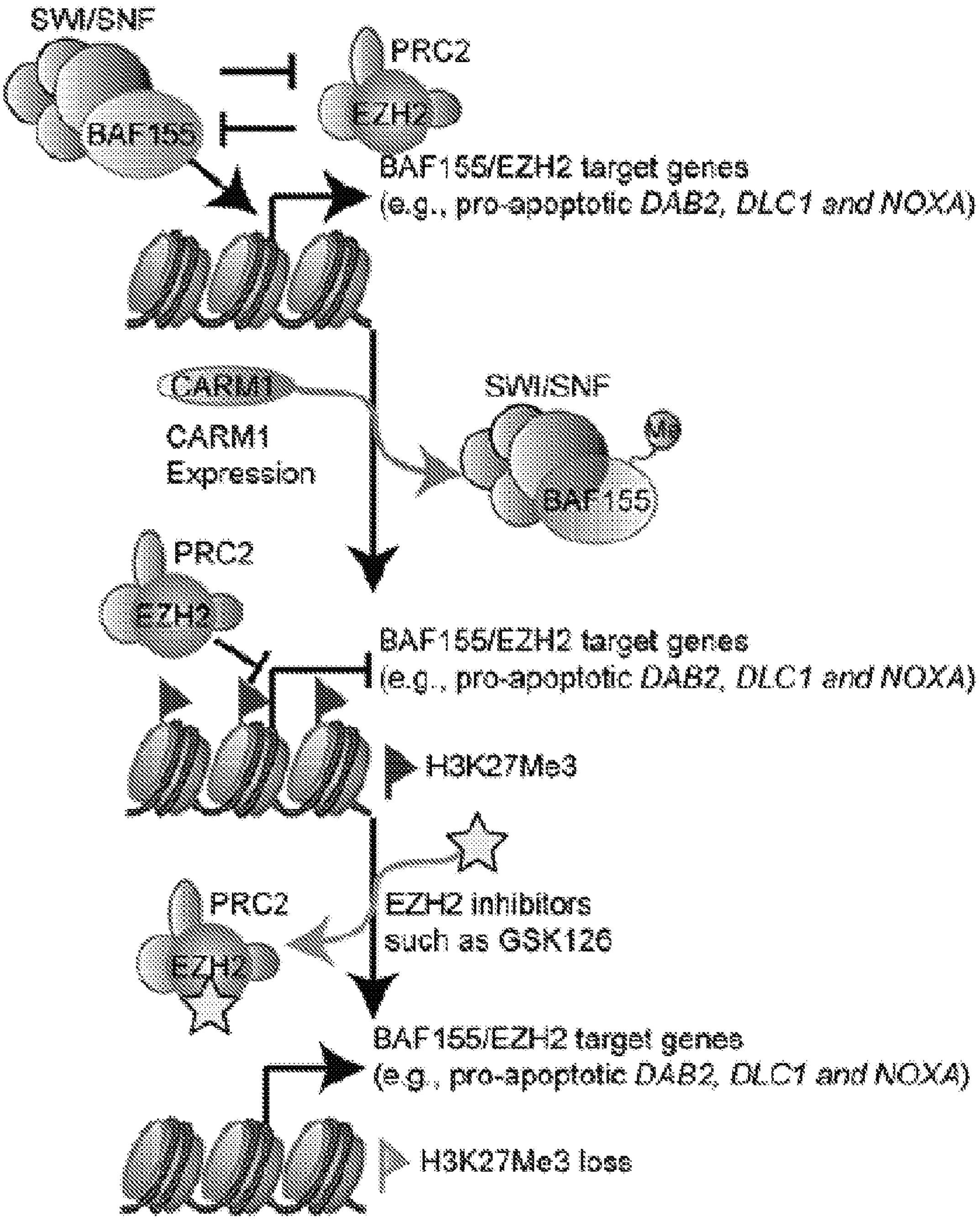
FIG. 66 illustrates a model proposed for the molecular basis of the CARM1-dependent effects of EZH2 inhibition. Without being limited to any one theory, CARM1 regulates the antagonism between the BAF155-containing SWI/SNF complex and the EZH2-containing PRC2 complex by methylating BAF155. This correlates with the silencing of the tumor-suppressive BAF155/EZH2 target genes due to displacement of the methylated BAF155 by EZH2. Expression of these genes can be restored by EZH2 inhibition. Error bars represent SEM p-values are from two-tailed t-test.

ChIP analysis validated that the association of EZH2 and its enzymatic product H3K27Me3 with these gene loci was indeed CARM1-dependent (FIGS. 58 and 59). EZH2 inhibitor decreased H3K27Me3 occupancy without affecting EZH2's association with its target genes (FIGS. 58 and 59). Importantly, CARM1 KO led to loss of EZH2 from these target gene loci and a corresponding increase in the association of BAF155 with these gene loci (FIG. 60). This result indicates that there is a switch from EZH2 to unmethylated BAF155 in these gene loci when CARM1 is knocked out. Finally, the association of RNA polymerase II (Pol II) with the gene loci correlated with changes in their expression (FIGS. 55 and 61). In contrast, there was no significant enrichment of either EZH2 or H3K27Me3 in the promoter of the CARM1-regulated BAF155Me target genes such as TIMP3 (Wang et al. *Cancer Cell* (2014) 25:21-36) (FIGS. 62 and 63). CARM1 KO but not EZH2 inhibitor GSK 126 treatment decreased the association of BAF155 and Pol II with the TIMP3 promoter (FIGS. 64 and 65). Since the antibody against BAF155Me was not suitable for ChIP analysis, BAF155Me occupancy of target genes could not be directly examined. Nevertheless, the data support a model that CARM1 promotes the silencing of EZH2/BAF155 target genes by displacing BAF155 via methylation, which then permits the occupancy of the target gene promoters by EZH2 and their consequent repression by H3K27Me3 (FIG. 66). In contrast, CARM1 mediates the expression of CARM1-regulated BAF155Me targeted genes in an F7.112-independent manner (FIG. 66). Thus, CARM1 regulates the antagonism between SWI/SNF and PRC2 through methylating BAF155 (FIG. 66).

Figure 67:
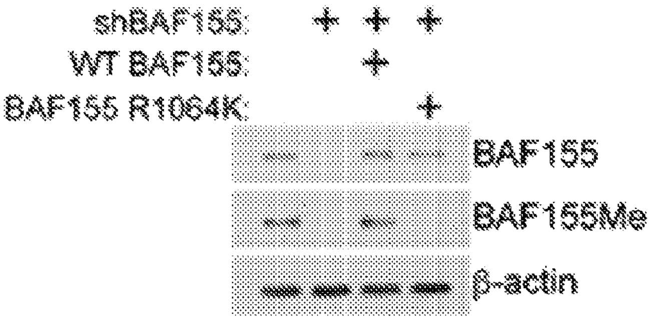
FIGS. 67 to 71 illustrate that CARM1-mediated R1064 BAF155 methylation displaces BAF155 with EZH2 at the promoters of EZH2/BAF155 target genes.
Figure 68:
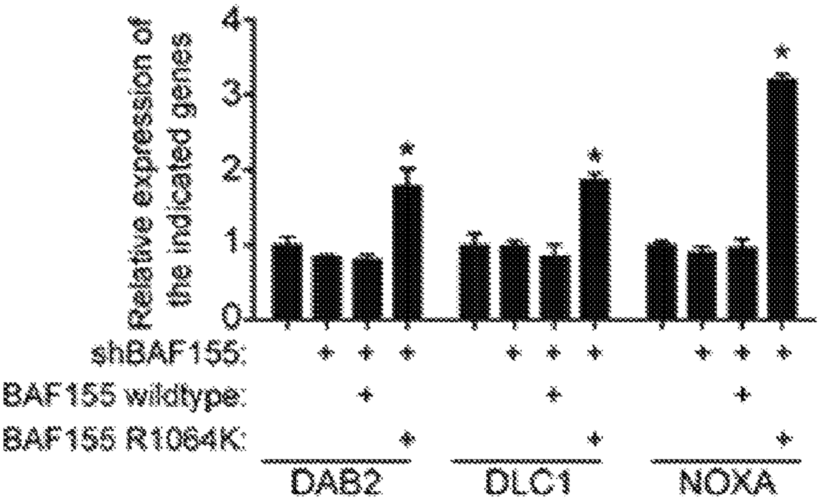
Figure 69:
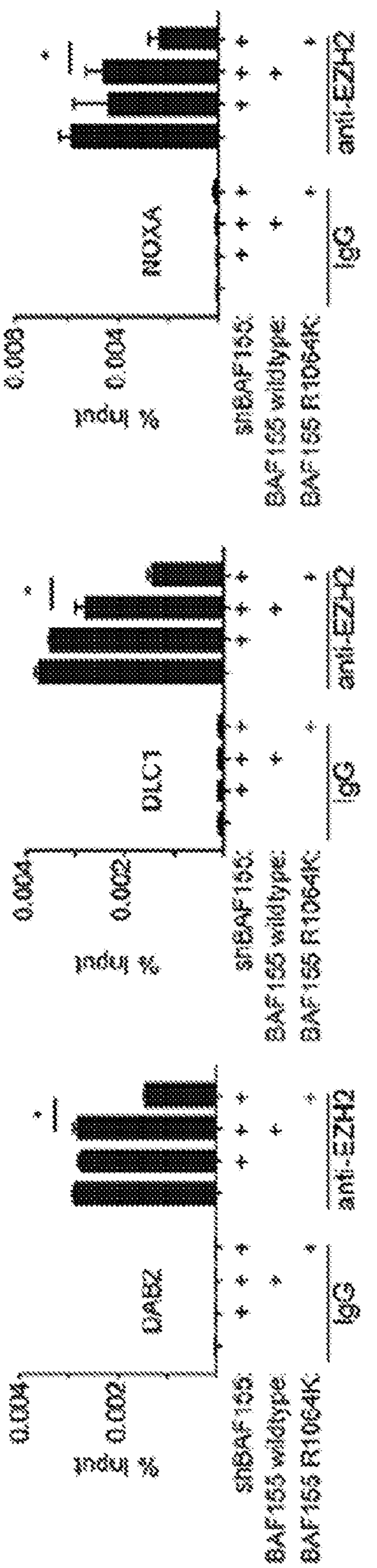
Figure 70:
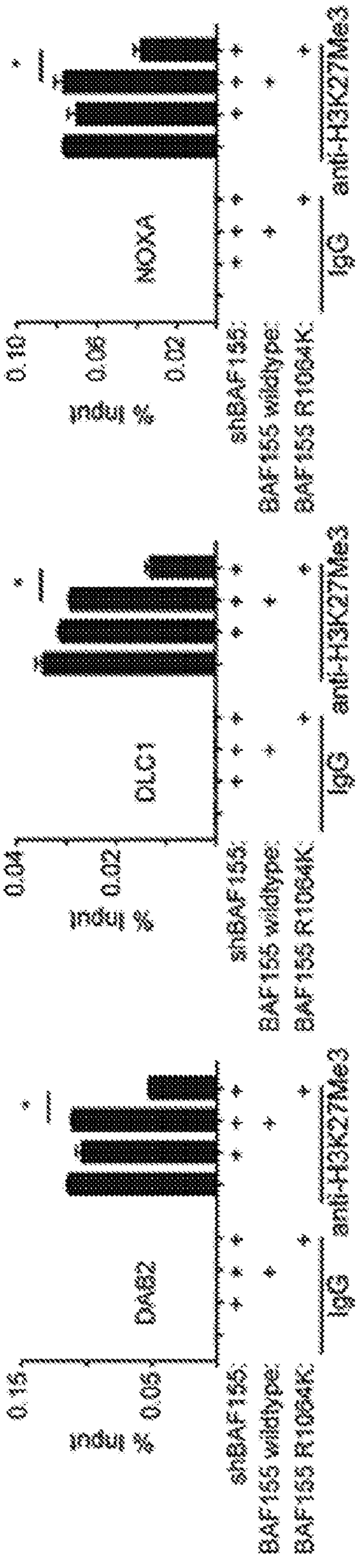
Figure 71:
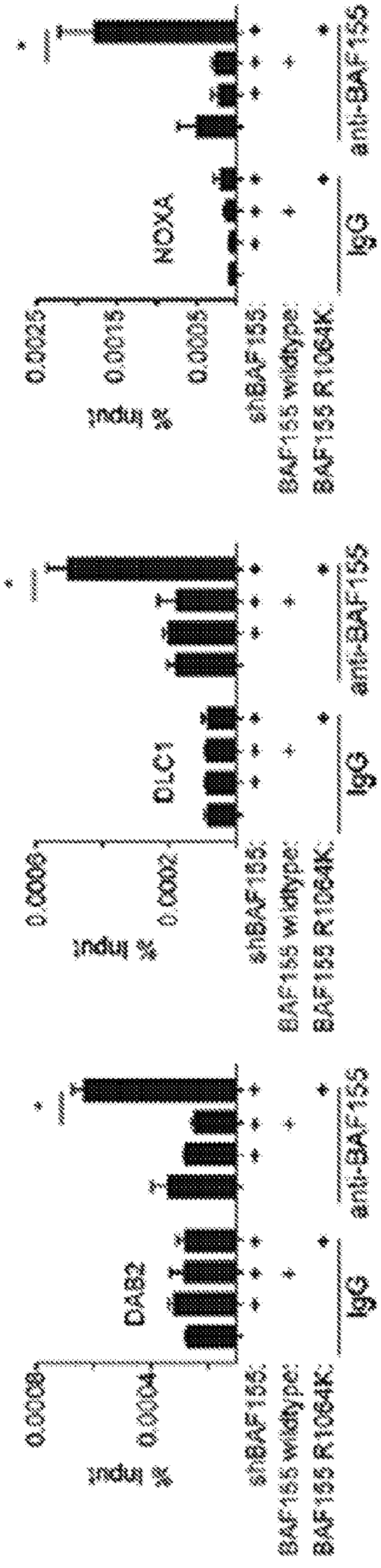
Figure 72A:
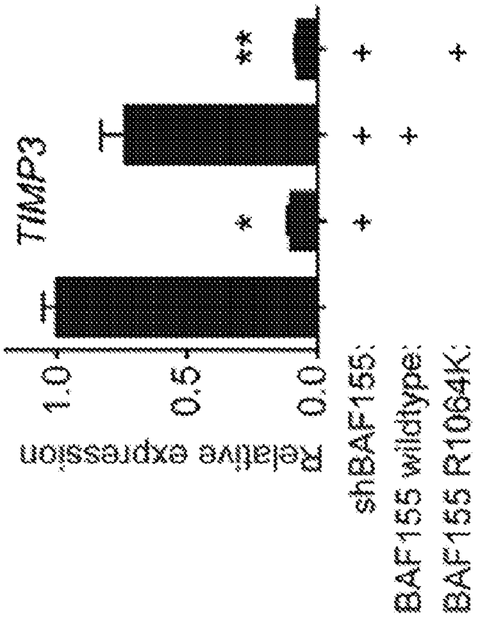
FIGS. 72A and 72B illustrate that CARM1 promotes the expression of BAF155Me target genes.
Figure 72B:
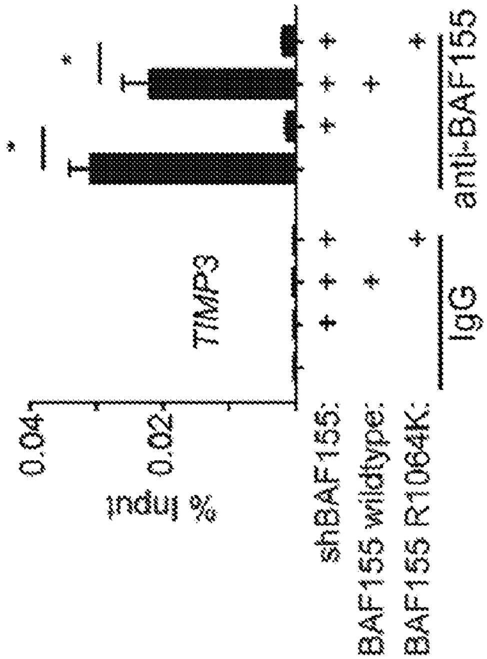

The effects of CARM1-mediated BAF155 methylation at the R1064 residue on the expression of identified EZH2/BAF155 target genes were then tested to establish that the observed antagonism is BAF155Me dependent. Toward this goal, in CARM1-high A1847 cells, endogenous BAF155 were replaced with either mutant BAF155 that can no longer be methylated by CARM1 (BAF155R1064K) or wild-type BAF155 (FIG. 67). Indeed, BAF155 R1064K mutant but not wild-type BAF155 upregulated the expression of the EZH2/BAF155 target genes (FIG. 68), indicating that only the unmethylated BAF155 can be associated with these genes. This correlated with a decrease in EZH2 and its enzymatic product H3K27Me3 at the promoter of these genes and a concurrent increase of BAF155's association with these gene promoters (FIGS. 69 and 70). In contrast, the association of BAF155 with the BAF155Me target gene TIMP3 was rescued by wild-type BAF155 but not the BAF155 R1064K, which correlated with the suppression of TIMP3 by BAF155 R1046K but not wild-type BAF155 (FIGS. 72A and 72B) Together, these data further support the notion that CARM1-mediated methylation of BAF155 drives a switch from BAF155 to EZH2 at the promoters of the BAF155/EZH2 target tumor suppressor genes (FIG. 66). Therefore, EZH2 inhibition reactivates the tumor suppressive BAF155/EZH2 target genes to promote apoptosis and inhibit proliferation of CARM1-expressing cells (FIG. 66).

EZH2 Inhibitor GSK126 Suppresses the Growth of CARM1-Expressing EOC In Vivo And Improves the Survival of Tumor Bearing Mice.

Figure 73:
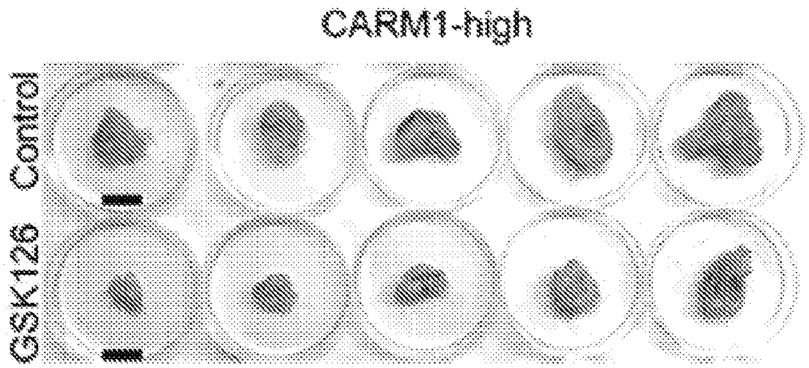
FIGS. 73 to 75 illustrate that EZH2 inhibition suppressed the growth of CARM1-expressing ovarian tumors in vivo.
Figure 74:
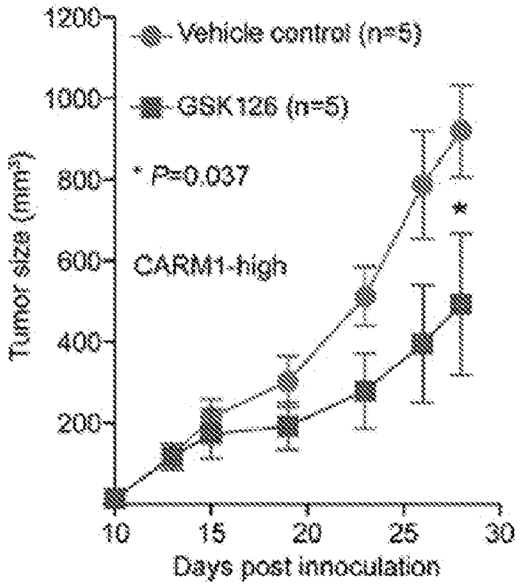
Figure 75:
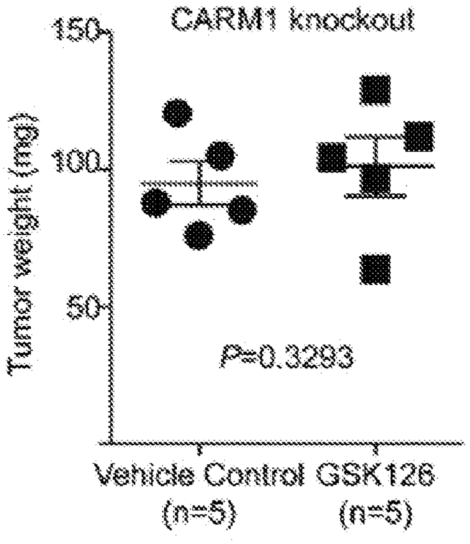
Figure 76:
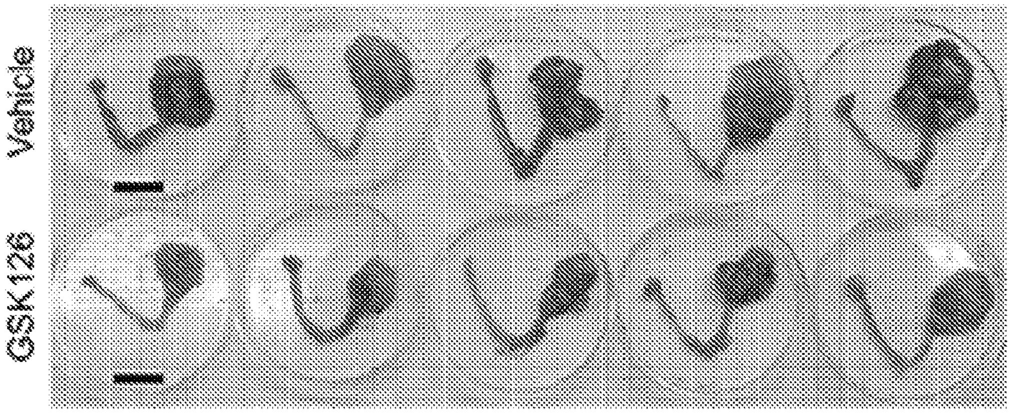
FIG. 76 illustrates images of reproductive tracks with tumors from control or GSK126 treated mice. CARM1-high A1847 ovarian cancer cells were unilaterally injected into the ovarian bursa sac of immunocompromised mice (n=5/group). Tumors were allowed to establish for one week before the mice were randomized into two different treatment groups. Mice were treated with vehicle control or GSK126 (50 mg/kg daily) for an additional three weeks. At the end of treatment, the mice were euthanized.
Figure 77:
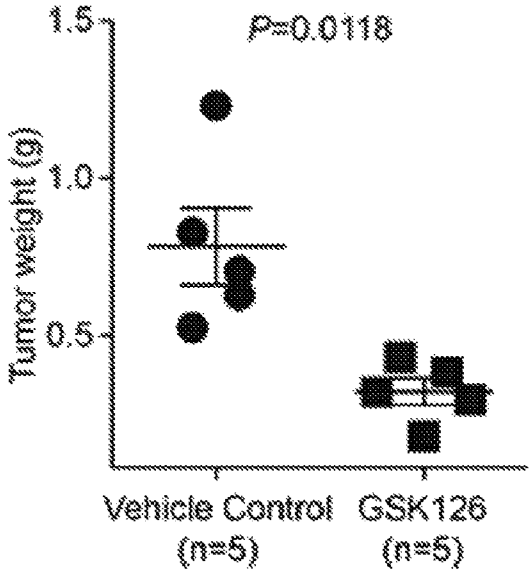
FIG. 77 illustrates tumor weights for the tumors described in FIG. 76. Tumor weight was measured as a surrogate for tumor burden from the control and GSK126 treated mice.
Figure 78:
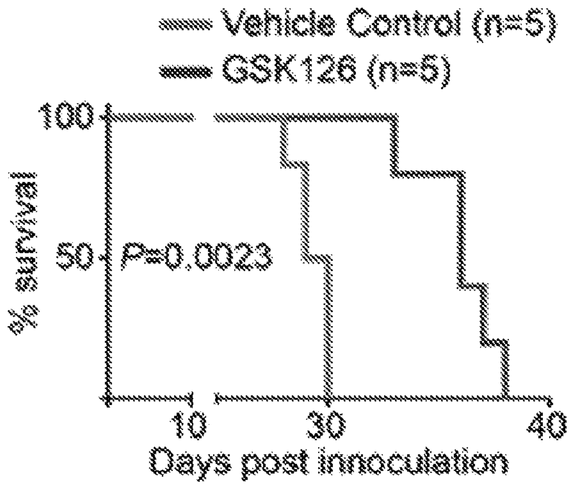
FIG. 78 illustrates the percent survival for the animals treated in FIG. 76. After stopping treatment, the mice from the indicated groups were followed for survival. Shown in FIG. 78 are the Kaplan-Meier survival curves for GSK126 or vehicle treated mice. P-value was calculated by log-rank test.

EZH2 inhibitors, such as GSK126, are used safely in clinical trials for hematopoietic malignancies (Ribrag et al. *Eur J Cancer* (2014) 50:197). To determine the effects of EZH2 inhibition in vivo on the growth of CARM1-expressing ovarian tumors, two xenograft models were utilized. In the subcutaneous xenograft models, the injected CARM1-expressing A1847 cells were first allowed to grow for one week to establish the tumors. Mice were then randomized and treated daily with vehicle control or GSK 126 (50 mg/kg) by intraperitoneal (i.p.) injection as reported (see, e.g., Bitler et al. *Nature* Medicine (2015) 21:231-8 and McCabe et al. *Nature* (2012) 492:108-12). Indeed, GSK126 treatment significantly inhibited the growth of CARM1-expressing tumors (FIGS. 73 and 74). In contrast, GSK 126 treatment failed to inhibit the growth of tumors formed by CARM1 knockout A1847 cells (FIG. 75). To more closely mimic the tumor microenvironment, A1847 cells were orthotopically transplanted into the bursa covering the ovary of immunocompromised NSG mice. Similarly, the injected cells were first allowed to grow for one week to establish the tumors. Mice were then randomized and treated daily with vehicle control or GSK126 (50 mg/kg) by intraperitoneal (i.p.) injection. Similar to what was observed in subcutaneous xenograft models, the growth of CARM1-expressing tumors was significantly inhibited by GSK126 in the orthotopic xenograft models (FIGS. 76 and 77). The survival of the treated mice was followed after stopping the treatment regimens. Importantly, GSK126 significantly improved the survival of mice bearing the orthotopically-transplanted CARM1-expressing tumors compared to controls (FIG. 78) ($P=0.0023$). Thus, the EZH2 inhibitor GSK126 was found to significantly suppress the growth of CARM1-expressing tumors and improved the survival of mice bearing these tumors.

Figure 81:
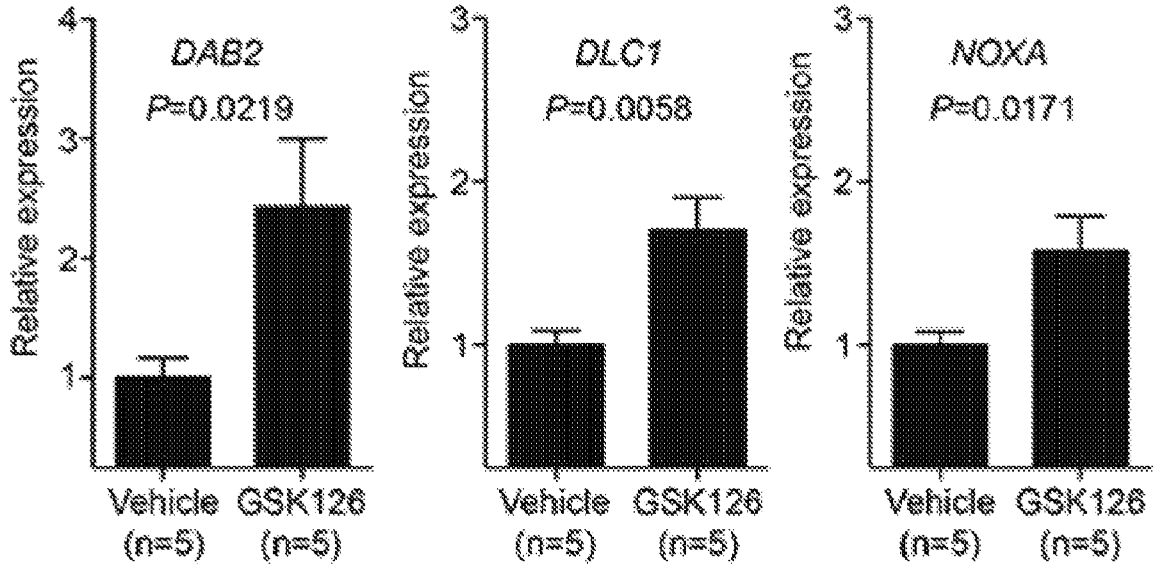
FIG. 81 illustrates the expression of the indicated EZH2/BAF155 target genes that was determined by qRT-PCR in the tumors dissected from the indicated treatment groups.
Figure 79:
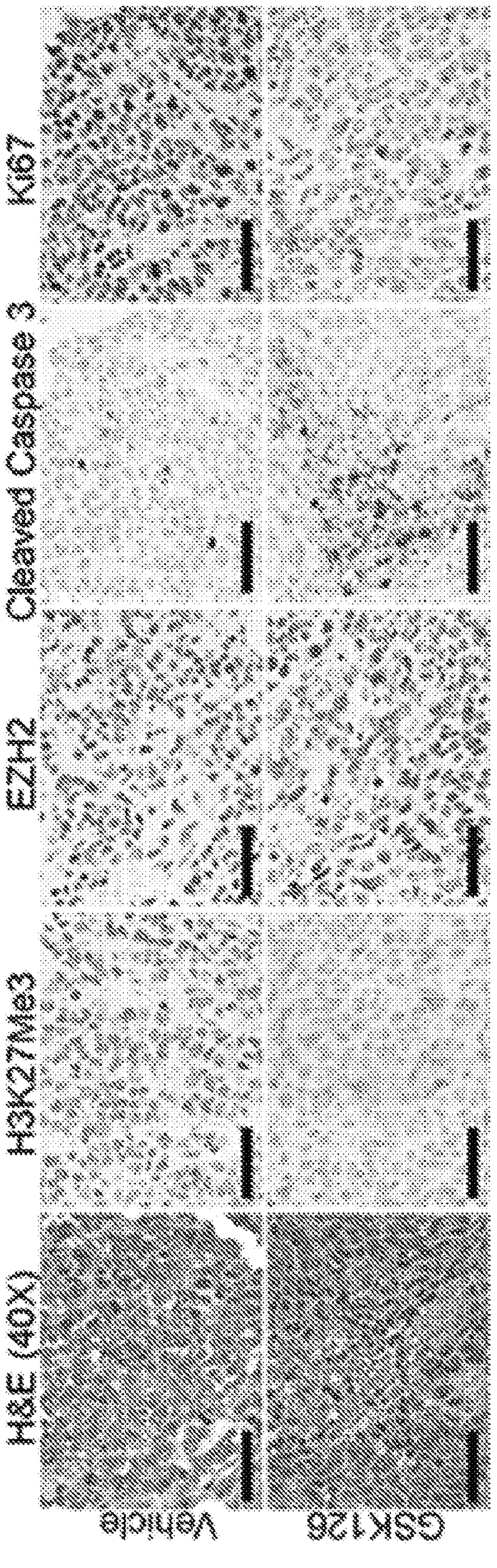
FIG. 79 illustrates immunohistochemical analysis for serial sections of tumors dissected from the indicated treatment groups where the tumor sections were stained for H3K27Me3, EZH2, cleaved caspase 3, and Ki67. Scale bar=50 μm.
Figure 80:
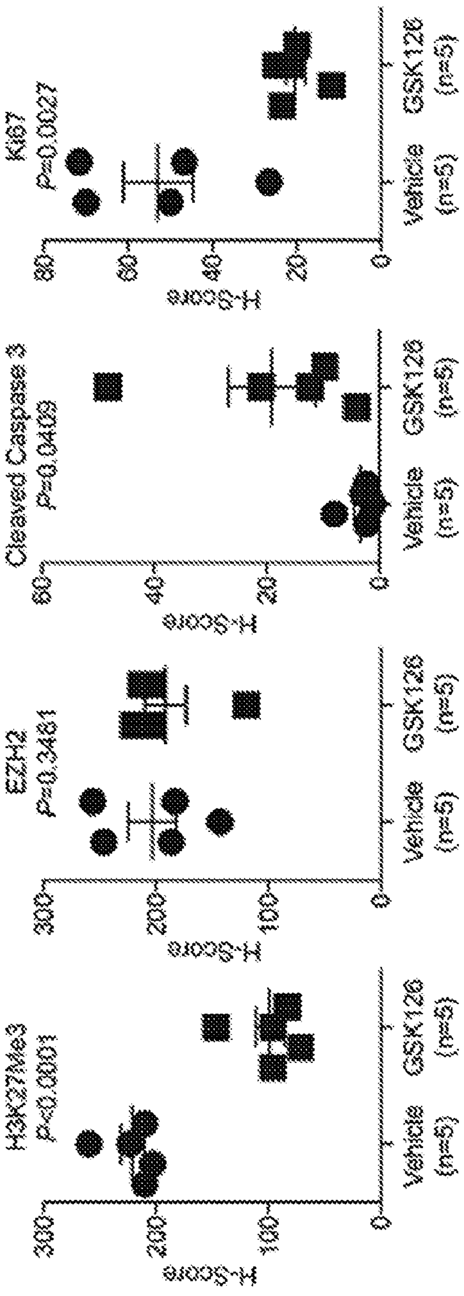
FIG. 80 illustrates histological scoring (H-score) of the indicated proteins that was calculated for 3 separate fields from 5 tumors from 5 individual mice from each of the indicated groups.
Figure 82:
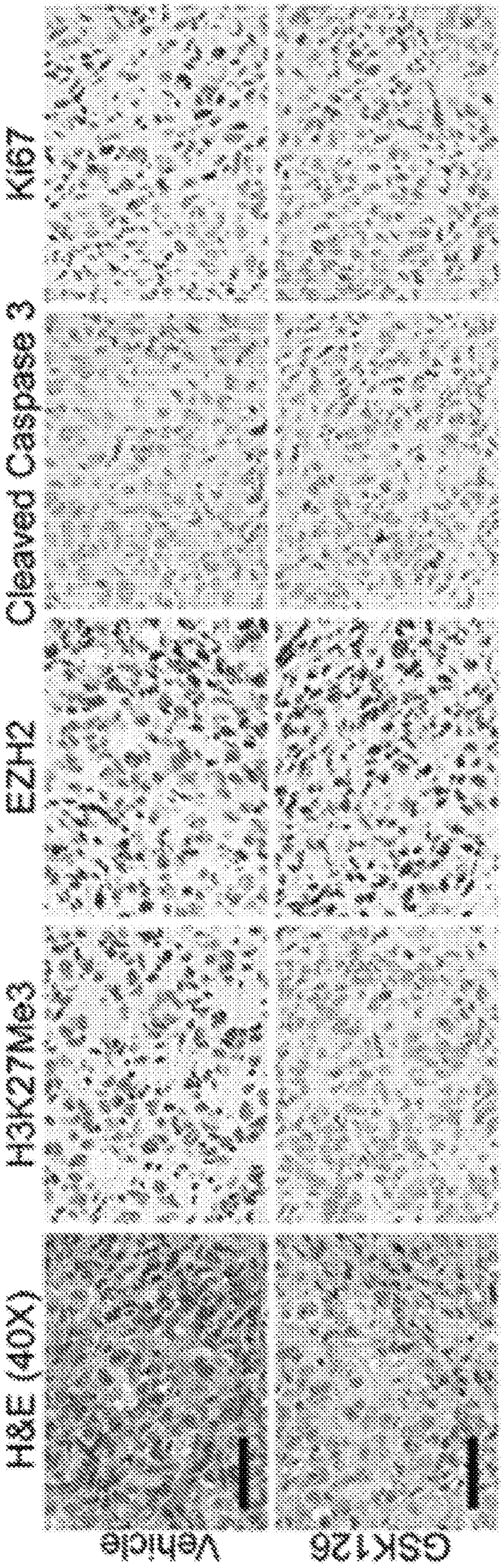
FIGS. 82 to 84 illustrate immunohistochemical analysis for serial sections of tumors dissected from mice injected with CARM1 knockout A1847 cells. Serial sections of tumors dissected from the indicated treatment groups described in FIGS. 73 to 75 were subjected to immunohistochemical staining for H3K27Me3, E7H2, cleaved caspase 3, and Ki67 (FIG. 82). Scale bar=50 μm. Histological score (H-score) of the indicated proteins was calculated for 3 separate fields from 5 tumors from 5 individual mice from each of the indicated groups (FIG. 83). Expression of the indicated EZH2/BAF155 target genes was determined by qRT-PCR in the tumors dissected from the indicated treatment groups (FIG. 84).
Figure 83:
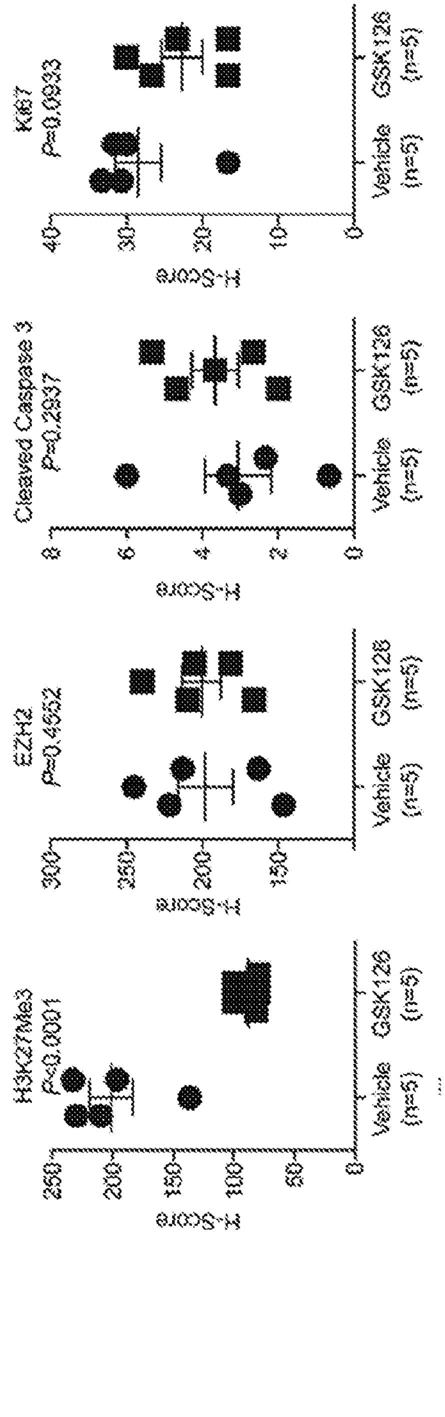
Figure 84:
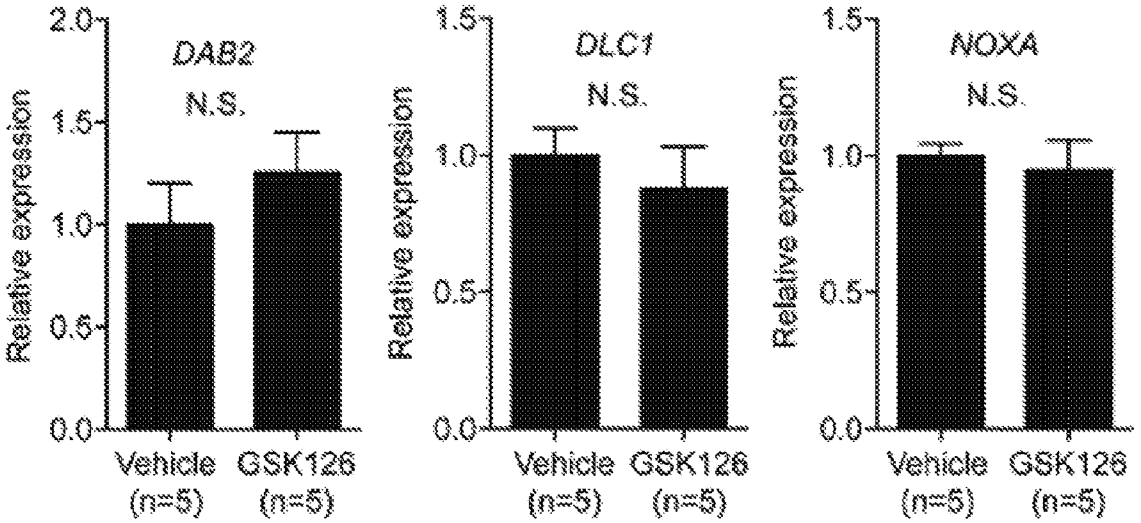
Figure 85:
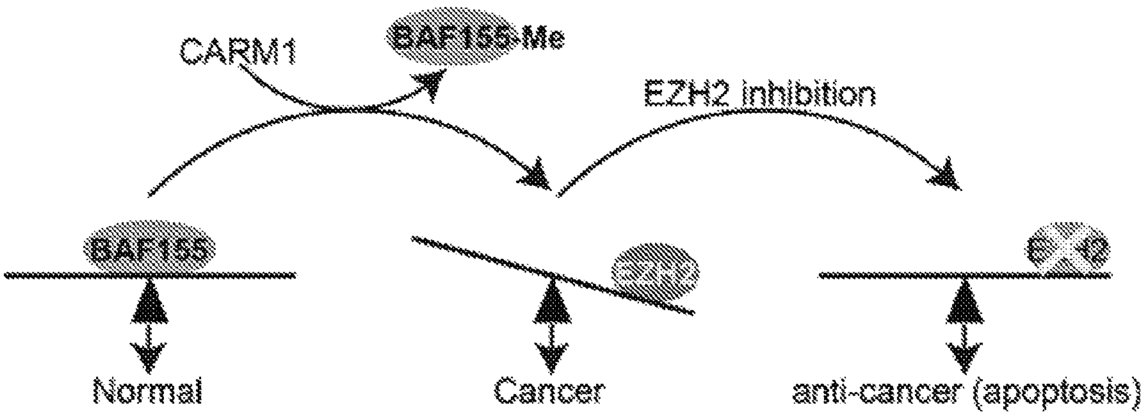
FIG. 85 illustrates how CARM1 regulates the antagonism between SWI/SNF and PRC2 through methylating BAF155. EZH2 inhibition reactivates these tumor suppressive genes to promote apoptosis, inhibit proliferation, and suppress tumor growth.

The observed tumor growth suppression in vivo was correlated with the molecular pathways underlying the CARM1-dependent effects of EZH2 inhibition. To do so, immunohistochemical (IHC) analysis was performed for markers of cell proliferation (Ki67), apoptosis (cleaved caspase 3), H3K27Me3 and EZH2. H3K27Me3 staining was decreased by GSK126, while GSK126 did not affect EZH2 staining (FIGS. 79 and 80). Further, GSK126 treatment decreased the expression of Ki67 and increased the expression of cleaved caspase 3 (FIGS. 79 and 80). Finally, the observed decrease in cell proliferation and increase in apoptosis correlated with the upregulation of the identified CARM1-regulated EZH2/BAF155 target genes such as DAB2, DLC1 and NOXA by the EZH2 inhibitor GSK126 in vivo (FIG. 81). In contrast, GSK126 did not affect the expression of Ki67 and cleaved caspase 3 in tumors formatted by CARM1 knockout cells despite the reduction of H3K27Me3 by GSK126 (FIGS. 82 and 83). Likewise, GSK126 did not increase the expression of the identified CARM1 regulated EZH2/BAF155 target genes in tumors formed by CARM1 knockout cells (FIG. 84). Together, these data support a model that EZH2 inhibition suppresses proliferation and promotes apoptosis in CARM1-expressing tumors by upregulating the EZH2/BAF155 target genes through regulating the antagonism between EZH2 (PRC2) and BAF155 (SWI/SNF) (FIG. 85).

Discussion

The foregoing data demonstrates a dependence of CARM1-expressing cells on EZH2 activity, reflecting the silencing of EZH2 target tumor suppressor genes in a CARM1-dependent manner. Mechanistically, CARM1 regulates the antagonism between EZH2 and BAF155 to drive the silencing of EZH2/BAF155 target tumor suppressor genes, which promotes apoptosis and inhibits proliferation. Specifically, CARM1-mediated methylation of BAF155 leads to the switch from BAF155 to EZH2 at the promoters of the EZH2/BAF155 target genes. Indeed, inhibition of EZH2 activity by clinically applicable small molecule restored the expression of the EZH2/BAF155 target genes. Thus, CARM1 regulates the antagonism between the BAF155-containing SWI/SNF complex and the EZH2-containing PRC2 complex by methylating BAF155. In addition, CARM1-mediated methylation of BAF155 leads to the distribution of BAF155 to the BAF155Me target genes such as TIMP3 in an EZH2-independent manner. Without being limited to any one theory, this suggests that CARM1 functions to promote the expression of BAF155Me target genes while epigenetically silencing EZH2/BAF155 target genes through EZH2 mediated H3K27Me3.

CARM1 plays a context-dependent role in cancer. Whereas the prevailing data support an overall oncogenic role of CARM1 in cancers, emerging evidence indicates that CARM1 may also positively regulate the activity of tumor suppressors (Wang et al. *Mol Cell* (2016) 64:673-87) and promote the expression of tumor suppressor genes such as TIMP3 through BAF155Me (Wang et al. *Cancer Cell* (2014) 25:21-36). Thus, directly targeting CARM1 may have unintended tumor-promoting effects. In addition, CARM1 is specifically required for postnatal survival (Yadav et al. *Proc Natl Acad Sci USA* (2003) 100:6464-8). Together, these caveats suggest that directly targeting CARM1 may not be a valid therapeutic strategy. In contrast, the foregoing data demonstrates that EZH2 inhibition can suppress the growth of CARM1-expressing tumors and improves survival of tumor bearing mice. This correlates with reactivation of EZH2-mediated silencing of tumor suppressor genes implicated in promoting apoptosis and inhibiting proliferation. Thus, targeting EZH2 activity may be advantageous compared to inhibition of CARM1 activity.

Analysis of HGSOC patients from TCGA revealed that CARM1 is amplified in ~10% and overexpressed in an additional ~10% of spontaneous HGSOC. In comparison, somatic BRCA1/2 mutations occur in ~3-4% of these cases for each gene that are among the most commonly mutated genes in HGSOC. Interestingly, CARM1 amplification does not typically occur in HGSOC with mutations in BRCA1/2. Thus, there is an even greater need for developing therapeutic approaches that correlate with CARM1 status. This is because platinum-based chemotherapy, the current standard of care, and emerging treatment with PARP inhibitors are typically more effective in patients with BRCA1/2 inactivation. In view of the foregoing, CARM1 overexpression and/or amplification may serve as a predictive marker for further development of EZH2 inhibitors as a therapy in treating epithelial ovarian cancer.

In summary, this example demonstrates that targeting EZH2 methyltrasferase activity through the use of EZH2 inhibitors in CARM1-expressing cells represents a viable therapeutic strategy. Notably, EZH2 inhibitors such as GSK126 are well-tolerated with limited toxicity in clinical trials for hematopoietic malignancies. Thus, the studies described herein provide a scientific rationale for using applicable EZH2 inhibitors for CARM1-expressing cancers, such as CARM1-expressing ovarian cancers, for which novel therapeutics are urgently needed. Given that CARM1 overexpression is frequently observed in many different cancer types, the foregoing findings have far-reaching implications for improving therapy for an array of cancer types.

We claim:

1. A method of treating an ovarian cancer in a human subject in need thereof, wherein the human subject is suffering from the ovarian cancer in which ovarian cancer cells overexpress arginine methyltransferase CARM1 relative to an expression level in normal epithelial cells, the method comprising the step of administering a therapeutically effective dose of an enhancer of zeste homolog 2 (EZH2) inhibitor to the human subject, wherein the EZH2 inhibitor is (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide (GSK126):

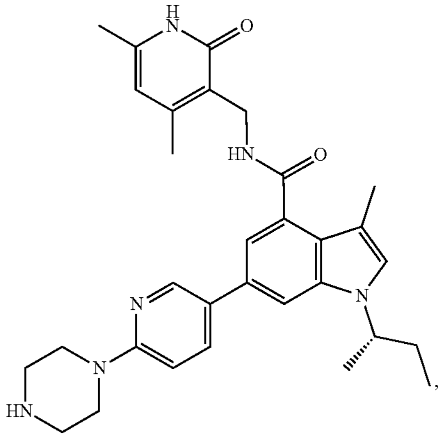 [SMILES: CC[C@H](C)n1cc(C)c2c(C(=O)NCc3c(C)cc(C)[nH]c3=O)cc(-c3ccc(N4CCNCC4)nc3)cc21]

and pharmaceutically acceptable salts, solvates, hydrates, or cocrystals thereof.

2. The method of claim 1, wherein the ovarian cancer is epithelial ovarian cancer.

3. The method of claim 2, wherein the epithelial ovarian cancer is an epithelial ovarian tumor.

4. The method of claim 1, wherein the ovarian cancer is malignant ovarian cancer.

5. The method of claim 1, wherein the overexpression of arginine methyltransferase CARM1 is at a level selected from the group of at least 2%, at least 5%, at least 8%, at least 10%, and at least 15% relative to an expression level in normal epithelial cells.

6. The method of claim 1, further comprising the step of administering a therapeutically effective dose of a platinum drug to the human subject.

7. The method of claim 6, wherein the platinum drug is selected from the group consisting of cisplatin, carboplatin, oxaliplatin, satraplatin, picoplatin, nedaplatin, triplatin tetranitrate, lipoplatin, and pharmaceutically acceptable salts, solvates, hydrates, or cocrystals thereof.

* * * * *

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 1

agcacggaaa atctacgcgg                                   20


<210> SEQ ID NO 2
<211> LENGTH: 21
<212> TYPE: DNA
<213> ORGANISM: Artificial Sequence
<220> FEATURE:
<223> OTHER INFORMATION: Synthetic sequence - Primer

<400> SEQUENCE: 2

ttcattgccc gtgatgtgac a                                 21


<210> SEQ ID NO 3
<211> LENGTH: 21
<212> TYPE: DNA
<213> ORGANISM: Artificial Sequence
<220> FEATURE:
<223> OTHER INFORMATION: Synthetic sequence - Primer

<400> SEQUENCE: 3

cctgttgccc ggtttttatg g                                 21
```

<210> SEQ ID NO 4
<211> LENGTH: 22
<212> TYPE: DNA
<213> ORGANISM: Artificial Sequence
<220> FEATURE:
<223> OTHER INFORMATION: Synthetic sequence - Primer

<400> SEQUENCE: 4
aacccaagac tacggctatt ca 22

<210> SEQ ID NO 5
<211> LENGTH: 22
<212> TYPE: DNA
<213> ORGANISM: Artificial Sequence
<220> FEATURE:
<223> OTHER INFORMATION: Synthetic sequence - Primer

<400> SEQUENCE: 5
cataaagctg tgcatactgg gg 22

<210> SEQ ID NO 6
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 6
accaagccgg atttgcgatt 20

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence - Primer

<400> SEQUENCE: 7
acttgcactt gttcctcgtg g 21

<210> SEQ ID NO 8
<211> LENGTH: 22
<212> TYPE: DNA
<213> ORGANISM: Artificial Sequence
<220> FEATURE:
<223> OTHER INFORMATION: Synthetic sequence - Primer

<400> SEQUENCE: 8
catgtgcagt acatccatac gg 22

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence - Primer

<400> SEQUENCE: 9
catcatagac gcgacctgtc a 21

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence - Primer -continued

<400> SEQUENCE: 10
gtgttcgggg agaagtcaaa 20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 11
acggatctgt gaaacgaagc 20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 12
aaaatttcca agcgccacta 20

<210> SEQ ID NO 13
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 13
acaccgcctt ctaccttcct 20

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 14
tattgtggga ggtggggata 20

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 15
ggcctgaaaa cttacgatgg 20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 16
actcccctac gcaaggattc 20

<210> SEQ ID NO 17

-continued

```
<211> LENGTH: 20
<212> TYPE: DNA
<213> ORGANISM: Artificial Sequence
<220> FEATURE:
<223> OTHER INFORMATION: Synthetic sequence - Primer

<400> SEQUENCE: 17

cgtgtgaagg cagtttggtt                                              20
```